(12) United States Patent
Frattini et al.

(10) Patent No.: US 10,399,961 B2
(45) Date of Patent: Sep. 3, 2019

(54) HETEROARYLCARBOXAMIDE DERIVATIVES AS PLASMA KALLIKREIN INHIBITORS

(71) Applicant: Boehringer Ingelheim International GmbH, Ingelheim am Rhein (DE)

(72) Inventors: Sara Frattini, Castelleone (IT); Remko Bakker, Biberach an der Riss (DE); Riccardo Giovannini, Biberach an der Riss (DE); Dieter Hamprecht, Frenchs Forest (AU); Iain Lingard, Monza (IT); Alexander Pautsch, Biberach an der Riss (DE); Bernd Wellenzohn, Friedrichshafen (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 15/770,762

(22) PCT Filed: Oct. 20, 2016

(86) PCT No.: PCT/EP2016/075221
§ 371 (c)(1),
(2) Date: Apr. 25, 2018

(87) PCT Pub. No.: WO2017/072020
PCT Pub. Date: May 4, 2017

(65) Prior Publication Data
US 2018/0305338 A1    Oct. 25, 2018

(30) Foreign Application Priority Data

Oct. 27, 2015    (EP) .................................... 15191757

(51) Int. Cl.
| C07D 401/14 | (2006.01) |
| C07D 403/12 | (2006.01) |
| A61K 31/444 | (2006.01) |
| A61K 31/4709 | (2006.01) |
| A61K 31/438 | (2006.01) |
| A61K 45/06 | (2006.01) |
| C07D 413/14 | (2006.01) |

(52) U.S. Cl.
CPC .......... C07D 401/14 (2013.01); A61K 31/438 (2013.01); A61K 31/444 (2013.01); A61K 31/4709 (2013.01); A61K 45/06 (2013.01); C07D 403/12 (2013.01); C07D 413/14 (2013.01)

(58) Field of Classification Search
CPC .. C07D 401/14; C07D 403/12; A61K 31/444; A61K 31/4709
See application file for complete search history.

(56) References Cited

FOREIGN PATENT DOCUMENTS

| WO | 2009097141 A1 | 8/2009 |
| WO | 2013111107 A1 | 8/2013 |
| WO | 2013111108 A1 | 8/2013 |
| WO | 2014188211 A1 | 11/2014 |

OTHER PUBLICATIONS

International Search Report for PCT/EP2016/075221 dated Jan. 18, 2017.
Written Opinion for PCT/EP2016/075221 dated Jan. 18, 2017.

*Primary Examiner* — Karen Cheng
(74) *Attorney, Agent, or Firm* — David L. Kershner

(57) ABSTRACT

The present invention relates to compounds of general formula I, wherein $D^1$ to $D^3$, A, $R^1$, $R^2$, Y and n are defined as in claim 1, which have valuable pharmacological properties, in particular are inhibitors of plasma kallikrein. The compounds are suitable for treatment and prevention of diseases which can be influenced by influenced by inhibition of plasma kallikrein, such as diabetic complications, particularly in the treatment of retinal vascular permeability associated with diabetic retinopathy and diabetic macular edema.

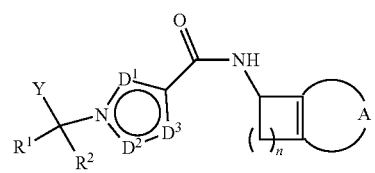

12 Claims, No Drawings

HETEROARYLCARBOXAMIDE DERIVATIVES AS PLASMA KALLIKREIN INHIBITORS

FIELD OF THE INVENTION

The present invention relates to novel 5-membered heteroarylcarboxamide derivatives, that are plasma kallikrein inhibitors, to processes for their preparation, to pharmaceutical compositions containing these compounds and to their medical use for the prophylaxis and/or treatment of diseases which can be influenced by the inhibition of plasma kallikrein. Particularly, the pharmaceutical compositions of the invention are suitable for the prophylaxis and/or therapy of diabetic complications, particularly in the treatment of retinal vascular permeability associated with diabetic retinopathy and diabetic macular edema.

BACKGROUND OF THE INVENTION

Plasma kallikrein is a trypsin-like serine protease secreted by hepatocytes in the liver as an inactive plasma prekallikrein that circulates in plasma either as a free zymogen or as a heterodimer complex bound to high molecular weight kininogen which is activated to give the active plasma kallikrein that can liberate kinins from kininogens in addition to processing other substrates. Kinins are potent mediators of inflammation that act through G protein-coupled receptors such as bradykinin receptors.

Plasma kallikrein is thought to play a role in a number of inflammatory disorders and may have numerous implications in disorders such as hereditary angioedema (HAE), retinopathy or diabetic retinopathy, proliferative and non-proliferative retinopathy, diabetic macular edema (DME), clinically significant macular edema (CSME), cystoid macular edema (CME), CME following cataract extraction, CME induced by cryotherapy, CME induced by uveitis, endophthalmitis, CME following vascular occlusion (e.g. central retinal vein occlusion, branch retinal vein occlusion, or hemiretinal vein occlusion), retinal edema, complications related to cataract surgery in diabetic retinopathy, hypertensive retinopathy, retinal trauma, dry and wet aged-related macular degeneration (AMD), polypoidal choroidal vasculopathy (PCV), choroidal neovascularization, posterior vitreous detachment (PVD), ischemic reperfusion injuries, e.g. in all kind of contexts associated with tissue and/or organ transplantation, surgically-induced brain injury, focal cerebral ischemia, global cerebral ischemia, glioma-associated edema, spinal cord injury, pain, ischemia, focal brain ischemia, neurological and cognitive deficits, deep vein thrombosis, stroke, myocardial infarction, acquired angioedema drug-related (ACE-inhibitors), edema, high altitude cerebral edema, cytotoxic cerebral edema, osmotic cerebral edema, obstructive hydrocephalus, radiation induced edema, lymph edema, traumatic brain injury, hemorrhagic stroke (e.g., cerebral stroke or subarachnoid stroke), intracerebral hemorrhage, hemorrhagic transformation of ischemic stroke, cerebral trauma associated with injury or surgery, brain aneurysm, arterio-venous malformation, reduction of blood losses during surgical procedures (e.g. cardiothoracic surgery, such as cardiopulmonary bypass or coronary artery bypass grafting), blood coagulation disorders such as thrombosis, itch, disorders with an inflammation component (such as multiple sclerosis), epilepsy, encephalitis, Alzheimer's disease, excessive daytime sleepiness, essential hypertension, increased blood pressure associated with diabetes or hyperlipidemia, renal insufficiency, chronic kidney disease, heart failure, microalbuminuria, albuminuria, proteinuria, disorders associated with increased vascular permeability (e.g. increased retinal vascular permeability, increased leg, feet, ankle vascular permeability), cerebral hemorrhage, deep vein thrombosis, coagulation from post fibrinolytic treatments, angina, angioedema, sepsis, arthritis (e.g. rheumatoid arthritis, osteoarthritis, infection arthritis), lupus, gout, psoriasis, inflammatory bowel, diabetes, diabetic complications, complications arising from metabolic syndrome, infectious diseases, astrocyte-activation related diseases (e.g. Alzheimer's disease or multiple sclerosis), Parkinson's disease, amyotrophic lateral sclerosis, Creutzfeld-Jacob disease, stroke, epilepsy and trauma (e.g. brain trauma), allergic edema e.g. airflow obstruction in chronic allergic sinusitis or perennial rhinitis; airflow obstruction in acute asthma; serositis associated with systemic lupus erythematosus (SLE), acute respiratory distress syndrome (ARDS) and other diseases.

Plasma kallikrein inhibitors are considered to be useful in the treatment of a wide range of disorders, particularly in the treatment of edema formation in diseases, e.g. edema formation related to ischemic reperfusion injuries, retinopathy or edema-associated diseases, such as hereditary angioedema, macular edema and brain edema. Plasma kallikrein inhibitors are considered to be especially useful in the treatment of retinopathy, e.g. retinopathy associated with diabetes and/or hypertension, and in the treatment of macular edema, e.g. macular edema associated with diabetes and/or hypertension.

Plasma kallikrein inhibitors suitable for therapeutic use should bind potently and with high selectivity to plasma kallikrein. They should be well absorbed from the gastrointestinal tract, be sufficiently metabolically stable and possess favorable pharmacokinetic properties. They should be non-toxic and demonstrate few side-effects.

The compounds of the invention are plasma kallikrein inhibitors and are therefore potentially useful in the treatment of disorders mentioned hereinbefore, particularly should have utility as a treatment to reduce retinal vascular permeability associated with diabetic retinopathy and diabetic macular edema retinopathy or edema-associated diseases.

Other complications of diabetes such as cerebral haemorrhage, nephropathy, cardiomyopathy and neuropathy, all of which have associations with plasma kallikrein may also be considered as targets for a plasma kallikrein inhibitor.

Low molecular weight plasma kallikrein inhibitors are known in the art, for example, the compounds disclosed in WO2013/111108, WO2013/111107 and WO2014/188211.

Object of the Present Invention

The object of the present invention is to provide new compounds, hereinafter described as compounds of formula I, in particular new 5-membered heteroarylcarboxamide derivatives, which are plasma kallikrein inhibitors and possess suitable pharmacological and pharmacokinetic properties to use them as medicaments.

A further object of the present invention is to provide effective plasma kallikrein inhibitors, in particular for the treatment of diabetic complications, for example diabetic retinopathy and diabetic macular edema, retinopathy, or edema-associated diseases.

A further object of the present invention is to provide a pharmaceutical composition comprising at least one compound according to the invention.

A further object of the present invention is to provide a combination of at least one compound according to the invention with one or more additional therapeutic agents.

Further objects of the present invention become apparent to the one skilled in the art by the description hereinbefore and in the following and by the examples.

The 5-membered heteroarylcarboxamide derivatives of the present invention may provide several advantages, such as enhanced potency, high metabolic and/or chemical stability, high selectivity and tolerability, enhanced solubility, enhanced permeability, desirable plasma protein binding, enhanced bioavailability, improved pharmacokinetic profiles, and the possibility to form stable salts.

SUMMARY OF THE INVENTION

The extension -Gn used hereinafter within the definitions is meant to identify genus n of the respective substituent. For example, $R^1$-G1 defines genus 1 of the substituent $R^1$.

In a first aspect the invention relates to a compound of formula

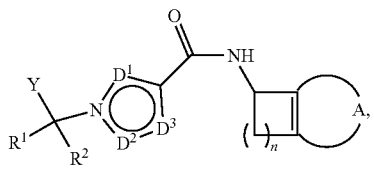

I wherein according to embodiment D-G1
of $D^1$ to $D^3$
(i) each denote N, or
(ii) 2 denote N and 1 denotes CH, or
(iii) 1 denotes N, 2 denote CH, or
(iv) each denote CH
and one or two H-atoms attached to C optionally are replaced by a substituent selected from the group consisting of $C_{1-4}$-alkyl, —$CF_3$, —$CHF_2$, —CN and —$OCH_3$;
n is 1, 2 or 3;

A according to embodiment A-G1 denotes a 4-membered bridge composed of a —C(NH$_2$)=N— unit and a second unit of —CH=CH— including both orientations for unsymmetric units, wherein a H-atom attached to a C-atom optionally is replaced by a substituent selected from the group consisting of F, Cl, CH$_3$, CF$_3$ and CHF$_2$;
$R^1$ according to embodiment $R^1$-G1 denotes H, F, CN, CF$_3$, OH, or —OCH$_3$,
$R^2$ according to embodiment $R^2$-G1 denotes H, F, CN, CF$_3$, CHF$_2$, —OCH$_3$ or a $C_{1-3}$-alkyl group optionally substituted by —OH,
or $R^1$ and $R^2$ according to embodiment $R^{1/2}$-G1 together denote =O or together with the carbon atom they are attached to form a 3-7 membered saturated ring system wherein 1 —CH$_2$— group optionally is replaced by O, S or NH,
Y according to embodiment Y-G1 denotes the group $Y^1$ or $Y^2$-L-$Y^1$—, wherein
  $Y^1$ is selected from the group consisting of a phenyl ring, a tetrazolyl ring,
  a 5-membered heteroaromatic ring containing 1 —NH—, —O— or —S— ring member,
  a 5-membered heteroaromatic ring containing 1 —NH—, —O— or —S— ring member and additionally 1 or 2 =N— ring members,
  a 6-membered heteroaromatic ring containing 1, 2 or 3 =N— ring members,
    wherein optionally a second ring is annulated to said phenyl ring or to said 5- or 6-membered heteroaromatic rings and said second ring is 5- or 6-membered carbocyclic or heterocyclic, partially unsaturated, aromatic or heteroaromatic and optionally 1 or 2 ring members are independently selected from =N— and —NH—, or 1 ring member is 1 =N— and 1 ring member is O, S or —NH—,
    and wherein in said second ring 1 —CH$_2$— group linked to a N-atom optionally is replaced by —C(O)—, and
    wherein said phenyl ring, tetrazolyl ring, 5- or 6-membered heteroaromatic ring, annulated phenyl ring and annulated 5- or 6-membered heteroaromatic ring are optionally substituted at one or two carbon atoms by a halogen atom, $C_{1-3}$-alkyl, —CF$_3$, —CN, —OH, HO—$C_{1-3}$-alkyl- or $C_{1-3}$-alkyloxy-, and
    wherein the H-atom in one or more NH groups present in Y optionally is replaced by $C_{1-3}$-alkyl-;
  L denotes a bond or a linker selected from —C(R$_3$R$_4$)— and —O—, wherein
    $R^3$ denotes H, F, CN, $C_{1-3}$-alkyl, CF$_3$, CHF$_2$, —OH or —OCH$_3$,
    $R^4$ denotes H, F, CN, CF$_3$, CHF$_2$, —OCH$_3$ or a $C_{1-3}$-alkyl group optionally substituted by —OH,
    or $R^3$ and $R^4$ together denote =O or together with the carbon atom they are attached to form a 3-7 membered saturated ring system wherein 1 —CH$_2$— group optionally is replaced by O, S or NH,
  $Y^2$ is attached to L via a C-atom or, where applicable, via a N-atom and is selected from the group consisting of
    a phenyl ring, a tetrazolyl ring,
    a 5-membered heteroaromatic ring containing 1 >N—, —NH—, —O— or —S— ring member,
    a 5-membered heteroaromatic ring containing 1 >N—, —NH—, —O— or —S— ring member and additionally 1 or 2 =N— ring members,
    a 6-membered heteroaromatic ring containing 1, 2 or 3 =N— ring members,
    a 5- or 6-membered carbocyclic or heterocyclic, saturated or partially unsaturated ring wherein optionally 1 or 2 ring members are independently selected from a N-atom and —NH—, or 1 ring member is a N-atom and 1 ring member is O, S or —NH—,
    and wherein 1 —CH$_2$— group linked to a N-atom optionally is replaced by —C(O)—, and
    wherein said phenyl ring, tetrazolyl ring, 5- or 6-membered heteroaromatic ring, 5- or 6-membered carbocyclic or heterocyclic, saturated or partially unsaturated rings are optionally substituted at one or two carbon atoms by one or, in case of saturated carbon atoms, also by two groups independently selected from halogen atoms, $C_{1-3}$-alkyl, —CF$_3$, —CN, —OH, HO—$C_{1-3}$-alkyl- and $C_{1-3}$-alkyloxy-, with the proviso that two substituents containing an O-atom cannot be attached to the same carbon atom, and
    wherein the H-atom in one or more NH groups present in $Y^2$ optionally is replaced by $C_{1-3}$-alkyl-;
wherein in any definition mentioned hereinbefore and if not specified otherwise, any alkyl group or sub-group may be straight-chained or branched, the isoforms, tautomers, stereoisomers, metabolites, prodrugs, solvates, hydrates, and the salts thereof, particularly the physiologically acceptable salts thereof with inorganic or organic acids or bases, or the combinations thereof.

In a further aspect this invention relates to a pharmaceutical composition, comprising one or more compounds of general formula I or one or more pharmaceutically acceptable salts thereof according to the invention, optionally together with one or more inert carriers and/or diluents.

In a further aspect this invention relates to a method for treating diseases or conditions which can be influenced by the inhibition of plasma kallikrein in a patient in need thereof characterized in that a compound of general formula I or a pharmaceutically acceptable salt thereof is administered to the patient.

According to another aspect of the invention, there is provided a method for treating diabetic complications, particularly in the treatment of retinal vascular permeability associated with diabetic retinopathy and diabetic macular edema, in a patient in need thereof characterized in that a therapeutically effective amount of a compound of general formula I or a pharmaceutically acceptable salt thereof is administered to the patient.

According to another aspect of the invention, there is provided the use of a compound of the general formula I or a pharmaceutically acceptable salt thereof for the manufacture of a medicament for a therapeutic method as described hereinbefore and hereinafter.

According to another aspect of the invention, there is provided a compound of the general formula I or a pharmaceutically acceptable salt thereof for use in a therapeutic method as described hereinbefore and hereinafter.

In a further aspect this invention relates to a method for treating a disease or condition which can be influenced by the inhibition of plasma kallikrein in a patient that includes the step of administering to the patient in need of such treatment a therapeutically effective amount of a compound of the general formula I or a pharmaceutically acceptable salt thereof in combination with a therapeutically effective amount of one or more additional therapeutic agents.

In a further aspect this invention relates to the use of a compound of the general formula I or a pharmaceutically acceptable salt thereof in combination with one or more additional therapeutic agents for the treatment of diseases or conditions which which can be influenced by the inhibition of plasma kallikrein in a patient in need thereof.

In a further aspect this invention relates to a pharmaceutical composition which comprises a compound according to general formula I or a pharmaceutically acceptable salt thereof and one or more additional therapeutic agents, optionally together with one or more inert carriers and/or diluents.

Other aspects of the invention become apparent to the one skilled in the art from the specification and the experimental part as described hereinbefore and hereinafter.

DETAILED DESCRIPTION

Unless otherwise stated, the groups, residues, and substituents, particularly $D^1$ to $D^3$, -A-, $R^1$, $R^2$, Y and n are defined as above and hereinafter. If residues, substituents, or groups occur several times in a compound, they may have the same or different meanings. Some preferred meanings of individual groups and substituents of the compounds according to the invention will be given hereinafter as embodiments of the invention. Any and each of the embodiments D-G1 to D-G3, A-G1 to A-G2, $R^1$-G1 to $R^1$-G4, $R^2$-G1 to $R^2$-G4, $R^{1/2}$-G1, Y-G1 to Y-G5, and embodiments of n hereinafter may be combined with each other.

$D^1$ to $D^3$:

D-G2:

According to another embodiment D-G2 of the invention of $D^1$ to $D^3$ (i) 2 denote N and 1 denotes CH, or (ii) 1 denotes N, and 2 denote CH, and one or two H-atoms attached to C optionally are replaced by a substituent selected from the group consisting of $C_{1-3}$-alkyl, —$CF_3$, —CN and —$OCH_3$.

D-G3:

According to another embodiment D-G3 of the invention $D^1$ denotes CH, $D^2$ denotes N, $D^3$ denotes N or CH, and one or two H-atoms attached to C optionally are replaced by a substituent selected from the group consisting of $C_{1-3}$-alkyl and —$CF_3$.

$\overset{\frown}{\underset{\smile}{A}}$:

A-G2:

According to another embodiment A-G2 of the invention A is selected from the group consisting of —C(NH$_2$)=N—CH=CH—, —N=C(NH$_2$)—CH=CH— and —CH=C(NH$_2$)—N=CH—, including both orientations regarding the attachment points, wherein a H-atom attached to a C-atom optionally is replaced by a substituent selected from the group consisting of F, CH$_3$ and CF$_3$.

$R^1$:

$R^1$-G2:

$R^1$ according to embodiment $R^1$-G2 denotes H, F, CN, CH$_3$ or CF$_3$.

$R^1$-G3:

$R^1$ according to embodiment $R^1$-G3 denotes H, F or CH$_3$.

$R^1$-G4:

$R^1$ according to embodiment $R^1$-G4 denotes H.

$R^2$:

$R^2$-G2:

$R^2$ according to embodiment $R^2$-G2 denotes H, F, CN, CF$_3$ or a $C_{1-3}$-alkyl group optionally substituted by —OH.

$R^2$-G3:

$R^2$ according to embodiment $R^2$-G3 denotes H, F, CF$_3$ or CH$_3$.

$R^2$-G4:

$R^2$ according to embodiment $R^2$-G4 denotes H.

Y:

Y-G2:

Y according to embodiment Y-G2 denotes the group $Y^1$ or $Y^2$-L-$Y^1$—, wherein $Y^1$ is selected from the group consisting of a phenyl ring and a pyridyl ring, wherein optionally a second ring is annulated to said phenyl or pyridyl ring and said second ring is 5- or 6-membered, aromatic or heteroaromatic and optionally 1 or 2 ring members are independently selected from =N— and —NH—, or 1 ring member is 1 =N— and 1 ring member is O, S or —NH—, wherein said phenyl ring, pyridyl ring, annulated phenyl ring and annulated pyridyl ring are optionally substituted at one or two carbon atoms by a halogen atom, $C_{1-3}$-alkyl, or —$CF_3$, and wherein the H-atom in one or more NH groups present in Y optionally is replaced by $C_{1-3}$-alkyl;

L denotes a bond or —CH₂—, and
Y² is attached to L via a N-atom and is selected from the group consisting of
  a 5-membered heteroaromatic ring containing 1 >N— ring member as the attachment point and optionally additional 1 or 2 =N— ring members,
  a 5- or 6-membered heterocyclic, saturated or partially unsaturated ring containing 1 >N— ring member as the attachment point and optionally additional 1 or 2 O or NH ring members, wherein 1 —CH₂— group linked to a N-atom optionally is replaced by —C(O)—, and
  wherein said 5-membered heteroaromatic ring and 5- or 6-membered heterocyclic, saturated or partially unsaturated rings are optionally substituted at a carbon atom by a group selected from $C_{1-3}$-alkyl, —CF₃, —OH, HO—$C_{1-3}$-alkyl- and $C_{1-3}$-alkyloxy-.

Y-G3:
Y according to embodiment Y-G3 denotes the group $Y^1$, wherein
  $Y^1$ is a quinolinyl or isoquinolinyl ring optionally substituted at one or two carbon atoms by a halogen atom, $C_{1-3}$-alkyl, or —CF₃.

Y-G4:
Y according to embodiment Y-G4 denotes the group or $Y^2$-L-$Y^1$—, wherein
  $Y^1$ is a phenyl ring, optionally substituted at one or two carbon atoms by a halogen atom, $C_{1-3}$-alkyl, or —CF₃,
  L denotes —CH₂—, and
  Y² is attached to L via a N-atom and is selected from the group consisting of a 5-membered heteroaromatic ring containing 1 >N— ring member as the attachment point and optionally additional 1 or 2 =N— ring members,
  a 5- or 6-membered heterocyclic, saturated or partially unsaturated ring containing 1 >N— ring member as the attachment point and optionally additional 1 O or NH ring members, wherein 1 —CH₂— group linked to a N-atom optionally is replaced by —C(O)—, and
  wherein said 5-membered heteroaromatic ring and 5- or 6-membered heterocyclic, saturated or partially unsaturated rings are optionally substituted at a carbon atom by a group selected from $C_{1-3}$-alkyl and —CF₃.

Y-G5:
Y according to embodiment Y-G5 denotes the group $Y^2$-L-$Y^1$—, wherein
  $Y^1$ is a pyridyl ring, optionally substituted at one or two carbon atoms by a halogen atom, $C_{1-3}$-alkyl, or —CF₃,
  L denotes a bond, and
  Y² is attached to L via a N-atom and is selected from the group consisting of a 5- or 6-membered heterocyclic, saturated or partially unsaturated ring containing 1 >N— ring member as the attachment point and optionally additional 1 =N— ring member, wherein said 5- or 6-membered heterocyclic, saturated or partially unsaturated ring is optionally substituted at a carbon atom by a group selected from $C_{1-3}$-alkyl, —CF₃.

According to one embodiment n denotes 2.
According to another embodiment n denotes 3.
Examples of preferred subgeneric embodiments (E) according to the present invention are set forth in the following table 1, wherein each substituent group of each embodiment is defined according to the definitions set forth hereinbefore. For example, the entry -G1 in the column under $R^1$— and the line of E1 means that in embodiment E1 substituent $R^1$ is selected from the definition designated $R^1$-G1. The same applies analogously to the other variables incorporated in the general formulas.

TABLE 1

| E | D¹ to D³ | A | $R^1$- | $R^2$- | Y | n |
|---|---|---|---|---|---|---|
| E1 | D-G1 | A-G1 | $R^1$-G1 | $R^2$-G1 | Y-G1 | 1, 2 or 3 |
| E2 | D-G1 | A-G1 | $R^{1/2}$-G1 | | Y-G1 | 1, 2 or 3 |
| E3 | D-G2 | A-G2 | $R^1$-G2 | $R^2$-G2 | Y-G2 | 2 or 3 |
| E4 | D-G3 | A-G3 | $R^1$-G3 | $R^2$-G3 | Y-G3 | 2 or 3 |
| E5 | D-G3 | A-G3 | $R^1$-G3 | $R^2$-G3 | Y-G4 | 2 or 3 |
| E6 | D-G3 | A-G3 | $R^1$-G3 | $R^2$-G3 | Y-G5 | 2 or 3 |

Stereochemistry

In one embodiment the compounds have the stereochemistry depicted in formula I.1 in a second embodiment the compounds have the stereochemistry depicted in formula I.2

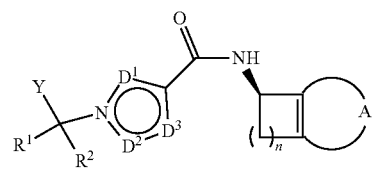

I.1

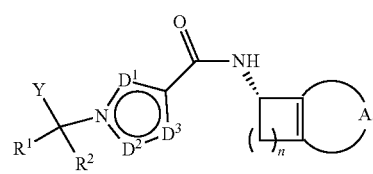

I.2

Particularly preferred compounds, including their tautomers and stereoisomers, the salts thereof, or any solvates or hydrates thereof, are described in the experimental section hereinafter.

The compounds according to the invention and their intermediates may be obtained using methods of synthesis which are known to the one skilled in the art and described in the literature of organic synthesis. Preferably the compounds are obtained analogously to the methods of preparation explained more fully hereinafter, in particular as described in the experimental section. In some cases the sequence adopted in carrying out the reaction schemes may be varied. Variants of these reactions that are known to the skilled man but are not described in detail here may also be used. The general processes for preparing the compounds according to the invention will become apparent to the skilled man on studying the schemes that follow. Starting compounds are commercially available or may be prepared by methods that are described in the literature or herein, or may be prepared in an analogous or similar manner. Before the reaction is carried out any corresponding functional groups in the compounds may be protected using conventional protecting groups. These protecting groups may be cleaved again at a suitable stage within the reaction sequence using methods familiar to the skilled man.

The compounds according to the invention and their intermediates may be obtained using methods of synthesis which are known to the one skilled in the art and described in the literature of organic synthesis for example using methods described in "Comprehensive Organic Transformations, $2^{nd}$ edition", Richard C. Larock, Wiley-VCH, 2009, and "March's Advanced Organic Chemistry, $6^{th}$ edition", Michael B. Smith, Jerry March, Wiley Interscience, 2007. Preferably the compounds are obtained analogously to the methods of preparation explained more fully hereinafter, in particular as described in the experimental section. In some cases the sequence adopted in carrying out the reaction schemes may be varied. Variants of these reactions that are known to the skilled man but are not described in detail here may also be used. The general processes for preparing the compounds according to the invention will become apparent to the skilled man on studying the schemes that follow. Starting compounds are commercially available or may be prepared by methods that are described in the literature or herein, or may be prepared in an analogous or similar manner. Before the reaction is carried out any corresponding functional groups in the compounds may be protected using conventional protecting groups. These protecting groups may be cleaved again at a suitable stage within the reaction sequence using methods familiar to the skilled man and described in the literature for example in "Protecting Groups, 3$^{rd}$ Edition", Philip J. Kocienski, Theime, 2005 or "Greene's Protective Groups in Organic Synthesis, 4th Edition", Peter G. M. Wuts, Theadora W. Greene, John Wiley and Sons, 2007.

Scheme 1:

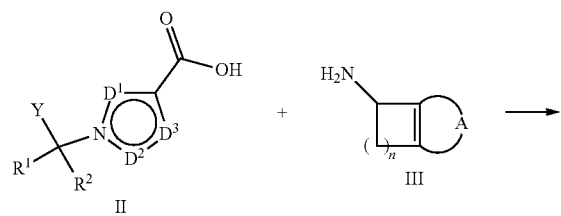

Scheme 2:

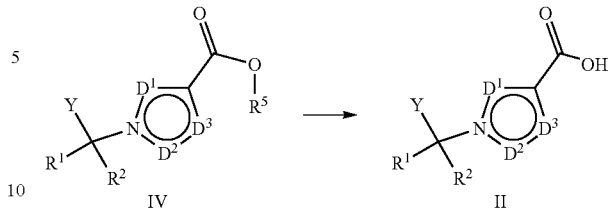

Scheme 2:

Acids of formula II, wherein $R^1$, $R^2$, Y and $D^1$ to $D^3$ have the meanings as defined hereinbefore, can be prepared from the corresponding ester IV through the removal of cleavable group $R^5$, typically by hydrolysis or hydrogenolysis. Suitable $R^5$ groups include lower alkyl such as ethyl or methyl esters, in these cases $R^5$ can be removed by hydrolysis with a hydroxide base such as NaOH, LiOH, KOH in a mixture of water and a suitable miscible solvent (e.g. tetrahydrofuran, methanol, ethanol, 1,4-dioxane etc. or mixtures of these), with heating if necessary. The acid may be isolated either as a salt with the metal cation or as a free acid. An alternative $R^5$ group is tert-butyl, which can be removed by treatment with an acid (e.g. hydrochloric acid) in a suitable solvent (e.g. dichloromethane, 1,4-dioxane, methanol, ethanol, tetrahydrofuran, water or mixtures of these). Another $R^5$ group is benzyl, which can be removed by hydrogenation with a suitable catalyst (e.g. palladium on carbon, platinum oxide etc.) in a suitable solvent (e.g. ethanol, methanol, tetrahydrofuran, dichloromethane, ethyl acetate etc.) under an atmosphere of hydrogen.

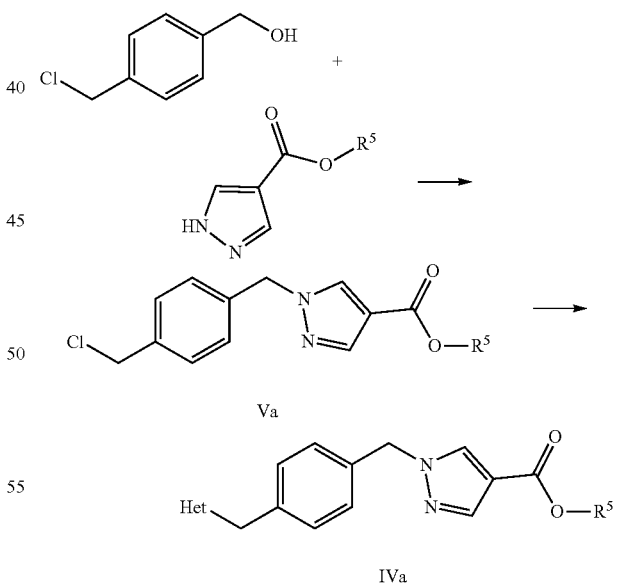

Scheme 1:

Compounds of formula I can be prepared by the reaction of a suitable acid of formula II (either as a free acid or as a salt with a suitable metal cation such as Li+, Na+, K+ etc.) and a suitable amine of formula III (either as a free amine or as a salt such as a hydrochloride, hydrobromide etc.), wherein $R^1$, $R^2$, Y, $D^1$ to $D^3$, n and A have the meanings as defined hereinbefore, in a suitable solvent (e.g. dichloromethane, tetrahydrofuran, 1,4-dioxane, N,N-dimethylformamide, N,N-dimethylacetamide, 1-methyl-2-pyrrolidinone etc.) in the presence of a suitable coupling agent (e.g. O-(7-azabenzotriazol-1-yl)-N,N,N',N'-tetramethyluronium-hexafluorophosphate (HATU), O-(benzotriazol-1-yl)-N,N,N',N'-tetramethyluronium tetrafluoroborate (TBTU), (benzotriazol-1-yloxy)tripyrrolidinophosphonium hexafluorophosphate (PyBOP), carbodiimide reagents etc.) and a base (e.g. triethylamine, N,N-diisopropylamine, pyridine etc.) to form an amide bond.

Scheme 3:

Some esters of formula IVa, wherein $R^1$ and $R^2$ denote H, $R^5$ denotes a cleavable group, $D^1$ and $D^3$ denote CH, $D^2$ denotes N, and Y denotes $Y^2$-L-$Y^1$—, wherein $Y^1$ denotes a phenyl ring, L denotes —$CH_2$— and $Y^2$ (corresponding to Het in formula IVa) denotes a tetrazolyl ring or a heteroaromatic ring as defined hereinbefore, can be prepared by reaction of 4-chloromethyl benzylalcohol with an ester of 1H-pyrazole-4-carboxylic acid in a Mitsonobu reaction with suitable reagents (e.g. triphenylphosphine plus diethylazodicarboxylate (DEAD) or diisopropyl azodicarboxylate (DIAD) etc.) in a suitable solvent (e.g. tetrahydrofuran, 1,4-dioxane, diethylether etc). The resulting intermediate Va can then be reacted with a heteroaromatic nucleophile in the presence of a suitable base (e.g. sodium hydride, cesium carbonate, potassium carbonate etc.) in a suitable solvent (e.g. tetrahydrofuran, N,N-dimethylformamide etc.) to give intermediates of formula IVa.

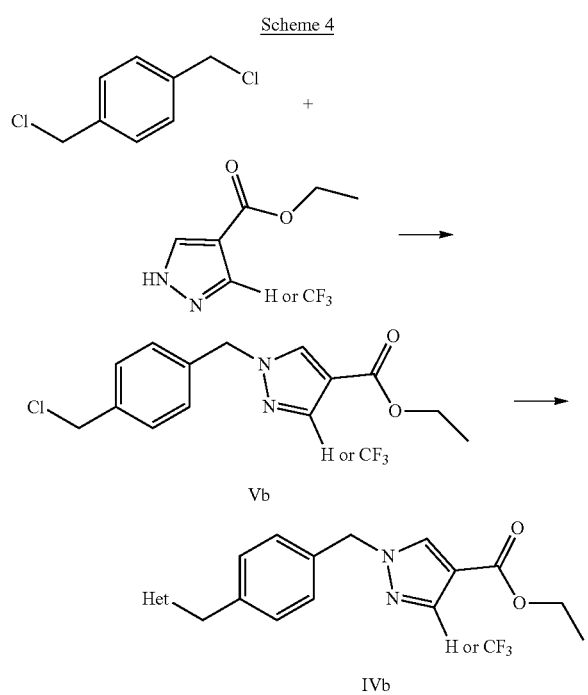

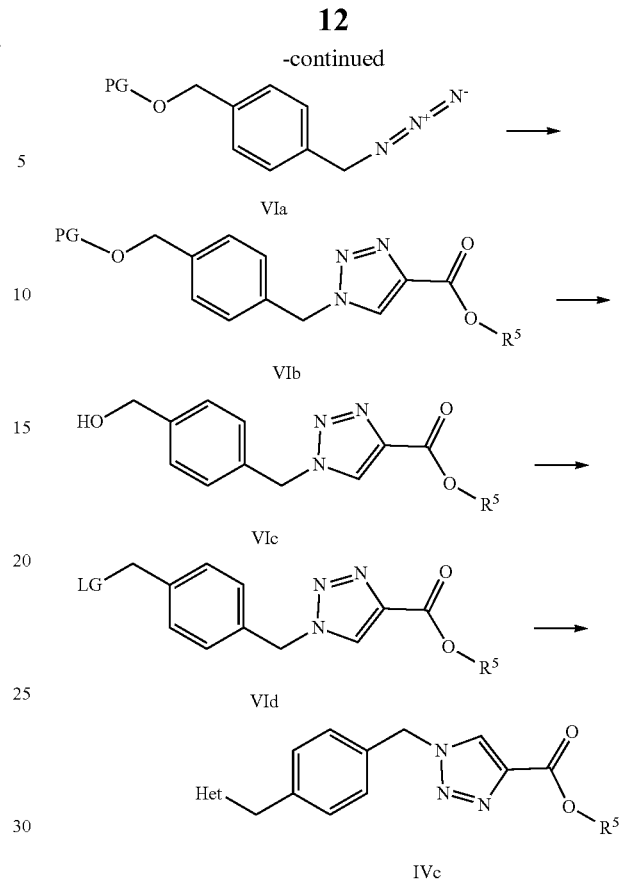

Scheme 4:

Some esters of formula IVb, which is defined as formula IVa except for $D^3$ denoting CH or C(CF$_3$), can be prepared by reaction of 1,4-bis chloromethylbenzene with 1H-pyrazole-4-carboxylic acid ethyl ester or 3-trifluoromethyl-1H-pyrazole-4-carboxylic acid ethyl ester in the presence of a suitable base (e.g. sodium hydride, cesium carbonate, potassium carbonate etc.) in a suitable solvent (e.g. tetrahydrofuran, N,N-dimethylformamide etc.). The resulting intermediate Vb can be further reacted as described in Scheme 3 to give intermediates of formula IVb.

Scheme 5:

Some esters of formula IVc, which is defined as formula IVa except for $D^3$ denoting N, can be prepared by the protection of the hydroxyl group of 4-chloromethylbenzylalcohol with a suitable protecting group PG, e.g. tert-butyldimethylsilyl ether, tert-butyl ether, tetrahydropyran etc., to give an intermediate of formula VI. This can then be reacted with sodium azide in N,N-dimethylformamide or another suitable solvent to give an intermediate of formula VIa which can be reacted with a suitable propiolic acid ester under copper mediated catalytic conditions (e.g. ethyl propiolate, tert-butyl propiolate etc with catalytic copper sulfate and sodium ascorbate in water/tert-butanol) to give a triazole intermediate of formula VIb. The protecting group can then be removed under conditions appropriate for the group chosen and the hydroxyl group liberated in intermediate VIc converted into a suitable leaving group LG, e.g. Br, Cl, mesylate, through the use of a suitable reagent (e.g. PBr$_3$, SOCl$_2$, methanesulfonyl chloride) in the presence of a suitable base (e.g. triethylamine, N,N-diisopropylamine, pyridine etc) if required. The resulting intermediate VId can be further reacted as described in Scheme 3 to give intermediates of formula IVc.

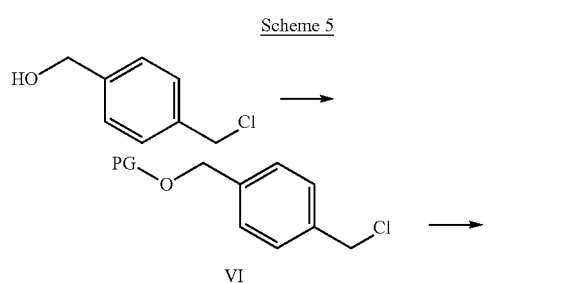

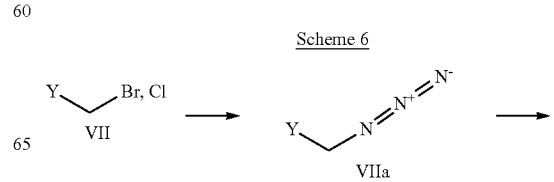

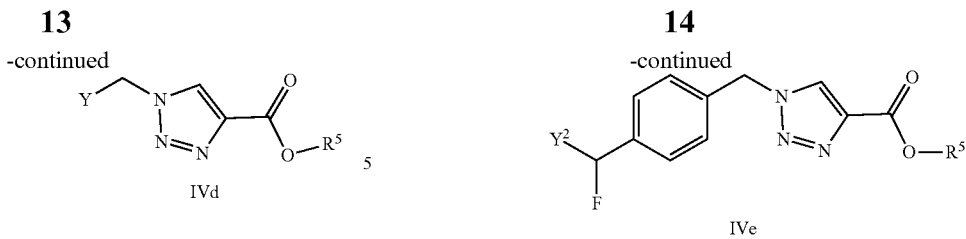

Scheme 6:

Some esters of formula IVd, wherein $R^1$ and $R^2$ denote H, $D^1$ denotes CH, $D^2$ and $D^3$ denote N, Y has the meanings defined hereinbefore, and $R^5$ denotes a cleavable group, can be prepared by the treatment of a corresponding alkyl bromide or chloride of formula VII with sodium azide in N,N-dimethylformamide or another suitable solvent to give an intermediate of formula VIIa which can be reacted with a suitable propiolic acid ester under copper mediated catalytic conditions (e.g. ethyl propiolate, tert-butyl propilate etc with catalytic copper sulfate and sodium ascorbate in water/tert-butanol) to give a triazole intermediate of formula IVd.

Scheme 7:

Some esters of formula IVe, wherein $R^1$ and $R^2$ denote H, $D^1$ denotes CH, $D^2$ and $D^3$ denote N, Y denotes $Y^2$-L-$Y^1$—, wherein $Y^1$ denotes a phenyl ring, L denotes —CH(F)— and $Y^2$ has the meanings defined hereinbefore, and $R^5$ denotes a cleavable group, can be prepared by the treatment of ethyl-4-iodobenzoate with isopropylmagnesium chloride at low temperature (e.g. −50 to −78° C.) under anhydrous conditions in a suitable solvent such as tetrahydrofuran followed by the addition of a suitable aldehyde to give an intermediate of formula VIII. The hydroxyl group can then be converted to a fluorine atom through the use of a fluorinating agent such as bis(2-methoxyethyl)aminosulfur trifluoride to give an intermediate of formula VIIIa. Treatment with a suitable reducing agent (e.g. lithium borohydride, lithium aluminium borohydride, DIBAL etc.) with give an alcohol of formula VIIIb which can then be converted into a suitable leaving group such as a methane sulfonyl ester using methanesulfonyl chloride in the presence of a suitable base (e.g. triethylamine, N.N-diisopropylamine, pyridine etc) to give an intermediate of formula VIIIc which can then be reacted with sodium azide in N,N-dimethylformamide or another suitable solvent to give an intermediate of formula VIIId which can be reacted with a suitable propiolic acid ester under copper mediated catalytic conditions (e.g. ethyl propiolate, tert-butyl propilate etc with catalytic copper sulfate and sodium ascorbate in water/tert-butanol) to give a triazole intermediate of formula IVe.

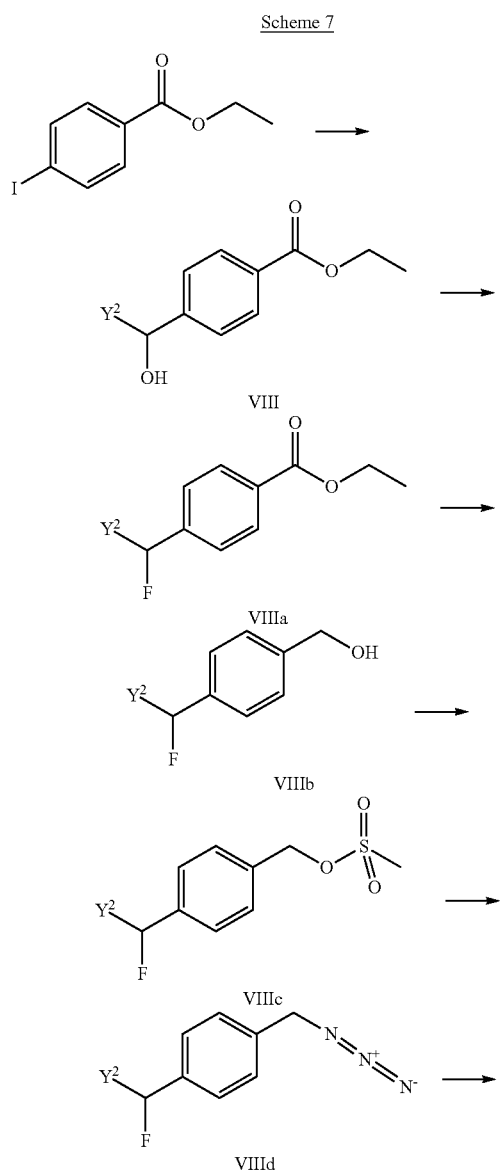

Scheme 7

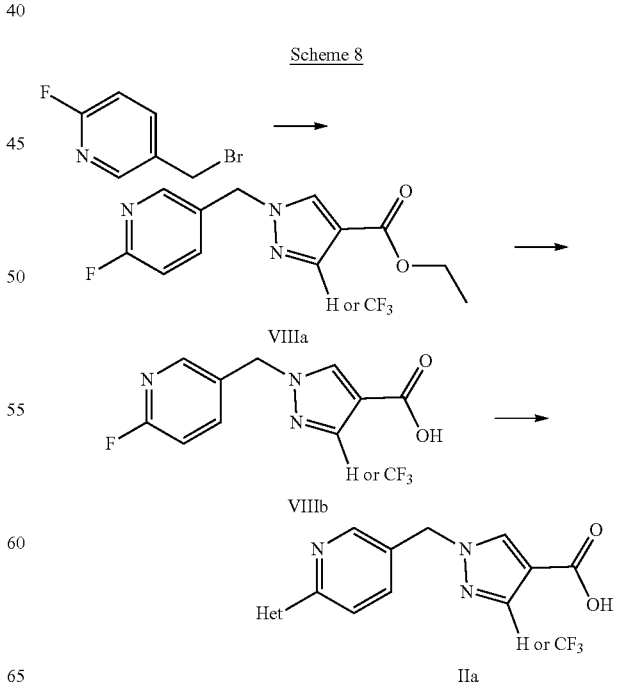

Scheme 8

Scheme 8:

Some acids of formula IIa, wherein $R^1$ and $R^2$ denote H, $D^1$ denotes CH, $D^2$ denotes N, $D^3$ denotes CH or C(CF$_3$), Y denotes $Y^2$-L-$Y^1$—, wherein $Y^1$ denotes a pyridyl ring, L denotes a bond and $Y^2$ (corresponding to Het in formula IIa) denotes a heterocyclic ring as defined hereinbefore, can be prepared by the treatment of 5-bromomethyl-2-fluoropyridine with 1H-pyrazole-4-carboxylic acid ethyl ester or 3-trifluoromethyl-1H-pyrazole-4-carboxylic acid ethyl ester in the presence of a suitable base (e.g. sodium hydride, cesium carbonate, potassium carbonate etc.) in a suitable solvent (e.g. tetrahydrofuran, N,N-dimethylformamide etc.) to give an intermediate of formula VIIIa. Hydrolysis with a suitable hydroxide base (e.g. LiOH, NaOH, KOH) in a suitable solvent (e.g. tetrahydrofuran, methanol, ethanol, 1,4.dioxane, water or a mixture of these etc) gives Intermediated VIIIb. Reaction with a suitable heterocyclic nucleophile in the presence of a suitable base (e.g. sodium hydride, cesium carbonate, potassium carbonate etc.) in a suitable solvent (e.g. tetrahydrofuran, N,N-dimethylformamide etc.) leads to intermediates of formula IIa.

Scheme 9

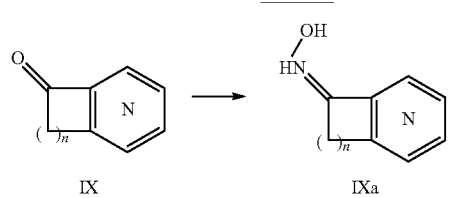

IX          IXa

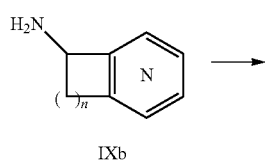

IXb

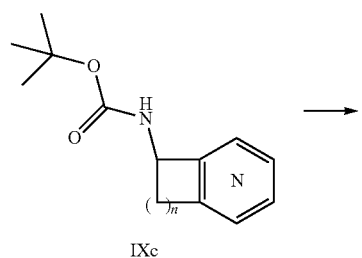

IXc

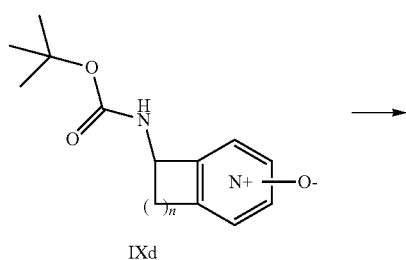

IXd

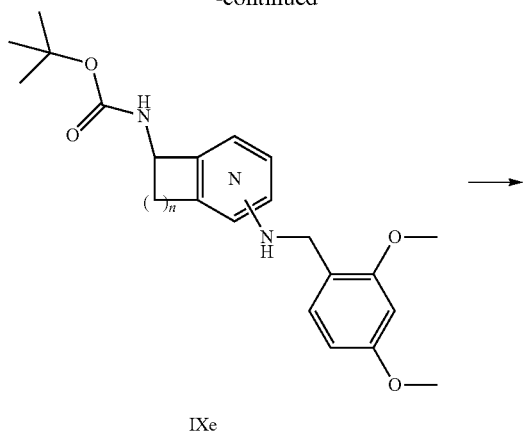

IXe

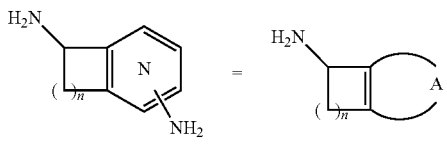

III          III

Scheme 9:

Amines of formula III can be prepared as follows:

A ketone of formula IX, wherein the N-tagged phenyl ring means that one CH ring member is replaced by N, is treated with hydroxylamine in a suitable solvent (e.g. ethanol, methanol, water, tetrahydrofuran or a mixture of these etc.) with heating if necessary to give an oxime of formula IXa. This can then be reduced to an amine of formula IXb by treatment with zinc in an appropriate acid (e.g. acetic acid, dilute hydrochloric acid etc) or by hydrogenation using a suitable catalyst (e.g. Raney Nickel, platinum oxide) under an atmosphere of hydrogen. The resulting amine can be protected as a Boc derivative by treatment with e.g. di-tert-butyl dicarbonate in a suitable solvent (e.g. tetrahydrofuran, methanol, ethanol, water etc or a mixture of these) to give an intermediate of formula IXc. Reaction with a suitable oxidising agent (e.g. 3-chloroperbenzoic acid, oxone, hydrogen peroxide etc.) gives the N-oxide intermediate of formula IXd. This can be reacted with PyBrop in the presence of 2,4-dimethoxybenzylamine to give an intermediate of formula IXe in which the dimethoxybenzylamine moiety is attached to a carbon adjacent to the ring nitrogen. Treatment with acid such as hydrochloric acid, with heating if required removes the protecting groups to give an amine intermediate of formula III.

Scheme 10

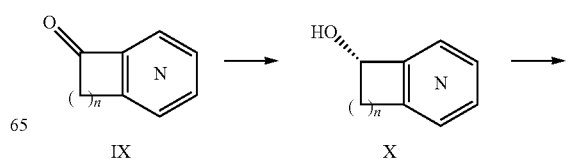

IX          X

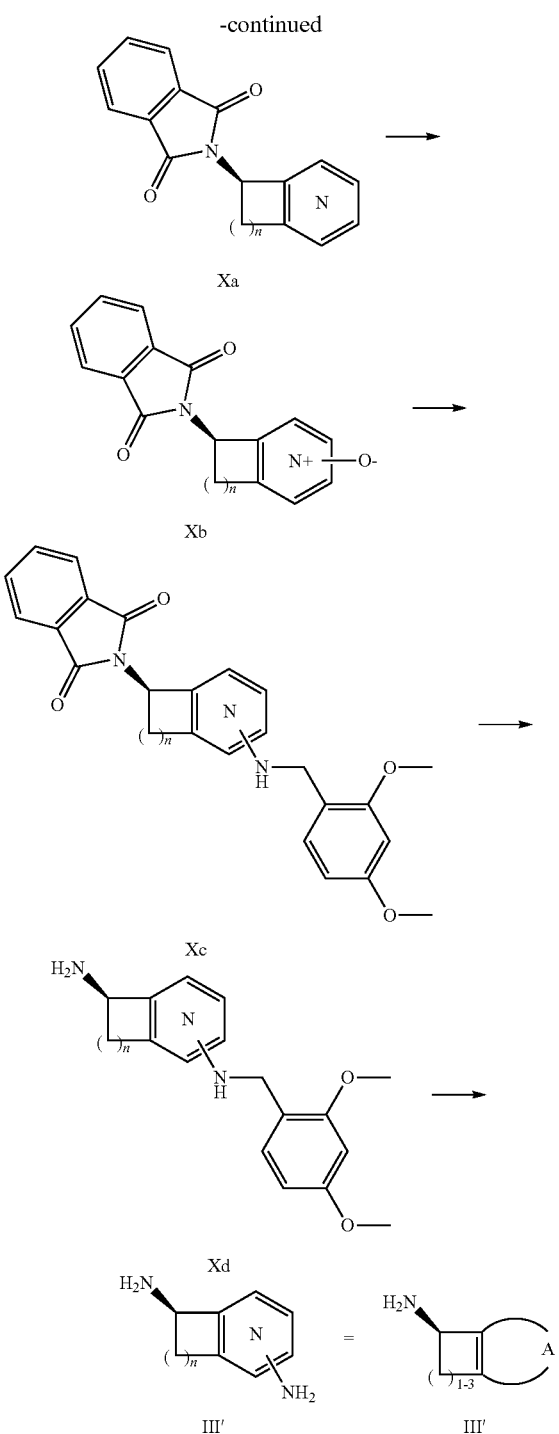

Scheme 10:

Enantiopure amines of formula III' can be prepared as follows:

A ketone of formula IX, wherein the N-tagged phenyl ring means that one CH ring member is replaced by N, is reduced under enantioselective conditions (e.g. those described by Noyori et. al., J. Am. Chem. Soc., 1995, 117 (28), pp 7562-7563) to give a enantiopure alcohol of formula X. This can then be reacted with phthalimide in a Mitsonobu reaction with suitable reagents (e.g. triphenylphosphine plus diethylazodicarboxylate (DEAD) or diisopropyl azodicarboxylate (DIAD) etc.) in a suitable solvent (e.g. tetrahydrofuran, 1,4-dioxane, diethylether etc) leading to the inversion of the stereocenter and an intermediate of formula Xa. Treatment as described in Scheme 9 leads to the intermediate Xc. The phthalimide group can be removed by treatment with e.g. hydrazine or ethanolamine in a suitable solvent (e.g. ethanol, methanol, tetrahydrofuran, water etc or a mixture of these) with heating if necessary to give an intermediate of formula Xd. Treatment with acid such as hydrochloric acid, with heating if required removes the protecting group to give a chiral amine intermediate of formula III'.

The compounds of general formula I may be resolved into their enantiomers and/or diastereomers as mentioned below. Thus, for example, cis/trans mixtures may be resolved into their cis and trans isomers and racemic compounds may be separated into their enantiomers.

The cis/trans mixtures may be resolved, for example, by chromatography into the cis and trans isomers thereof. The compounds of general formula I which occur as racemates may be separated by methods known per se into their optical antipodes and diastereomeric mixtures of compounds of general formula I may be resolved into their diastereomers by taking advantage of their different physico-chemical properties using methods known per se, e.g. chromatography and/or fractional crystallization; if the compounds obtained thereafter are racemates, they may be resolved into the enantiomers as mentioned below.

The racemates are preferably resolved by column chromatography on chiral phases or by crystallization from an optically active solvent or by reacting with an optically active substance which forms salts or derivatives such as esters or amides with the racemic compound. Salts may be formed with enantiomerically pure acids for basic compounds and with enantiomerically pure bases for acidic compounds. Diastereomeric derivatives are formed with enantiomerically pure auxiliary compounds, e.g. acids, their activated derivatives, or alcohols. Separation of the diastereomeric mixture of salts or derivatives thus obtained may be achieved by taking advantage of their different physico-chemical properties, e.g. differences in solubility; the free antipodes may be released from the pure diastereomeric salts or derivatives by the action of suitable agents. Optically active acids commonly used for such a purpose as well as optically active alcohols applicable as auxiliary residues are known to those skilled in the art.

As mentioned above, the compounds of formula I may be converted into salts, particularly for pharmaceutical use into the pharmaceutically acceptable salts. As used herein, "pharmaceutically acceptable salts" refer to derivatives of the disclosed compounds wherein the parent compound is modified by making acid or base salts thereof.

The compounds according to the invention are advantageously also obtainable using the methods described in the examples that follow, which may also be combined for this purpose with methods known to the skilled man from the literature.

Terms and Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

The terms "compound(s) according to this invention", "compound(s) of formula (I)", "compound(s) of the invention" and the like denote the compounds of the formula (I) according to the present invention including their tautomers, stereoisomers and mixtures thereof and the salts thereof, in particular the pharmaceutically acceptable salts thereof, and the solvates and hydrates of such compounds, including the solvates and hydrates of such tautomers, stereoisomers and salts thereof.

The terms "treatment" and "treating" embrace both preventative, i.e. prophylactic, or therapeutic, i.e. curative and/or palliative, treatment. Thus the terms "treatment" and "treating" comprise therapeutic treatment of patients having already developed said condition, in particular in manifest form. Therapeutic treatment may be symptomatic treatment in order to relieve the symptoms of the specific indication or causal treatment in order to reverse or partially reverse the conditions of the indication or to stop or slow down progression of the disease. Thus the compositions and methods of the present invention may be used for instance as therapeutic treatment over a period of time as well as for chronic therapy. In addition the terms "treatment" and "treating" comprise prophylactic treatment, i.e. a treatment of patients at risk to develop a condition mentioned hereinbefore, thus reducing said risk.

When this invention refers to patients requiring treatment, it relates primarily to treatment in mammals, in particular humans.

The term "therapeutically effective amount" means an amount of a compound of the present invention that (i) treats or prevents the particular disease or condition, (ii) attenuates, ameliorates, or eliminates one or more symptoms of the particular disease or condition, or (iii) prevents or delays the onset of one or more symptoms of the particular disease or condition described herein.

The term "substituted" as used herein, means that any one or more hydrogens on the designated atom, radical or moiety is replaced with a selection from the indicated group, provided that the atom's normal valence is not exceeded, and that the substitution results in an acceptably stable compound.

In the groups, radicals, or moieties defined below, the number of carbon atoms is often specified preceding the group, for example, $C_{1-6}$-alkyl means an alkyl group or radical having 1 to 6 carbon atoms. In general, for groups comprising two or more subgroups, the last named subgroup is the radical attachment point, for example, the substituent "aryl-$C_{1-3}$-alkyl-" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail.

An asterisk may be used in sub-formulas to indicate the bond which is connected to the core molecule as defined.

The numeration of the atoms of a substituent starts with the atom which is closest to the core or to the group to which the substituent is attached.

For example, the term "3-carboxypropyl-group" represents the following substituent:

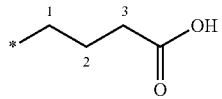

wherein the carboxy group is attached to the third carbon atom of the propyl group. The terms "1-methylpropyl-", "2,2-dimethylpropyl-" or "cyclopropylmethyl-" group represent the following groups:

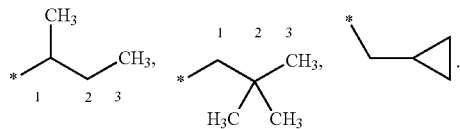

The asterisk may be used in sub-formulas to indicate the bond which is connected to the core molecule as defined.

In a definition of a group the term "wherein each X, Y and Z group is optionally substituted with" and the like denotes that each group X, each group Y and each group Z either each as a separate group or each as part of a composed group may be substituted as defined. For example a definition "$R^{ex}$ denotes H, $C_{1-3}$-alkyl, $C_{3-6}$-cycloalkyl, $C_{3-6}$-cycloalkyl-$C_{1-3}$-alkyl or $C_{1-3}$-alkyl-O—, wherein each alkyl group is optionally substituted with one or more $L^{ex}$." or the like means that in each of the beforementioned groups which comprise the term alkyl, i.e. in each of the groups $C_{1-3}$-alkyl, $C_{3-6}$-cycloalkyl-$C_{1-3}$-alkyl and $C_{1-3}$-alkyl-O—, the alkyl moiety may be substituted with $L^{ex}$ as defined.

Unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof.

Salts of other acids than those mentioned above which for example are useful for purifying or isolating the compounds of the present invention (e.g. trifluoro acetate salts) also comprise a part of the invention.

The term halogen generally denotes fluorine, chlorine, bromine and iodine.

The term "$C_{1-n}$-alkyl", wherein n is an integer from 1 to n, either alone or in combination with another radical denotes an acyclic, saturated, branched or linear hydrocarbon radical with 1 to n C atoms. For example the term $C_{1-5}$-alkyl embraces the radicals $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$— and $H_3C$—$CH_2$—$CH(CH_2CH_3)$—.

Many of the terms given above may be used repeatedly in the definition of a formula or group and in each case have one of the meanings given above, independently of one another.

Pharmacological Activity

The activity of the compounds of the invention may be demonstrated using the following assays:

Biological Methods

The ability of compounds of Formula I to inhibit plasma kallikrein (KLKB1), Factor XIIa (FXIIa), Factor XIa (FXIa), Factor Xa (FXa), Factor IIa (alpha-thrombin; FIIa), plasmin, trypsin, tissue kallikrein 1 (KLK1), Factor VIIa (FVIIa), or FVIIa complexed with Tissue Factor, phospholipids and $CaCl_2$ (FVIIa/TF/PL/$CaCl_2$) was determined using the following biochemical assays in assay buffer (100 mM Tris, 150 mM NaCL, adjusted to a pH of 7.8 with HCl, and containing 0.1% (w/v) BSA and 0.05% (v/v) Tween20) in the presence of 1% (v/v) DMSO:

Evaluation of the Inhibition of KLKB1 Using an Endpoint Assay

Human KLKB1 (0.01 U/mL; Enzyme Research Laboratories) or rat KLKB1 (0.625 nM; produced in-house) was incubated for 1 hr at Room Temperature with 0.10 µM fluorogenic substrate H-Pro-Phe-Arg-AMC (11295 from Bachem) and various concentrations of the test compound in assay buffer. Subsequently, PPACK II (Calbiochem) was added as a stop solution to achieve a final concentration of 1 µM and fluorescence was measured using an Envision Reader (PerkinElmer) with the wavelength excitation setting of 355 nm and the wavelength emission setting of 460 nm.

Evaluation of the Inhibition of Human KLKB1 in Dextransulfat Activated Human PPP.

Platelet poor plasma (PPP) obtained from human wholeblood, anticoagulated with EDTA, was activated with 12.5 µg/mL dextransulfate for 7 min on ice. The activated PPP was incubated with various concentrations of the test compound in assay buffer. Afterwards the mixture was incubated at 24° C. with 0.25 mM fluorogenic substrate H-Pro-Phe-Arg-AMC (11295 from Bachem) and measurements were performed in a kinetic interval every $2^{nd}$ minute for 16 min using a Spectramax M5 (Molecular Devices) with the following settings of the wavelength excitation of 350 nm and wavelength emission of 450 nm.

Evaluation of the Inhibition of KLKB1 ($K_i$)

Human KLKB1 (1.78 nM or 0.025 U/mL; Enzyme Research Laboratories) was incubated at 24° C. with 0.25 mM fluorogenic substrate H-Pro-Phe-Arg-AMC (11295 from Bachem) and various concentrations of the test compound in assay buffer. Measurements were performed in a kinetic interval every $2^{nd}$ minute for 16 min using a Spectramax M5 (Molecular Devices) with the following settings of the wavelength excitation of 350 nm and wavelength emission of 450 nm.

Evaluation of the Inhibition of FXIIa ($K_i$)

Human FXIIa (47.5 nM or 1.1 U/mL; Enzyme Research Laboratories) was incubated at 24° C. with 0.5 mM chromogenic Substrate S2302 (Chromogenix) and various concentrations of the test compound in assay buffer. Measurements were performed in a kinetic interval every $2^{nd}$ minute for 16 min using a Spectramax M5 (Molecular Devices) measuring the optical absorbance at 405 nm.

Evaluation of the Inhibition of FXIa ($K_i$)

Human FXIa (0.5 nM or 0.016 U/mL; Enzyme Research Laboratories) was incubated at 24° C. with 0.25 mM fluorogenic substrate Boc-Glu(OBzl)-Ala-Arg-AMC.HCl (11575 from Bachem) and various concentrations of the test compound in assay buffer. Measurements were performed in a kinetic interval every $2^{nd}$ minute for 16 min using a Spectramax M5 (Molecular Devices) with the following settings of the wavelength excitation of 350 nm and wavelength emission of 450 nm.

Evaluation of the Inhibition of FXa ($K_i$)

Human FXa (0.86 nM or 0.01 U/mL; Enzyme Research Laboratories) was incubated at 24° C. with 0.5 mM chromogenic Substrate S2765 (Chromogenix) and various concentrations of the test compound in assay buffer. Measurements were performed in a kinetic interval every $2^{nd}$ minute for 16 min using a Spectramax M5 (Molecular Devices) measuring the optical absorbance at 405 nm.

Evaluation of the Inhibition of FIIa ($K_i$)

Human FIIa (44.6 nM or 5 U/mL; Enzyme Research Laboratories) was incubated at 24° C. with 0.5 mM chromogenic Substrate S2238 (Chromogenix) and various concentrations of the test compound in assay buffer. Measurements were performed in a kinetic interval every $2^{nd}$ minute for 16 min using a Spectramax M5 (Molecular Devices) measuring the optical absorbance at 405 nm.

Evaluation of the Inhibition of Plasmin ($K_i$)

Human plasmin (64.1 nM or 0.0275 U/mL; Enzyme Research Laboratories) was incubated at 24° C. with 0.3 mM chromogenic Substrate S2251 (Chromogenix) and various concentrations of the test compound in assay buffer. Measurements were performed in a kinetic interval every $2^{nd}$ minute for 16 min using a Spectramax M5 (Molecular Devices) measuring the optical absorbance at 405 nm.

Evaluation of the Inhibition of Trypsin ($K_i$)

Human trypsin (4.54 nM or 250 U/mL; Calbiochem) was incubated at 24° C. with 0.5 mM chromogenic Substrate S2222 (Chromogenix) and various concentrations of the test compound in assay buffer. Measurements were performed in a kinetic interval every $2^{nd}$ minute for 16 min using a Spectramax M5 (Molecular Devices) measuring the optical absorbance at 405 nm.

Evaluation of the Inhibition of KLK1 ($K_i$)

Prior to the assay, human KLK1 (R&D Systems) was activated by incubation with human trypsin (Calbiochem) in a 1:10,000 ratio for 15 min at 37° C. For assaying KLK1 inhibitory activity, activated KLK1 (31.25 nM or 1 U/mL) was incubated at 24° C. with 0.1 mM fluorogenic substrate H-Pro-Phe-Arg-AMC (11295 from Bachem) and various concentrations of the test compound in assay buffer. Measurements were performed in a kinetic interval every $2^{nd}$ minute for 16 min using a Spectramax M5 (Molecular Devices) with the following settings of the wavelength excitation of 350 nm and wavelength emission of 450 nm.

Evaluation of the Inhibition of FVIIa ($K_i$)

Human FVIIa (0.86 nM or 0.01 U/mL; Enzyme Research Laboratories) was incubated at 24° C. with 1.5 mM chromogenic Pefachrome® FVIIa (Loxo) and various concentrations of the test compound in assay buffer. Measurements were performed in a kinetic interval every $2^{nd}$ minute for 16 min using a Spectramax M5 (Molecular Devices) measuring the optical absorbance at 405 nm.

Evaluation of the Inhibition of FVIIa/TF/PL/$CaCl_2$ ($K_i$)

Human FVIIa (300 nM or 585 U/mL; Enzyme Research Laboratories) together with mM $CaCl_2*2H_2O$ and 13.3% (v/v) Dade® Innovin® (Siemens; OQUMI94E0002(5534), which contains recombinant human tissue factor synthetic phospholipids (thromboplastin), was incubated at 24° C. with 1.5 mM chromogenic Pefachrome® FVIIa (Loxo) and various concentrations of the test compound in assay buffer. Measurements were performed in a kinetic interval every $2^{nd}$ minute for 16 min using a Spectramax M5 (Molecular Devices) measuring the optical absorbance at 405 nm.

Calculation of pIC$_{50}$ and pK$_i$ Values

The average V$_{max}$ values for the time interval from 2 to 12 min after initiation of the assay (expressed as either delta OD/min for assays using a chromogenic substrate or delta RFU/min for assays using a fluorigenic substrate, respectively) were plotted versus the Log of the concentration in molar of the evaluated inhibitor compound. The pIC$_{50}$ values were then fitted using a four-parametric fitting procedure using using GraphPad Prism (version 6; GraphPad Software, Inc.). Respective K values were obtained by correction of the IC$_{50}$ values for the respective K$_M$ value of the used substrate (see Table X for the obtained K$_M$ values of the used substrates) using the following formula:

$$K_i = \frac{IC_{50}}{1 + \frac{[Substrate, mM]}{K_M}}$$

Where the IC$_{50}$ is in molar and the K$_M$ value in mM.

TABLE X

K$_M$ values obtained for the substrates used in the enzymatic assays.

| Enzyme | Substrate | K$_M$ (mM) |
|---|---|---|
| KLKB1 | I1295 | 0.16 |
| FXIIa | S2302 | 0.20 |
| FXIa | I1575 | 0.29 |
| FXa | S2765 | 1.31 |
| FIIa | S2238 | 1.25 |
| Plasmin | S2251 | 1.45 |
| Trypsin | S2222 | 2.03 |
| KLK1 | I1295 | 0.07 |
| FVIIa | Pefachrome ® FVIIa | 0.42 |
| FVIIa/TF/PL/CaCl$_2$ | Pefachrome ® FVIIa | 3.92 |

Evaluation of Permeability

Caco-2 cells (1-2×10$^5$ cells/1 cm$^2$ area) are seeded on filter inserts (Costar transwell polycarbonate or PET filters, 0.4 µm pore size) and cultured (DMEM) for 10 to 25 days.

Compounds are dissolved in appropriate solvent (like DMSO, 1–20 mM stock solutions). Stock solutions are diluted with HTP-4 buffer (128.13 mM NaCl, 5.36 mM KCl, 1 mM MgSO$_4$, 1.8 mM CaCl$_2$, 4.17 mM NaHCO$_3$, 1.19 mM Na$_2$HPO$_4$×7H$_2$O, 0.41 mM NaH$_2$PO$_4$×H$_2$O, 15 mM HEPES, 20 mM glucose, pH 7.2) to prepare the transport solutions (0.1-300 µM compound, final DMSO<=0.5%). The transport solution (TL) is applied to the apical or basolateral donor side for measuring A-B or B-A permeability (3 filter replicates), respectively. The receiver side contains HTP-4 buffer supplemented with 2% BSA. Samples are collected at the start and end of experiment from the donor and at various time intervals for up to 2 hours also from the receiver side for concentration measurement by HPLC-MS/MS or scintillation counting. Sampled receiver volumes are replaced with fresh receiver solution.

Evaluation of Metabolic Stability in Human or Rat Liver Microsomes

The metabolic degradation of the test compound is assayed at 37° C. with pooled human or rat liver microsomes. The final incubation volume of 100 µl per time point contains TRIS buffer pH 7.6 at RT (0.1 M), magnesium chloride (5 mM), microsomal protein (1 mg/ml) and the test compound at a final concentration of 1 µM.

Following a short preincubation period at 37° C., the reactions were initiated by addition of beta-nicotinamide adenine dinucleotide phosphate, reduced form (NADPH, 1 mM) and terminated by transferring an aliquot into solvent after different time points. Additionally, the NADPH-independent degradation was monitored in incubations without NADPH, terminated at the last time point. The quenched incubations are pelleted by centrifugation (10000 g, 5 min). An aliquot of the supernatant is assayed by LC-MS/MS for the amount of parent compound. The half-life (t1/2 INVITRO) is determined by the slope of the semilogarithmic plot of the concentration-time profile.

Evaluation of Metabolic Stability in Human or Rat Hepatocytes

The metabolic degradation of the test compound is assayed in a hepatocyte suspension. Hepatocytes (typically cryopreserved) are incubated in an appropriate buffer system (e.g. Dulbecco's modified eagle medium plus 3.5 µg glucagon/500 mL, 2.5 mg insulin/500 mL and 3.75 mg/500 mL hydrocortison) containing 5% species serum.

Following a (typically) 30 min preincubation in an incubator (37° C., 10% CO$_2$) 5 µl of test compound solution (80 µM; from 2 mM in DMSO stock solution diluted 1:25 with medium) are added into 395 µl hepatocyte suspension (cell density in the range 0.25-5 Mio cells/mL, typically 1 Mio cells/mL; final concentration of test compound 1 µM, final DMSO concentration 0.05%).

The cells are incubated for six hours (incubator, orbital shaker) and samples (25 µl) are taken at 0, 0.5, 1, 2, 4 and 6 hours. Samples are transferred into acetonitrile and pelleted by centrifugation (5 min). The supernatant is transferred to a new 96-deepwell plate, evaporated under nitrogen and resuspended.

Decline of parent compound is analyzed by HPLC-MS/MS CLint is calculated as follows CL_INTRINSIC=Dose/AUC=(C0/CD)/(AUD+clast/k)×1000/60. C0: initial concentration in the incubation [µM], CD: cell density of vital cells [10e6 cells/mL], AUD: area under the data [µM×h], clast: concentration of last data point [µM], k: slope of the regression line for parent decline [h-1].

Evaluation of Plasma Protein Binding.

This equilibrium dialysis (ED) technique is used to determine the approximate in vitro fractional binding of test compounds to plasma proteins. Dianorm Teflon dialysis cells (micro 0.2) are used. Each cell consists of a donor and an acceptor chamber, separated by an ultrathin semipermeable membrane with a 5 kDa molecular weight cutoff. Stock solutions for each test compound are prepared in DMSO at 1 mM and diluted to a final concentration of 1.0 µM. The subsequent dialysis solutions are prepared in pooled human or rat plasma (with NaEDTA) from male and female donors. Aliquots of 200 µL dialysis buffer (100 mM potassium phosphate, pH 7.4) are dispensed into the buffer chamber. Aliquots of 200 µL test compound dialysis solution are dispensed into the plasma chambers. Incubation is carried out for 2 hours under rotation at 37° C.

At the end of the dialysis period, the dialysate is transferred into reaction tubes. The tubes for the buffer fraction contain 0.2 ml Acetonitril/water (80/20). Aliquots of 25 µL of the plasma dialysate are transferred into deep well plates and mixed with 25 µl Acetonitril/water (80/20), 25 µl buffer, 25 µL calibration solution and 25 µl Internal Standard solution. Protein prezipitation is done by adding 200 µl Acetonitrile.

Aliquots of 50 µl of the buffer dialysate are transferred into deep well plates and mixed with 25 µl blank plasma, 25 µl Internal Standard solution and 200 µl Acetonitrile.

Samples are measured on HPLC-MS/MS-Systems and evaluated with Analyst-Software.

Percent bound is calculated with the formula:% bound=(plasma concentration−buffer concentration/plasma concentration)×100

Evaluation of Solubility

The aqueous solubility of the test compound is determined by comparing the amount dissolved in buffer to the amount in an acetonitrile/water (1/1) solution. Starting from a 10 mM DMSO stock solution aliquots are diluted with acetonitril/water (1/1) or buffer resp. After 24 h of shaking, the solutions are filtrated and analyzed by LC-UV. The amount dissolved in buffer is compared to the amount in the acetonitrile solution. Solubility will usually be measured from 0.001 to 0.125 mg/ml at a DMSO concentration of 2.5%. If more than 90% of the compound is dissolved in buffer, the value is marked with ">".

Evaluation of Pharmacokinetic Characteristics in Rodents

The test compound is administered either intravenously to fed rats or orally to fasted rats. Blood samples are taken at several time points post application of the test compound, anticoagulated and centrifuged.

The concentration of analytes—the administered compound and/or metabolites—are quantified in the plasma samples.

PK parameters are calculated using non compartment methods. AUC and Cmax are normalized to a dose of 1 µmol/kg.

Biological Activity:

The inhibitory activity of compounds of the invention is demonstrated by the data in Table XX. The $IC_{50}$ values were obtained with the aid of the inhibition of KLKB1 endpoint assay described above.

TABLE XX $IC_{50}$ measurements for the inhibition of human Plasma Kallikrein (KLKB1)

| Example | $IC_{50}$ (nM) |
|---|---|
| 1 | 900 |
| 2 | 600 |
| 3 | 5500 |
| 4 | 790 |
| 5 | 9 |
| 6 | 32 |
| 7 | 910 |
| 8 | 4 |
| 9 | 560 |
| 11 | 1900 |
| 12 | 36 |
| 13 | 19 |
| 14 | 40 |
| 15 | 1 |
| 16 | 18 |

Accordingly, the present invention relates to a compound of general formula I as a medicament.

Furthermore, the present invention relates to the use of a compound of general formula I or a pharmaceutical composition according to this invention for the treatment and/or prevention of diseases or conditions which are mediated by unwanted plasma kallikrein activity in a patient, preferably in a human.

In yet another aspect the present invention relates to a method for treating a disease or condition mediated by unwanted plasma kallikrein activity in a mammal that includes the step of administering to a patient, preferably a human, in need of such treatment a therapeutically effective amount of a compound or a pharmaceutical composition of the present invention.

Diseases and conditions mediated by unwanted plasma kallikrein activity embrace diabetic complications, diabetic retinopathy, proliferative and non-proliferative retinopathy, diabetic macular edema (DME), clinically significant macular edema (CSME), cystoid macular edema (CME), CME following cataract extraction, CME induced by cryotherapy, CME induced by uveitis, endophthalmitis, CME following vascular occlusion (e.g. central retinal vein occlusion, branch retinal vein occlusion, or hemiretinal vein occlusion), retinal edema, complications related to cataract surgery in diabetic retinopathy, hypertensive retinopathy, retinal trauma, dry and wet aged-related macular degeneration (AMD), polypoidal choroidal vasculopathy (PCV), hereditary angioedema and acute respiratory distress syndrome (ARDS).

According to one aspect the compounds and pharmaceutical compositions of the present invention are particularly suitable for treating ocular diseases including diabetic retinopathy, proliferative and non-proliferative retinopathy, diabetic macular edema (DME), retinal vein occlusion, aged-related macular degeneration (AMD), polypoidal choroidal vasculopathy (PCV) as well as hereditary angioedema.

Therefore according to another aspect the invention relates to compounds of formula I and pharmaceutical compositions according to the invention for use in ophthalmic indications such as diabetic retinopathy, proliferative and non-proliferative retinopathy, diabetic macular edema (DME), age-related macular degeneration (AMD and polypoidal choroidal vasculopathy (PCV).

In addition the compounds and pharmaceutical compositions according to the invention are suitable for use in one or more of the following therapeutic processes: Treatment of edema, particularly hereditary angioedema.

In particular, the compounds and pharmaceutical compositions according to the invention are suitable for the treatment of diabetic retinopathy, proliferative and non-proliferative retinopathy, diabetic macular edema (DME), age-related macular degeneration (AMD and polypoidal choroidal vasculopathy (PCV).

The compounds according to the invention are most particularly suitable for treating diabetic retinopathy, proliferative and non-proliferative retinopathy, diabetic macular edema (DME)

The dose range of the compounds of general formula I applicable per day is usually from 0.01 to 10 mg per kg body weight The actual therapeutically effective amount or therapeutic dosage will of course depend on factors known by those skilled in the art such as age and weight of the patient, route of administration and severity of disease. In any case the compound or composition will be administered at dosages and in a manner which allows a therapeutically effective amount to be delivered based upon patient's unique condition.

The compounds, compositions, including any combinations with one or more additional therapeutic agents, according to the invention may be administered by oral, intravitreal, transdermal, inhalative, parenteral or sublingual route. Of the possible methods of administration, oral or intravitreal administration is preferred. In case of intravitreal injection the preferred dose should not exceed 5 mg per eye.

Pharmaceutical Compositions

Suitable preparations for administering the compounds of formula I, optionally in combination with one or more further therapeutic agents, will be apparent to those with ordinary skill in the art and include for example tablets, pills, capsules, suppositories, lozenges, troches, solutions, syrups, elixirs, sachets, injectables, inhalatives and powders etc. Oral formulations, particularly solid forms such as e.g. tablets or capsules are preferred. For intravitreal injection, solutions are preferred. The content of the pharmaceutically active compound(s) is advantageously in the range from 0.1 to 90 wt.-%, for example from 1 to 70 wt.-% of the composition as a whole.

Suitable tablets may be obtained, for example, by mixing one or more compounds according to formula I with known excipients, for example inert diluents, carriers, disintegrants, adjuvants, surfactants, binders and/or lubricants. The tablets may also consist of several layers. The particular excipients, carriers and/or diluents that are suitable for the desired preparations will be familiar to the skilled man on the basis of his specialist knowledge. The preferred ones are those that are suitable for the particular formulation and method of administration that are desired. The preparations or formulations according to the invention may be prepared using methods known per se that are familiar to the skilled man, such as for example by mixing or combining at least one compound of formula I according to the invention, or a pharmaceutically acceptable salt of such a compound, and one or more excipients, carriers and/or diluents.

Combination Therapy

The compounds of the invention may further be combined with one or more, preferably one additional therapeutic agent. According to one embodiment the additional therapeutic agent is selected from the group of therapeutic agents useful in the treatment of diseases or conditions described hereinbefore, in particular associated with metabolic diseases or conditions such as for example diabetes mellitus, obesity, diabetic complications, hypertension, hyperlipidemia, or therapeutic agents useful for the treatment of ocular diseases. Additional therapeutic agents which are suitable for such combinations include in particular those which for example potentiate the therapeutic effect of one or more active substances with respect to one of the indications mentioned and/or which allow the dosage of one or more active substances to be reduced.

Therefore a compound of the invention may be combined with one or more additional therapeutic agents selected from the group consisting of antidiabetic agents, agents for the treatment of overweight and/or obesity, agents for the treatment of high blood pressure, heart failure and/or atherosclerosis and agents for the treatment of ocular diseases.

Antidiabetic agents are for example metformin, sulphonylureas, nateglinide, repaglinide, thiazolidinediones, PPAR-(alpha, gamma or alpha/gamma) agonists or modulators, alpha-glucosidase inhibitors, DPPIV inhibitors, SGLT2-inhibitors, insulin and insulin analogues, GLP-1 and GLP-1 analogues or amylin and amylin analogues, cycloset, 11β-HSD inhibitors. Other suitable combination partners are inhibitors of protein tyrosinephosphatase 1, substances that affect deregulated glucose production in the liver, such as e.g. inhibitors of glucose-6-phosphatase, or fructose-1,6-bisphosphatase, glycogen phosphorylase, glucagon receptor antagonists and inhibitors of phosphoenol pyruvate carboxykinase, glycogen synthase kinase or pyruvate dehydrokinase, alpha2-antagonists, CCR-2 antagonists or glucokinase activators. One or more lipid lowering agents are also suitable as combination partners, such as for example HMG-CoA-reductase inhibitors, fibrates, nicotinic acid and the derivatives thereof, PPAR-(alpha, gamma or alpha/gamma) agonists or modulators, PPAR-delta agonists, ACAT inhibitors or cholesterol absorption inhibitors such as, bile acid-binding substances such as, inhibitors of ileac bile acid transport, MTP inhibitors, or HDL-raising compounds such as CETP inhibitors or ABC1 regulators.

Therapeutic agents for the treatment of overweight and/or obesity are for example antagonists of the cannabinoid1 receptor, MCH-1 receptor antagonists, MC4 receptor agonists, NPY5 or NPY2 antagonists, β3-agonists, leptin or leptin mimetics, agonists of the 5HT2c receptor.

Therapeutic agents for the treatment of high blood pressure, chronic heart failure and/or atherosclerosis are for example A-II antagonists or ACE inhibitors, ECE inhibitors, diuretics, β-blockers, Ca-antagonists, centrally acting antihypertensives, antagonists of the alpha-2-adrenergic receptor, inhibitors of neutral endopeptidase, thrombocyte aggregation inhibitors and others or combinations thereof are suitable. Angiotensin II receptor antagonists are preferably used for the treatment or prevention of high blood pressure and complications of diabetes, often combined with a diuretic such as hydrochlorothiazide.

Therapeutic agents for the treatment of ocular diseases may include for example intravitreally administered corticosteroids, intravitreally administered anti-VEGF therapy, anti-Ang2 inhibitors, dual anti-VEGF/anti-Ang2 inhibitors, anti PDGF, dual anti-VEGF/anti-PDGF, VAP-1 (AOC3) inhibitors, Complement inhibitors (e.g. Complement factors 3, 5, B, and D inhibitors), Bradykinin receptor 1 antagonists, and CCR-2 antagonists.

Additional treatments for ocular diseases may include laser coagulation therapy.

The dosage for the combination partners mentioned above is usually ⅕ of the lowest dose normally recommended up to 1/1 of the normally recommended dose.

Preferably, compounds of the present invention and/or pharmaceutical compositions comprising a compound of the present invention optionally in combination with one or more additional therapeutic agents are administered in conjunction with exercise and/or a diet.

Therefore, in another aspect, this invention relates to the use of a compound according to the invention in combination with one or more additional therapeutic agents described hereinbefore and hereinafter for the treatment of diseases or conditions which may be affected or which are mediated by unwanted plasma kallikrein activity, in particular diseases or conditions as described hereinbefore and hereinafter.

In yet another aspect the present invention relates a method for treating a disease or condition mediated by unwanted plasma kallikrein activity in a patient that includes the step of administering to the patient, preferably a human, in need of such treatment a therapeutically effective amount of a compound of the present invention in combination with a therapeutically effective amount of one or more additional therapeutic agents described in hereinbefore and hereinafter, The use of the compound according to the invention in combination with the additional therapeutic agent may take place simultaneously or at staggered times.

The compound according to the invention and the one or more additional therapeutic agents may both be present together in one formulation, for example a tablet or capsule, or separately in two identical or different formulations, for example as a so-called kit-of-parts.

Consequently, in another aspect, this invention relates to a pharmaceutical composition which comprises a compound according to the invention and one or more additional therapeutic agents described hereinbefore and hereinafter, optionally together with one or more inert carriers and/or diluents.

Other features and advantages of the present invention will become apparent from the following more detailed Examples which illustrate, by way of example, the principles of the invention.

Examples/Preliminary Remarks:

The terms "ambient temperature" and "room temperature" are used interchangeably and designate a temperature of about 20° C., e.g. 15 to 25° C.

As a rule, $^1$H-NMR and/or mass spectra have been obtained for the compounds prepared.

Unless otherwise specified, compounds containing chiral centers have the stereochemistry depicted. The assignment of stereochemistry has been made either by use of use of a chiral starting material of known stereochemistry or by stereoselective synthesis of known stereochemistry.

Abbreviations

Ac acetyl
ACN acetonitrile
APCI atmospheric pressure chemical ionization
Boc tert-butyloxycarbonyl
CU 1,1'-carbonyldiimidazole
d day
dba dibenzylideneacetone
DCM dichloromethane
DIPEA N,N-diisopropylethylamine
DME 1,2-dimethoxyethane
DMF N,N-dimethylformamide
DMSO dimethyl sulfoxide
dppf 1,1'-Bis(diphenylphosphino)ferrocene
ESI electrospray ionization (in MS)
EtOAc ethylacetate
EtOH ethanol
Ex. example
h hour(s)
HATU O-(7-azabenzotriazol-1-yl)-N,N,N',N'-tetramethyl-uronium-hexafluorophosphate
HPLC high performance liquid chromatography
HPLC-MS coupled high performance liquid chromatography-mass spectrometry
LC liquid chromatography
LC-MS coupled liquid chromatography-mass spectrometry
M molar (mol/L)
MeOH methanol
min minute(s)
MS mass spectrometry
NMP 1-methyl-2-pyrrolidinone
PyBop (benzotriazol-1-yloxy)tripyrrolidinophosphonium hexafluorophosphate
PyBrop bromotripyrrolidinophosphonium hexafluorophosphate
RP reverse phase
rt room temperature
$t_R$ retention time (in HPLC/LC)
TBTU O-(benzotriazol-1-yl)-N,N,N',N'-tetramethyluronium tetrafluoroborate
TEA triethylamine
TFA trifluoroacetic acid
THF tetrahydrofuran
TLC thin-layer chromatography
UPLC-MS ultra performance liquid chromatography-mass spectrometry Analytical Methods UPLC-MS and HPLC-MS Methods:

Method 1
Instrument: LC/MS Waters Acquity UPLC System DAD, SQD single quadrupole
Column: BEH C18 1.7 μm 2.1×50 mm, Temp 35° C.
Mobile phase: A=H$_2$O 90%+CH$_3$CN 10%+NH$_4$COOH 5 mM
B=CH$_3$CN 90%+H$_2$O 10%

| Time in min | % A | % B | flow rate in mL/min |
|---|---|---|---|
| 0.00 | 100 | 0 | 0.70 |
| 1.20 | 0 | 100 | 0.70 |
| 1.45 | 0 | 100 | 0.70 |
| 1.55 | 100 | 0 | 0.70 |
| 1.75 | 100 | 0 | 0.70 |

Detection: UV 254 nm
Detection: SQD, single quadrupole
Ion source: ES+/ES−
Scan range: 90-900 amu Method 2
Instrument: LC/MS ThermoFinnigan HPLC Surveyor DAD, MSQ single quadrupole
Column: Synergi Hydro RP100A, 2.5 μm, 3×50 mm
Mobile phase: A=H$_2$O 90%+10% CH$_3$CN+NH$_4$COOH 10 mM
B=CH$_3$CN 90%+H$_2$O 10%+NH$_4$COOH 10 mM

| Time in min: | % A | % B | Flow rate in mL/min |
|---|---|---|---|
| 0.00 | 100 | 0 | 1.2 |
| 0.50 | 100 | 0 | 1.2 |
| 6.50 | 0 | 100 | 1.2 |
| 7.50 | 0 | 100 | 1.2 |
| 8.00 | 100 | 0 | 1.2 |
| 9.00 | 100 | 0 | 1.2 |

Detection: UV 254 nm
Detection: Finnigan MSQ, single quadrupole
Ion source: APCI+/APCI−
Scan range: 100-900 amu Method 3
Instrument: LC/MS ThermoFinnigan HPLC Surveyor DAD, LCQFleet Ion Trap
Column: Xselect CSH, 2.5 μm, 4.6×50 mm
Mobile phase: A=H$_2$O 90%+10% CH$_3$CN+HCOOH 0.1%
B=CH$_3$CN 90%+H$_2$O 10%+HCOOH 0.1%

| Time in min: | % A | % B | Flow rate in mL/min |
|---|---|---|---|
| 0.00 | 100 | 0 | 1.4 |
| 4.00 | 0 | 100 | 1.4 |
| 5.30 | 0 | 100 | 1.4 |
| 5.50 | 100 | 0 | 1.4 |
| 6.00 | 100 | 0 | 1.4 |

Detection: UV 254 nm
Detection: Finnigan Fleet, Ion Trap
Ion source: ES+
Scan range: 100-900 amu Method 4
Instrument: LC/MS Waters Acquity UPLC System DAD, SQD single quadrupole
Column: BEH C18 1.7 μm 2.1×50 mm, Temp 35° C.
Mobile phase: A=H$_2$O 90%+CH$_3$CN 10%+CF$_3$COOH 0.1%
B=CH$_3$CN 90%+H$_2$O 10%

| Time in min | % A | % B | flow rate in mL/min |
|---|---|---|---|
| 0.00 | 100 | 0 | 0.70 |
| 0.70 | 0 | 100 | 0.70 |
| 2.30 | 0 | 100 | 0.70 |
| 2.40 | 100 | 0 | 0.70 |
| 2.60 | 100 | 0 | 0.70 |

Detection: UV 254 nm
Detection: SQD, single quadrupole
Ion source: ES+/ES−
Scan range: 90-900 amu
Method 5
Instrument: LC/MS Waters Acquity UPLC System DAD, SQD single quadrupole
Column: BEH C18 1.7 µm 2.1×50 mm, Temp 35° C.
Mobile phase: A=$H_2O$ 90%+$CH_3CN$ 10%+$NH_4HCO_3$ 5 mM
B=$CH_3CN$ 90%+$H_2O$ 10%

| Time in min | % A | % B | flow rate in mL/min |
|---|---|---|---|
| 0.00 | 100 | 0 | 0.70 |
| 1.20 | 0 | 100 | 0.70 |
| 1.45 | 0 | 100 | 0.70 |
| 1.55 | 100 | 0 | 0.70 |
| 1.75 | 100 | 0 | 0.70 |

Detection: UV 254 nm
Detection: SQD, single quadrupole
Ion source: ES+/ES−
Scan range: 90-900 amu
Method 6
Instrument: LC/MS Waters Alliance 2695 HPLC System DAD, Quattro Micro Triple quadrupole
Column: Atlantis dC18 5µm 4.6×50 mm, Temp 35° C.
Mobile phase: A=$H_2O$ 90%+10% $CH_3CN$+$CF_3COOH$ 0.05%
B=$CH_3CN$ 90%+10% $H_2O$

| Time in min | % A | % B | flow rate in ml/min |
|---|---|---|---|
| 0.00 | 100 | 0 | 1.3 |
| 0.70 | 100 | 0 | 1.3 |
| 4.5 | 0 | 100 | 1.3 |
| 5.80 | 0 | 100 | 1.3 |
| 6.00 | 100 | 0 | 1.3 |

Detection: UV 254 nm
Detection: Quattro Micro, triple quadrupole
Ion source: ES+
Scan range: 90-1000 amu
Method 7
Instrument: LC/MS Waters Alliance 2695 HPLC System DAD, Quattro Micro Triple quadrupole
Column: Zorbax Eclipse XDB-C18 3.5µm 4.6×50 mm, Temp 35° C.
Mobile phase: A=$H_2O$ 90%+10% $CH_3CN$+$NH_4COOH$ 5 mM
B=$CH_3CN$ 90%+10% $H_2O$

| Time in min | % A | % B | flow rate in ml/min |
|---|---|---|---|
| 0.00 | 100 | 0 | 1.3 |
| 4.50 | 0 | 100 | 1.3 |
| 5.80 | 0 | 100 | 1.3 |
| 6.00 | 100 | 0 | 1.3 |

Detection: UV 254 nm
Detection: Quattro Micro, triple quadrupole
Ion source: ES+/−
Scan range: 90-1000 amu
Method 8
Instrument: LC/MS Waters Alliance 2695 HPLC System DAD, Quattro Micro Triple quadrupole
Column: Xbridge Phenyl 3.5µm 3×30 mm, Temp 35° C.
Mobile phase: A=$H_2O$ 90%+10% $CH_3CN$+$NH_4HCO_3$ 5 mM
B=$CH_3CN$ 90%+10% $H_2O$

| Time in min | % A | % B | flow rate in ml/min |
|---|---|---|---|
| 0.00 | 100 | 0 | 1.3 |
| 4.50 | 0 | 100 | 1.3 |
| 5.80 | 0 | 100 | 1.3 |
| 6.00 | 100 | 0 | 1.3 |

Detection: UV 254 nm
Detection: Quattro Micro, triple quadrupole
Ion source: ES+/−
Scan range: 90-1000 amu
GC-MS Methods:
Method 9
Instrument: GC/MS Thermo Scientific TRACE GC ULTRA, DSQ II MS single quadrupole
Column: Agilent DB-5MS, 25 m×0.25 mm×0.25 um
Carrier gas: Helium, 1 mL/min constant flow
Oven Program: 50° C., to 100° C. in 10° C./min, to 200° C. in 20° C./min, to 320° C. in 30° C./min (hold 10 min).
Detection: DSQ II MS single quadrupole
Ion source: EI
Scan range: 50-450 amu
Microwave Heating:
Discover® OEM instruments, equipped with 10 and 35 mL vessels
NMR Equipment:
The 1H NMR spectra were recorded on a Bruker Avance III (500 MHz) or a Varian 400 (400 MHz) instrument using deuterated dimethylsulfoxide (DMSO-d6) as the solvent with tetramethylsilane (TMS) or the residual solvent peak as an internal standard. Chemical shifts are reported in δ values (ppm) relative to TMS.

Synthesis of Intermediates

Intermediate 1

1-(4-Hydroxymethyl-benzyl)-1H-[1,2,3]triazole-4-carboxylic acid ethyl ester

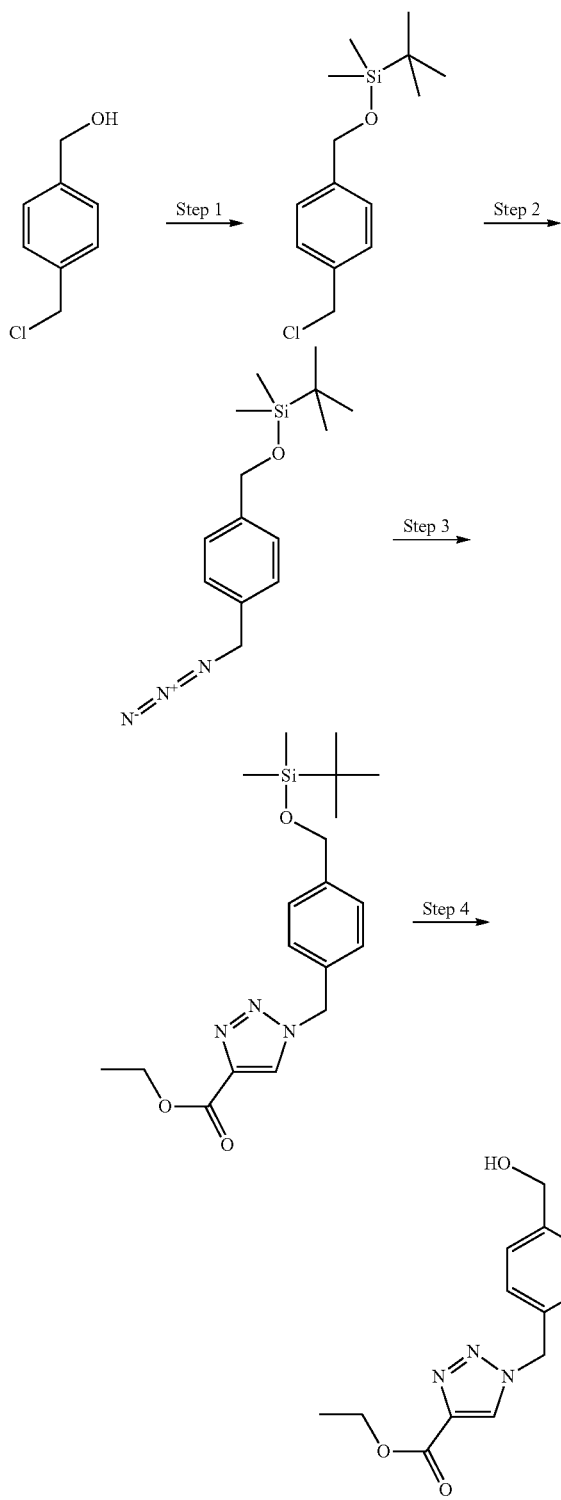

Step 1: tert-Butyl-(4-chloromethyl-benzyloxy)-dimethyl-silane 4-(chloromethyl)benzylalcohol (5 g, 31.9 mmol) is dissolved in anhydrous dichloromethane (50 ml), tert-butyldimethylchlorosilane (5.29 g, 35.1 mmol) and imidazole (2.82 g, 41.5 mmol) are added at room temperature and the mixture is stirred for 2 hours. The solution is washed with water, the organic layer is collected and concentrated under reduced pressure to give the title compound (Yield 8.4 g).

GC (Method 9): $t_R$=9.99 min; Mass spectrum (EI+): m/z=213, fragment [M-tBu]$^+$.

Step 2: (4-Azidomethyl-benzyloxy)-tert-butyl-dimethyl-silane tert-Butyl-(4-chloromethyl-benzyloxy)-dimethyl-silane (5 g, 18.5 mmol) and sodium azide (4.8 g, 73.8 mmol) are suspended in anhydrous N,N-dimethylformamide (50 ml), the mixture is stirred at room temperature for 24 hours. The solution is concentrated then dichloromethane (50 ml) and water (50 ml) are added, the organic layer is collected, dried over sodium sulfate and concentrated to give the title compound. (Yield 4.6 g)

GC (Method 9): $t_R$=10.36 min; Mass spectrum (EI+): m/z=220, fragment [M-tBu]$^+$.

Step 3: 1-[4-(tert-Butyl-dimethyl-silanyloxymethyl)-benzyl]-1H-[1,2,3]triazole-4-carboxylic acid ethyl ester (4-Azidomethyl-benzyloxy)-tert-butyl-dimethyl-silane (4.6 g, 14.9 mmol) and ethyl propiolate (1.52 ml, 14.9 mmol) are dissolved in a mixture of tert-butanol (20 ml) and water (20 ml), then sodium ascorbate (2.95 g, 14.9 mmol) and cupric sulfate pentahydrate (745 mg, 2.98 mmol) are added and the mixture is stirred for 6 hours. The mixture is concentrated, then water (80 ml) is added and the mixture is extracted with dichloromethane (80 ml). The organic phase is collected and concentrated under vacuum, the residue is purified by flash chromatography (20-50% ethyl acetate in cyclohexane) to give the title compound (Yield 1.98 g).

LC (Method 1): $t_R$=1.53 min; Mass spectrum (ES+): m/z=376 [M+H]$^+$.

Step 4: 1-(4-Hydroxymethyl-benzyl)-1H-[1,2,3]triazole-4-carboxylic acid ethyl ester 1-[4-(tert-Butyl-dimethyl-silanyloxymethyl)-benzyl]-1H-[1,2,3]triazole-4-carboxylic acid ethyl ester (1.98 g, 5.16 mmol) is dissolved in anhydrous tetrahydrofuran (20 ml), tetrabutylammonium fluoride (1M in tetrahydrofuran, 7.75 ml, 7.75 mmol) is added at room temperature and the mixture is stirred for 2 hours. The mixture is concentrated, then water is added and the mixture is extracted with dichloromethane. The organic phase is collected and concentrated under vacuum, the residue is purified by flash chromatography (20-60% ethyl acetate in cyclohexane) to give the title compound (Yield 1.05 g).

LC (Method 1): $t_R$=0.73 min; Mass spectrum (ES+): m/z=262 [M+H]$^+$.

Intermediate 2

1-(4-Methanesulfonyloxymethyl-benzyl)-1H-[1,2,3]triazole-4-carboxylic acid ethylester

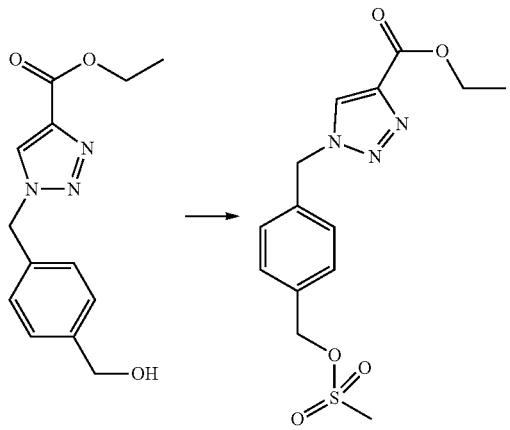 [SMILES: CCOC(=O)c1cn(Cc2ccc(CO)cc2)nn1 ; CCOC(=O)c1cn(Cc2ccc(COS(C)(=O)=O)cc2)nn1]

1-(4-Hydroxymethyl-benzyl)-1H-[1,2,3]triazole-4-carboxylic acid ethyl ester (Intermediate 1, 550 mg, 2.06 mmol) and N,N-diisopropylethylamine (0.90 ml, 5.15 mmol) are suspended in anhydrous dichloromethane (15 ml). The solution is cooled to 0° C. and methanesulfonyl chloride (0.24 ml, 3.1 mmol) is added under stirring. The cooling bath is removed and the solution is stirred at room temperature for 1 hour. Dichloromethane (30 ml) is added and the organic solution is washed with water (50 ml), the organic layer is collected, dried over sodium sulfate and concentrated. The residue is purified by flash chromatography (10-80% ethyl acetate in cyclohexane) to give the title compound (Yield 410 mg).

LC (Method 2): $t_R$=3.37 min; Mass spectrum (ES+): m/z=340 [M+H]$^+$.

Intermediate 3

3-Isopropenyl-pyridin-2-ol

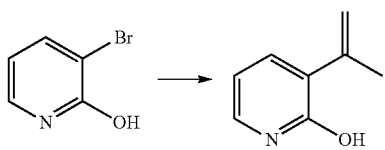

3-Bromo-pyridin-2-ol (commercially available TCI Europe B2330, 2 g, 11.5 mmol), 2-isopropenyl-4,4,5,5-tetramethyl-[1,3,2]dioxaborolane (4.3 ml, 23.0 mmol), potassium carbonate (4.77 g, 34.5 mmol), [1,1'-bis(diphenylphosphino)ferrocene] dichloropalladium(II) (1.26 g, 1.72 mmol) are dissolved in toluene (40 ml), the mixture is refluxed for 1 h, then the solution is cooled to room temperature. Ethyl acetate and water are added and partitioned, the organic layer is collected and concentrated under vacuum, the residue is purified by flash chromatography (20-100% ethyl acetate in cyclohexane) to give the title compound (Yield 1.40 g).

LC (Method 1): $t_R$=0.68 min; Mass spectrum (ES+): m/z=136 [M+H]+.

Intermediate 4

1-[4-(3-Isopropenyl-2-oxo-2H-pyridin-1-ylmethyl)-benzyl]-1H-[1,2,3]triazole-4-carboxylic acid ethyl ester

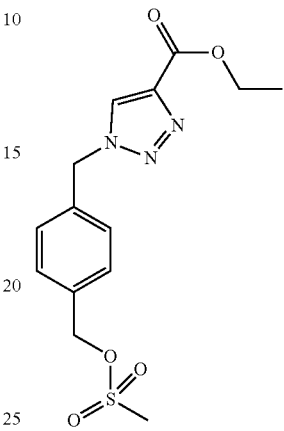

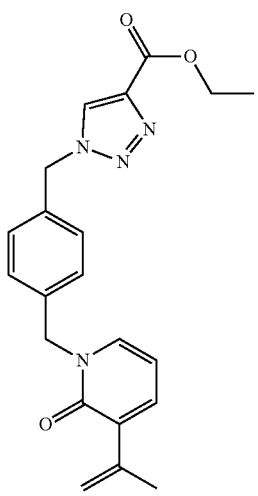

1-(4-Methanesulfonyloxymethyl-benzyl)-1H-[1,2,3]triazole-4-carboxylic acid ethyl ester (Intermediate 2, 160 mg, 0.46 mmol), 3-Isopropenyl-pyridin-2-ol (Intermediate 3, 63 mg, 0.46 mmol) and cesium carbonate (298 mg, 0.91 mmol) are dissolved in N,N-dimethylformamide (8 ml), the mixture is stirred at room temperature for 2 hours, then dichloromethane (25 ml) is added. The solution is filtered and concentrated under reduced pressure. The residue is purified by flash chromatography (0-10% methanol in dichloromethane) to give the title compound (Yield 120 mg).

LC (Method 1): $t_R$=1.05 min; Mass spectrum (ES+): m/z=379 [M+H]+

Intermediate 5

[4-(Fluoro-isoxazol-3-yl-methyl)-phenyl]-methanol

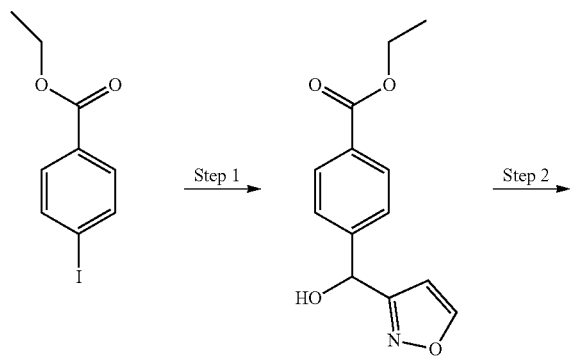

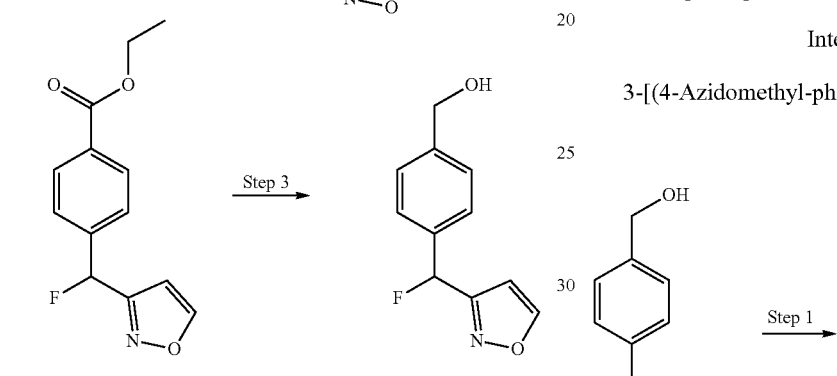

Step 1: 4-(Hydroxy-isoxazol-3-yl-methyl)-benzoic acid ethyl ester

Ethyl 4-iodobenzoate (4 g, 14.5 mmol) is dissolved in anhydrous tetrahydrofuran (20 ml), the solution is stirred under nitrogen and cooled to −50° C., isopropylmagnesium chloride (2M in tetrahydrofuran, 8.7 ml, 17.4 mmol) is slowly added and stirred for 2 hours at −50° C. The mixture is cooled to −78° C. then isoxazole-3-carboxaldehyde (1.55 g, 15.9 mmol) dissolved in tetrahydrofuran (10 ml) is added, after 1 hour at −78° C. the mixture is warmed to room temperature and stirred overnight. The mixture is concentrated and saturated aqueous NaHCO$_3$ solution is added, the mixture is extracted with dichloromethane, the organic layer is collected and concentrated. The residue is purified by flash chromatography (10-80% ethyl acetate in cyclohexane) to give the title compound (Yield 3 g).

LC (Method 1): $t_R$=0.91 min; Mass spectrum (ES+): m/z=248 [M+H]$^+$.

Step 2: 4-(Fluoro-isoxazol-3-yl-methyl)-benzoic acid ethyl ester

4-(Hydroxy-isoxazol-3-yl-methyl)-benzoic acid ethyl ester (1.5 g, 6.0 mmol) is dissolved in anhydrous dichloromethane (15 ml), the mixture is stirred and cooled to −60° C. then bis(2-methoxyethyl)aminosulfur trifluoride (2.28 g, 7.20 mmol) is added, after 1 hour the mixture is warmed to room temperature and stirred for 1 hour. Saturated aqueous NH$_4$Cl solution is added, the organic layer is collected and concentrated to give the title compound (Yield 1.16 g).

GC (Method 9): $t_R$=10.48 min; Mass spectrum (EI+): m/z=249 [M]$^+$.

Step 3: [4-(Fluoro-isoxazol-3-yl-methyl)-phenyl]-methanol

4-(Fluoro-isoxazol-3-yl-methyl)-benzoic acid ethyl ester (1.16 g, 4.65 mmol) is dissolved in anhydrous tetrahydrofuran (15 ml), the mixture is cooled to 0° C. then lithium borohydride (2M solution in tetrahydrofuran, 2.56 ml, 5.12 mmol) is added and the mixture is stirred at room temperature under nitrogen atmosphere. After 2 hours the reaction is cooled to 0° C. and water is added. The mixture is concentrated and HCl aq. 1N is added until pH 7 is reached. The mixture is concentrated and the residue is purified by flash chromatography (10-100% ethyl acetate in cyclohexane) to give the title compound (Yield 800 mg).

LC (Method 1): $t_R$=0.80 min; Mass spectrum (ES+): m/z=208 [M+H]$^+$.

Intermediate 6

3-[(4-Azidomethyl-phenyl)-fluoro-methyl]-isoxazole

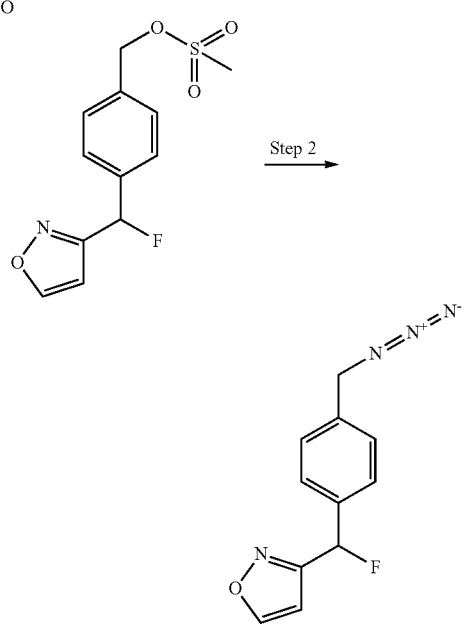

Step 1: Methanesulfonic acid 4-(fluoro-isoxazol-3-yl-methyl)-benzyl ester

[4-(Fluoro-isoxazol-3-yl-methyl)-phenyl]-methanol (Intermediate 5, 800 mg, 3.78 mmol) and N,N-diisopropylethylamine (1.65 ml, 9.46 mmol) are dissolved in anhydrous dichloromethane (15 ml). The solution is cooled to 0° C. and methanesulfonyl chloride (0.439 ml, 5.7 mmol) is added under stirring. The cooling bath is removed and the solution is stirred at 20° C. for 1 hour. Dichloromethane (30 ml) is added and the organic solution is washed with water (50 ml), the organic layer is collected, dried over sodium sulfate and concentrated to give the crude title compound (Yield 1.0 g).

LC (Method 1): $t_R$=0.97 min; Mass spectrum (ES+): m/z=286 [M+H]$^+$.

Step 2: 3-[(4-Azidomethyl-phenyl)-fluoro-methyl]-isoxazole

Crude methanesulfonic acid 4-(fluoro-isoxazol-3-yl-methyl)-benzyl ester (1.0 g, 3.50 mmol) and sodium azide (0.91 g, 14 mmol) are dissolved in anhydrous N,N-dimethylformamide (15 ml), the mixture is stirred at 25° C. for 24 hours. The solution is concentrated then dichloromethane (50 ml) and water (50 ml) are added, the organic layer is collected, dried over sodium sulfate and concentrated to give the title compound (Yield 600 mg).

LC (Method 1): $t_R$=1.14 min; Mass spectrum (ES+): m/z=233 [M+H]$^+$.

Intermediate 7

1-[4-(Fluoro-isoxazol-3-yl-methyl)-benzyl]-1H-[1,2,3]triazole-4-carboxylic acid ethyl ester

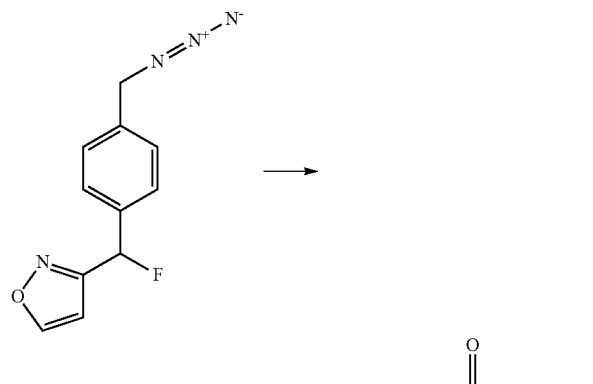

3-[(4-Azidomethyl-phenyl)-fluoro-methyl]-isoxazole (Intermediate 6, 600 mg, 2.19) and ethyl propiolate (237 mg, 2.41 mmol) are dissolved in a mixture of tert-butanol (8 ml) and water (8 ml), then sodium ascorbate (435 mg, 2.19 mmol) and cupric sulfate pentahydrate (110 mg, 0.44 mmol) are added and the mixture is stirred for 1 hour. The mixture is concentrated, then water is added and the mixture is extracted with dichloromethane (100 ml). The organic phase is collected and concentrated under vacuum, the residue is purified by flash chromatography (0-100% ethyl acetate in cyclohexane) to give the title compound (Yield 500 mg).

LC (Method 1): $t_R$=1.01 min; Mass spectrum (ES+): m/z=331 [M+H]$^+$.

Intermediate 8

1-(4-Chloromethyl-benzyl)-1H-pyrazole-4-carboxylic acid ethyl ester

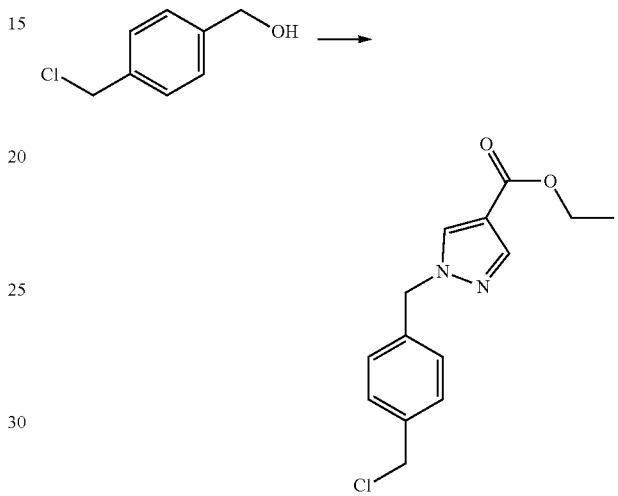

1H-Pyrazole-4-carboxylic acid ethyl ester (2 g, 13.9 mmol), (4-chloromethyl-phenyl)-methanol (2.21 g, 13.9 mmol) and triphenylphosphine (4.49 g, 16.8 mmol) are dissolved in tetrahydrofuran (40 ml). The solution is cooled to 0° C. then diethylazodicarboxylate (6.47 ml, 16.6 mmol) is added. The mixture is stirred at 0° C. for 2 hours, then 1 hour at room temperature. The solvent is removed under vacuum and the residue is purified by flash chromatography (0-50% ethyl acetate in cyclohexane) to give the title compound (Yield 1.72 g).

LC (Method 2): $t_R$=4.40 min; Mass spectrum (ES+): m/z=279 [M+H]+

Intermediate 9

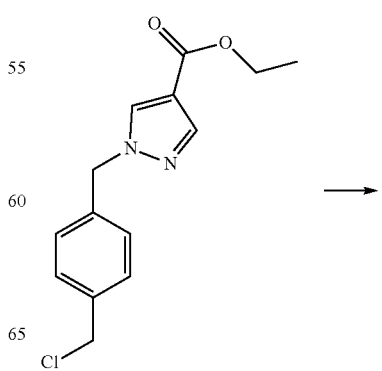

-continued

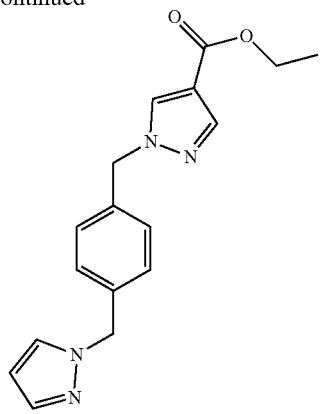

1-(4-Chloromethyl-benzyl)-1H-pyrazole-4-carboxylic acid ethyl ester (Intermediate 8, 700 mg, 2.44 mmol), pyrazole (331 mg, 4.88 mmol) and sodium hydride (175 mg, 60% oil dispersion, 7.30 mmol) are dissolved in N,N-dimethylformamide (10 ml), the mixture is stirred at 80° C. for 2 hours, then concentrated under reduced pressure. The residue is purified by flash chromatography (10-90% ethyl acetate in cyclohexane) to give the title compound (Yield 300 mg).

LC (Method 1): $t_R$=0.98 min; Mass spectrum (ES+): m/z=311 [M+H]+

Intermediate 10

1-[4-(2-Oxo-2H-pyridin-1-ylmethyl)-benzyl]-1H-pyrazole-4-carboxylic acid ethyl ester

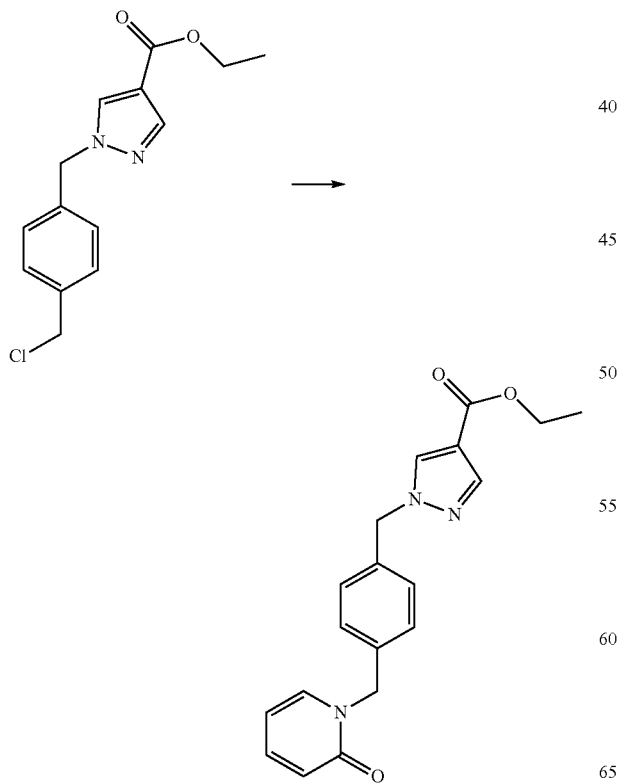

1-(4-Chloromethyl-benzyl)-1H-pyrazole-4-carboxylic acid ethyl ester (Intermediate 8, 660 mg, 2.30 mmol), 2-hydroxypyridine (225 mg, 2.30 mmol) and cesium carbonate (1.50 g, 4.59 mmol) are dissolved in N,N-dimethylformamide (8 ml), the mixture is stirred at room temperature for 2 hours, then dichloromethane (25 ml) is added. The solution is filtered and concentrated under reduced pressure. The residue is purified by flash chromatography (0-10% methanol in dichloromethane) to give the title compound (Yield 587 mg).

LC (Method 2): $t_R$=3.50 min; Mass spectrum (ES+): m/z=338 [M+H]+

Intermediate 11

1-(2-Methyl-quinolin-6-ylmethyl)-1H-[1,2,3] triazole-4-carboxylic acid ethyl ester

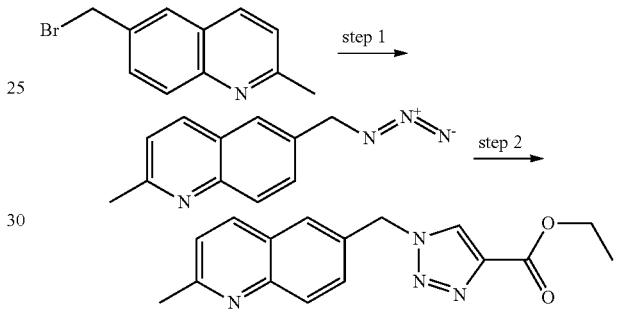

Step 1: 6-Azidomethyl-2-methyl-quinoline

6-Bromomethyl-2-methyl-quinoline (commercially available from Achemblock, F-4030, 2 g, 8.47 mmol) and sodium azide (2.2 g, 33.9 mmol) are dissolved in N,N-dimethylformamide dry (40 ml) and stirred overnight in the absence of light. The mixture is concentrated under vacuum and the residue is purified by flash chromatography (0-40% ethyl acetate in cyclohexane) to give the title compound (Yield 1.6 g).

LC (Method 2): $t_R$=4.05 min; Mass spectrum (ES+): m/z=199 [M+H]$^+$.

Step 2: 1-(2-Methyl-quinolin-6-ylmethyl)-1H-[1,2,3] triazole-4-carboxylic acid ethyl ester 6-Azidomethyl-2-methyl-quinoline (2.2 g, 10.79 mmol) and ethyl propiolate (1.1 ml, 10.79 mmol) are dissolved in a mixture of tert-butanol (8 ml) and water (8 ml), then sodium ascorbate (2.14 g, 10.79 mmol) and cupric sulfate pentahydrate (539 mg, 2.16 mmol) are added and the mixture is stirred overnight.

Water (50 ml) is added and the mixture is extracted with dichloromethane. The organic phase is collected and concentrated under vacuum, the residue is purified by flash chromatography (0-80% ethyl acetate in cyclohexane) to give the title compound (Yield 2.2 g).

LC (Method 2): $t_R$=3.42 min; Mass spectrum (ES+): m/z=297 [M+H]$^+$.

Intermediate 12

1-(2-Methyl-quinolin-6-ylmethyl)-1H-[1,2,3]triazole-4-carboxylic acid

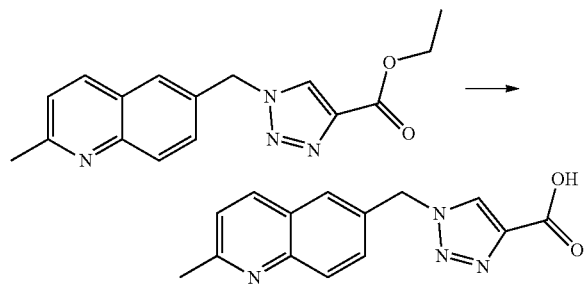

1-(2-Methyl-quinolin-6-ylmethyl)-1H-[1,2,3] triazole-4-carboxylic acid ethyl ester (Intermediate 11, 1.0 g, 3.27 mmol) is dissolved in tetrahydrofuran (10 ml) and water (2 ml), then the solution is cooled to 0° C. Under stirring lithium hydroxide (156 mg, 6.54 mmol) is added and the solution is allowed to warm to room temperature, after 2 hours the mixture is concentrated to remove the organic solvent and the aqueous residue is washed with ethyl acetate, HCl 1M aq. solution is added to the aqueous phase until pH 3 is reached then concentrated. The residue is purified by reverse phase flash chromatography (0-100% methanol in water) to give the title compound (Yield 810 mg).

LC (Method 1): $t_R$=0.45 min; Mass spectrum (ES+): m/z=269 [M+H]$^+$.

The compounds in the following table are synthesized in analogy to the method described for Intermediate 12.

| Intermediate | Structure | Starting intermediates | Yield | Analysis |
|---|---|---|---|---|
| 13 | 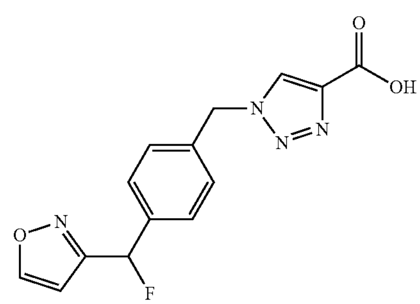 [SMILES: O=C(O)c1cn(Cc2ccc(C(F)c3ccon3)cc2)nn1] | Intermediate 7 (570 mg), overnight at room temperature no purification, product extracted with ethyl acetate | 300 mg | LC (Method 1): $t_R$ = 0.64 min; Mass spectrum (ES+): 303 m/z = [M + H]$^+$. |
| 14 | 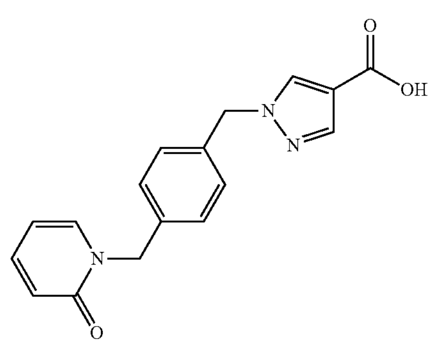 [SMILES: O=C(O)c1cnn(Cc2ccc(Cn3ccccc3=O)cc2)c1] | Intermediate 10 (570 mg) overnight at 40° C. no purification, product extracted with ethyl acetate | 440 mg | LC (Method 3): $t_R$ = 2.22 min; Mass spectrum (ES+): m/z = 310 [M + H]$^+$. |
| 15 | 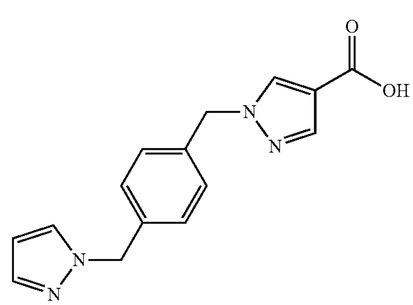 [SMILES: O=C(O)c1cnn(Cc2ccc(Cn3cccn3)cc2)c1] | Intermediate 9 (335 mg) overnight at 40° C. no purification, product extracted with ethyl acetate | 300 mg | LC (Method 3): $t_R$ = 2.50 min; Mass spectrum (ES+): m/z = 283 [M + H]$^+$. |

| Intermediate | Structure | Starting intermediates | Yield | Analysis |
|---|---|---|---|---|
| 16 | (structure shown) | Intermediate 4 (570 mg) overnight at 40° C. no purification, product extracted with ethyl acetate | 300 mg | LC (Method 1): $t_R$ = 0.69 min; Mass spectrum (ES+): m/z = 351 [M + H]$^+$. |

Intermediate 17

1-(4-Bromomethyl-benzyl)-1H-[1,2,3]triazole-4-carboxylic acid tert-butyl ester

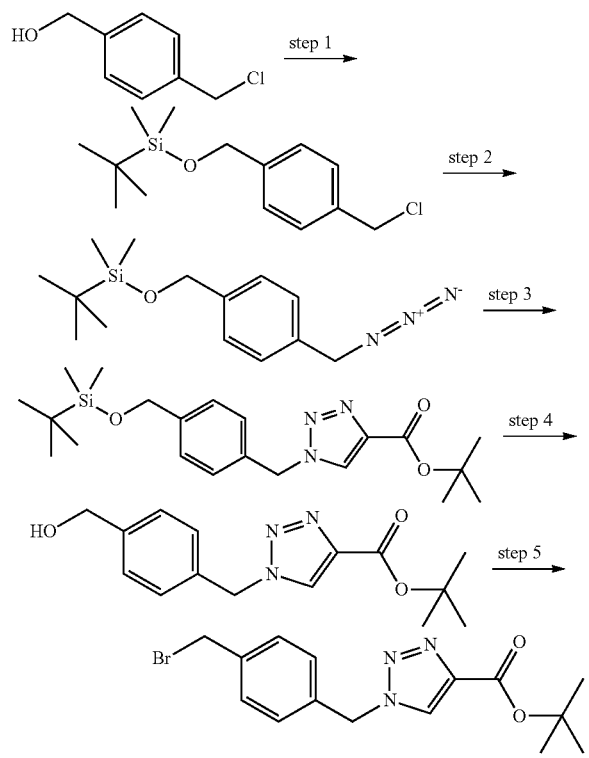

Step 1: tert-Butyl-(4-chloromethyl-benzyloxy)-dimethethyl-silane

Tert-butyldimethylchlorosilane (26.5 g, 176 mmol) and imidazole (14.1 g, 68.1 mmol) are added to a stirred solution of 4-(chloromethyl)benzyl alcohol (25 g, 160 mmol) dissolved in 300 ml of dry DCM and the reaction mixture is stirred at room temperature for 2 hours. Water is added, the organic layer is separated and concentrated under reduced pressure to obtain the crude title compound (Yield 42.5 g).

GC (Method 9): $t_R$=9.96 min; Mass spectrum (EI+): m/z=270 [M]$^+$

Step 2: (4-Azidomethyl-benzyloxy)-tert-butyl-dimethy-silane tert-Butyl-(4-chloromethyl-benzyloxy)-dimethethyl-silane (42.5 g) and sodium azide (14.5 g, 223 mmol) are dissolved in 150 ml of dry N,N-dimethylformamide and the reaction mixture is stirred at room temperature for 24 hours. The mixture is concentrated and the residue is partitioned between water and DCM; the organic layer is separated and concentrated under reduced pressure to obtain the crude title compound (Yield 41.4 g).

GC (Method 9): $t_R$=10.36 min; Mass spectrum (EI+): m/z=220 [M-tBu]$^+$

Step 3: 1-[4-(tert-Butyl-dimethyl-silanyloxymethyl)-benzyl]-1H-[1,2,3]triazole-4-carboxylic acid tert-butyl ester Cupric sulfate pentahydrate (1.03 g, 4.11 mmol) and sodium ascorbate (4.07 g, 20.6 mmol) are added to a stirred solution of (4-azidomethyl-benzyloxy)-tert-butyl-dimethy-silane (6.0 g, 20.6 mmol) and tert-butyl propiolate (3.10 ml, 22.6 mmol) dissolved in a mixture of 50 ml of tert-butanol and 50 ml of water. The reaction mixture is stirred at room temperature for 2 hours. The solvent is removed under reduced pressure and the residue is partitioned between water and DCM. The organic layer is separated and concentrated under reduced pressure to obtain the crude title compound (Yield 8.3 g).

LC (Method 4): $t_R$=0.73 min; Mass spectrum (ES+): m/z=404 [M+H]$^+$.

Step 4: 1-(4-Hydroxymethyl-benzyl)-1H-[1,2,3]triazole-4-carboxylic acid tert-butyl ester 1-[4-(tert-Butyl-dimethyl-silanyloxymethyl)-benzyl]-1H-[1,2,3]triazole-4-carboxylic acid tert-butyl ester (5.95 g) is dissolved in 50 ml of dry THF and the solution is cooled with an ice/water bath. After 15 minutes stirring, tetrabutylammonium fluoride solution (1M in THF, 15 ml, 15 mmol) is added and the reaction mixture is stirred at room temperature for 3 hours. The solvent is removed under reduced pressure and the residue is partitioned between water and a mixture of diethylether/cyclohexane 9:1. The organic layer is separated, dried over Na$_2$SO$_4$, filtered and concentrated under reduced pressure to obtain the crude title compound (Yield 3.8 g).

LC (Method 1): $t_R$=0.89 min; Mass spectrum (ES+): m/z=290 [M+H]$^+$.

Step 5: 1-(4-Bromomethyl-benzyl)-1H-[1,2,3]triazole-4-carboxylic acid tert-butyl ester Carbon tetrabromide (3.5 g 10.5 mmol) is added to a stirred solution of 1-(4-hydroxymethyl-benzyl)-1H-[1,2,3] triazole-4-carboxylic acid tert-butyl ester (2.6 g) dissolved in 50 ml of DCM. The reaction mixture is cooled to 0° C., triphenylphosphine (2.8 g, 10.5 mmol) is added portion-wise and the reaction mixture is stirred at room temperature overnight. The solvent is removed under reduced pressure and the crude is purified by flash chromatography (10-30% EtOAc in cyclohexane) to give the title compound (Yield 3.2 g).

LC (Method 1): $t_R$=1.21 min; Mass spectrum (ES+): m/z=352-354 [M+H]$^+$.

Intermediate 18

1-(4-Pyrazol-1-ylmethyl-benzyl)-1H-[1,2,3]triazole-4-carboxylic acid

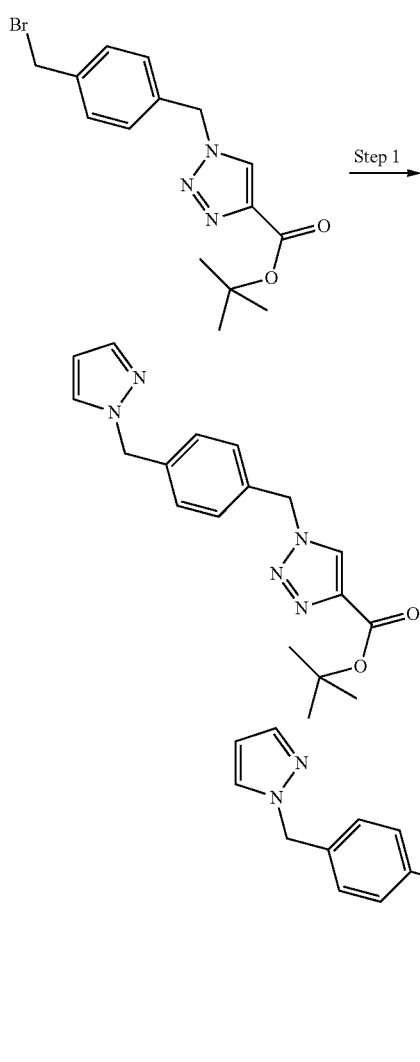

Step 1: 1-(4-Pyrazol-1-ylmethyl-benzyl)-1H-[1,2,3]triazole-4-carboxylic acid tert-butyl ester Intermediate 17 (500 mg, 0.93 mmol), pyrazole (62.8 mg, 0.93 mmol) and cesium carbonate (0.601 g, 1.84 mmol) are dissolved in N,N-dimethylformamide (10 ml). the mixture is warmed to 40° C. and stirred for 2 hours. The solvent is evaporated, dichloromethane (40 ml) is added and the mixture is washed with water. The organic layer is collected, dried over sodium sulphate, filtered and concentrated to give the title compound. (Yield 250 mg)

LC (Method 1): $t_R$=1.03 min; Mass spectrum (ES+): m/z=340 [M+H]+

Step 2: 1-(4-Pyrazol-1-ylmethyl-benzyl)-1H-[1,2,3]triazole-4-carboxylic acid 1-(4-Pyrazol-1-ylmethyl-benzyl)-1H-[1,2,3]triazole-4-carboxylic acid tert-butyl ester (250 mg, 0.74 mmol) and hydrogen chloride (4M in 1,4-dioxane, 2 mL, 8 mmol) are mixed together at 0° C., the mixture is stirred for 1 hour. The mixture is concentrated and the residue is triturated with diethyl ether to give the title compound. (Yield 200 mg)

LC (Method 1): $t_R$=0.60 min; Mass spectrum (ES+): m/z=284 [M+H]+

Intermediate 19

1-{4-[3-(1-Hydroxy-1-methyl-ethyl)-2-oxo-2H-pyridin-1-ylmethyl]-benzyl}-1H-[1,2,3]triazole-4-carboxylic acid

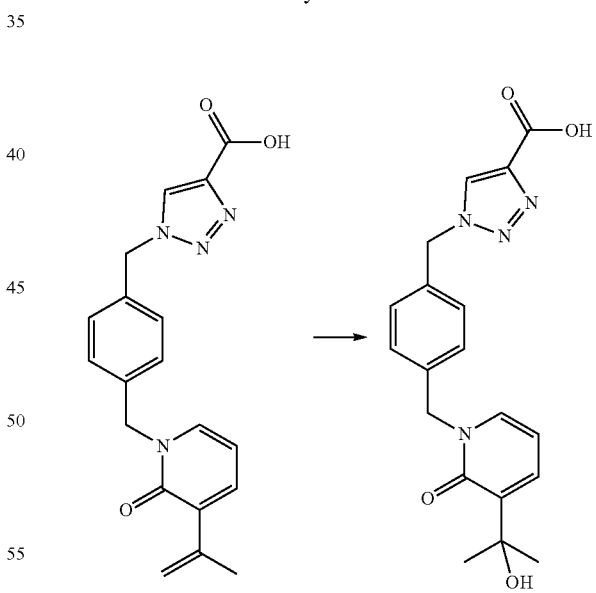

1-[4-(3-Isopropenyl-2-oxo-2H-pyridin-1-ylmethyl)-benzyl]-1H-[1,2,3]triazole-4-carboxylic acid (Intermediate 16, 150 mg, 0.42 mmol) is suspended in HCl 37% aq. solution (5 ml). The mixture is stirred at room temperature for 1 hour. The mixture is concentrated and the residue is purified by reverse phase flash chromatography (eluent: 0-50% acetonitrile in water) to give the title compound (Yield 80 mg).

LC (Method 1): $t_R$=0.60 min; Mass spectrum (ES+): m/z=369 [M+H]+

Intermediate 20

1-(6-Fluoro-pyridin-3-ylmethyl)-1H-pyrazole-4-carboxylic acid

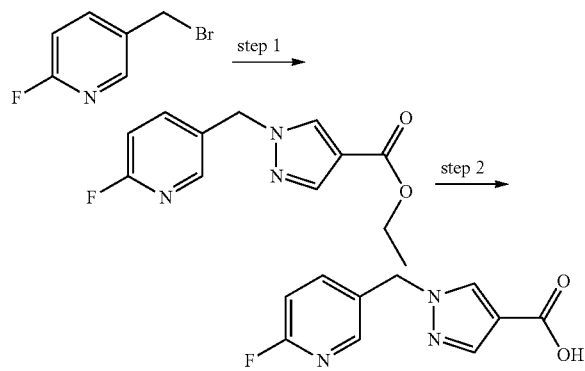

Step 1: 1-(6-Fluoro-pyridin-3-ylmethyl)-1H-pyrazole-4-carboxylic acid ethyl ester 5-(Bromomethyl)-2-fluoropyridine (available from Apollo Scientific, PC5845, 3.0 g, 15.8 mmol) is suspended in N,N-dimethylformamide (30 mL) and ethyl-4-pyrazole carboxylate (1.77 g, 12.6 mmol) and cesium carbonate (12.86 g, 39.5 mmol) are added. The mixture is stirred at 50° C. for 24 hours then diluted with ethyl acetate, washed with water and brine and the solvent removed under vacuum. The residue is purified by flash chromatography (0-10% EtOAc in cyclohexane) to give the title compound (Yield 2.60 g).

LC (Method 5): $t_R$=0.89 min; Mass spectrum (ES+): m/z=250 [M+H]$^+$.

Step 2: 1-(6-Fluoro-pyridin-3-ylmethyl)-1H-pyrazole-4-carboxylic acid

The material from step 1 is suspended in a mixture of water (5 mL) and tetrahydrofuran (45 mL) and lithium hydroxide monohydrate (0.48 g, 11.47 mmol) is added. The mixture is stirred for 24 hours then concentrated under vacuum, diluted with EtOAc and water and the phases separated. The aqueous phase is acidified to pH 2 with the addition of 1M HCl solution then extracted with dichloromethane. The dichloromethane extract is evaporated to give the title compound (Yield 1.80 g).

LC (Method 5): $t_R$=0.30 min; Mass spectrum (ES+): m/z=222 [M+H]$^+$.

Intermediate 21

1-(6-Fluoro-pyridin-3-ylmethyl)-3-trifluoromethyl-1H-pyrazole-4-carboxylic acid

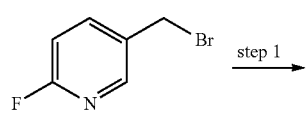

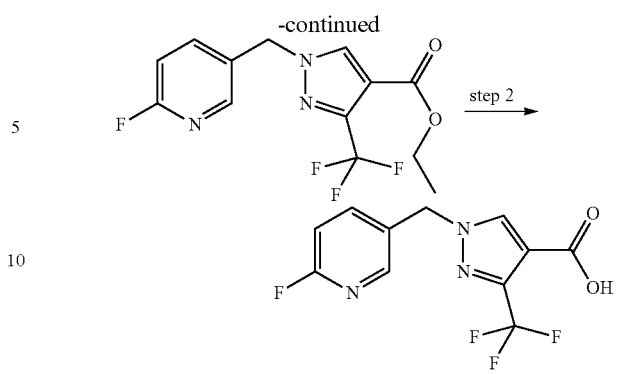

The title compound was prepared from 5-(bromomethyl)-2-fluoropyridine (available from Apollo Scientific, PC5845, 1.0 g, 5.26 mmol) and ethyl 3-(trifluoromethyl)pyrazole-4-carboxylate (0.88 g, 4.21 mmol) in analogy to the method described for the preparation of Intermediate 20 (Yield 0.80 g).

LC (Method 5): $t_R$=0.54 min; Mass spectrum (ES+): m/z=290 [M+H]$^+$.

Intermediate 22

1-[6-((S)-3-Methyl-pyrrolidin-1-yl)-pyridin-3-ylmethyl]-1H-pyrazole-4-carboxylic acid, Lithium Salt

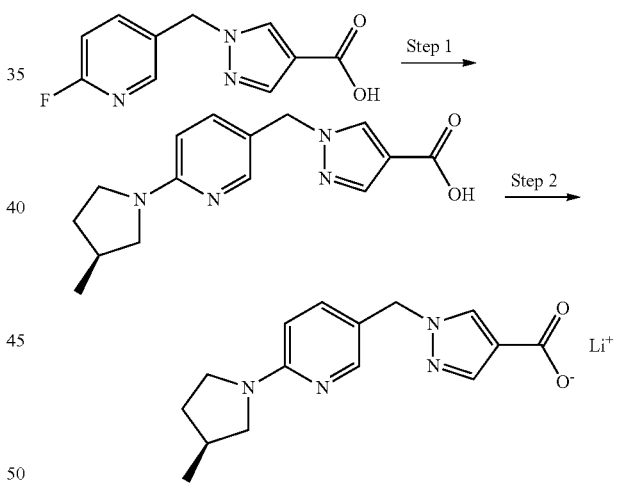

Step 1: 1-[6-((S)-3-Methyl-pyrrolidin-1-yl)-pyridin-3-ylmethyl]-1H-pyrazole-4-carboxylic acid 1-(6-Fluoro-pyridin-3-ylmethyl)-1H-pyrazole-4-carboxylic acid (Intermediate 20, 160 mg, 0.72 mmol) is suspended in 1,4-dioxane (15 mL) and (S)-3-methyl-pyrrolidine hydrochloride (176 mg, 1.45 mmol) and triethylamine (1 mL, 7.23 mmol) are added. The mixture is stirred at 50° C. overnight. Further (S)-3-methyl-pyrrolidine hydrochloride (88 mg, 0.72 mmol) and N,N-dimethylformamide (1 mL) are added and the mixture stirred for 4 days at 50° C. The solvent is evaporated and the residue purified by reverse phase flash chromatography (0-30% acetonitrile in water) to give the title compound (Yield 104 mg).

LC (Method 5): $t_R$=0.61 min; Mass spectrum (ES+): m/z=287 [M+H]⁺.

Step 2: 1-[6-((S)-3-Methyl-pyrrolidin-1-yl)-pyridin-3-ylmethyl]-1H-pyrazole-4-carboxylic acid Lithium Salt Part of the material from step 1 (54 mg, 0.19 mmol) and lithium hydroxide (4.5 mg, 0.19 mmol) are combined in water (0.2 mL) and stirred for 1 hour. The mixture is evaporated to give the title (Yield 40 mg).

LC (Method 5): $t_R$=0.61 min; Mass spectrum (ES+): m/z=287 [M+H]⁺.

Intermediate 23

1-[6-((S)-3-Methyl-pyrrolidin-1-yl)-pyridin-3-ylmethyl]-3-trifluoromethyl-1H-pyrazole-4-carboxylic acid

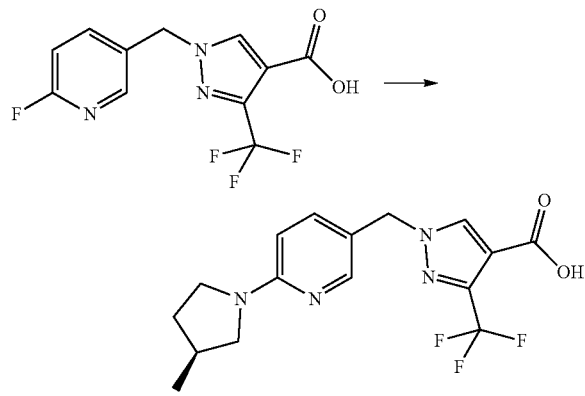

The title compound is prepared from Intermediate 21 (188 mg, 0.65 mmol) in analogy to the method described for the preparation of Intermediate 22 step 1 (Yield 100 mg).

LC (Method 1): $t_R$=0.73 min; Mass spectrum (ES+): m/z=355 [M+H]⁺.

Intermediate 24

1-(4-Chloromethyl-benzyl)-3-trifluoromethyl-1H-pyrazole-4-carboxylic acid ethyl ester

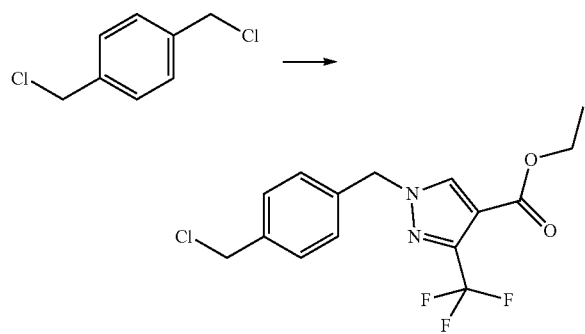

1,4-Bis-chloromethyl-benzene (4.2 g, 24.0 mmol), 3-trifluoromethyl-1H-pyrazole-4-carboxylic acid ethyl ester (2.5 g, 12.0 mmol) and cesium carbonate (5.87 g, 18.0 mmol) are dissolved in N,N-dimethylformamide (10 ml), the mixture is stirred at room temperature overnight, The solution is concentrated under reduced pressure, dichloromethane (100 ml) and water (100 ml) are added, phases are separated and the organic layer is collected and concentrated. The residue is purified by reverse phase flash chromatography (60 to 100% acetonitrile in water) to give the title compound (Yield 1.3 g).

LC (Method 3): $t_R$=1.32 min; Mass spectrum (ES+): m/z=347 [M+H]⁺.

Intermediate 25

1-[4-(4-Methyl-pyrazol-1-ylmethyl)-benzyl]-3-trifluoromethyl-1H-pyrazole-4-carboxylic acid ethyl ester

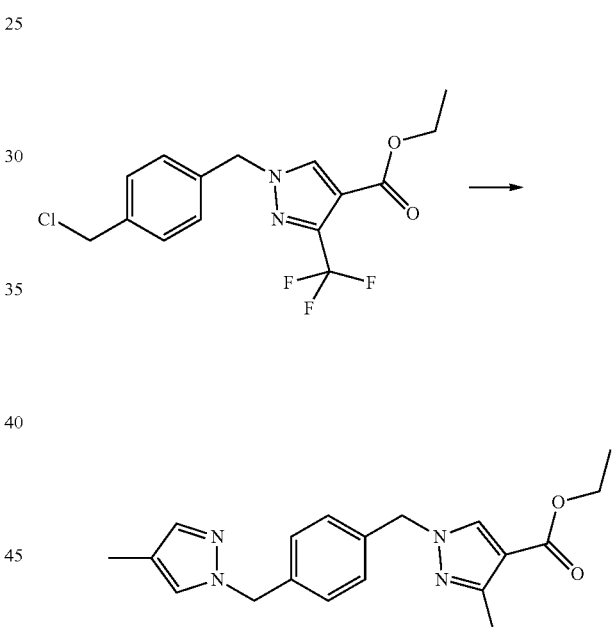

4-Methylpyrazole (76 mg, 0.92 mmol) is suspended in dry N,N-dimethylformamide (10 mL) and NaH (60% in mineral oil, 40 mg, 1.02 mmol) is added. The mixture is stirred until gas evolution is finished then 1-(4-Chloromethyl-benzyl)-3-trifluoromethyl-1H-pyrazole-4-carboxylic acid ethyl ester (Intermediate 24, 400 mg) is added and the mixture stirred for 2 hours. The mixture is then diluted with EtOAc and water, shaken and the phases separated. The organic phase is dried and the solvent removed. The residue is purified by flash chromatography (0-50% EtOAc in cyclohexane) to give the title compound (Yield 315 mg).

LC (Method 5): $t_R$=1.23 min; Mass spectrum (ES+): m/z=393 [M+H]⁺.

Intermediate 26

1-[4-(4-Methyl-pyrazol-1-ylmethyl)-benzyl]-3-trifluoromethyl-1H-pyrazole-4-carboxylic acid Lithium Salt

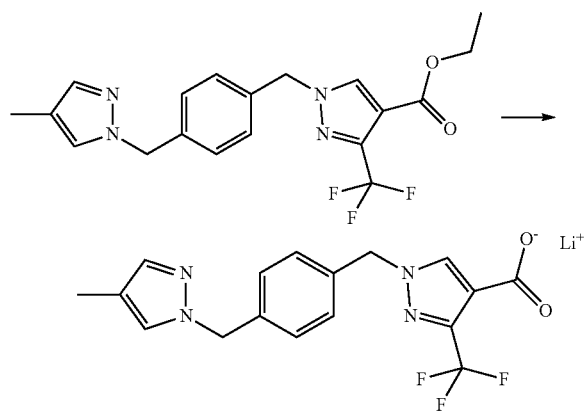

1-[4-(4-Methyl-pyrazol-1-ylmethyl)-benzyl]-3-trifluoromethyl-1H-pyrazole-4-carboxylic acid ethyl ester (Intermediate 25, 315 mg, 0.80 mmol) and lithium hydroxide (19 mg, 0.8 mmol) are suspended in a mixture of tetrahydrofuran (2 mL), methanol (1 mL) and water (1 mL) and stirred for 1 hour at 50° C., The solvent is evaporated and the residue dried under vacuum to give the title compound (Yield 295 mg).

LC (Method 5): $t_R$=0.66 min; Mass spectrum (ES+): m/z=365 [M+H]$^+$.

Intermediate 27

2-Chloro-5,6,7,8-tetrahydro-quinolin-5-ylamine

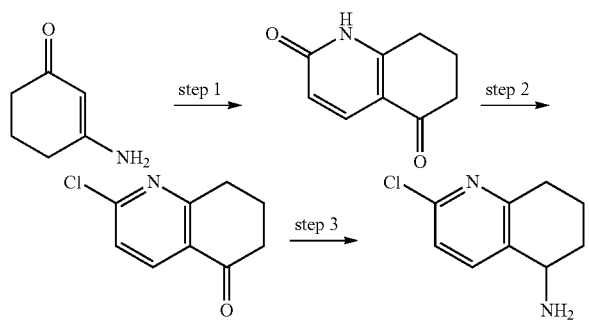

Step 1: 7,8-Dihydro-1H,6H-quinoline-2,5-dione

3-Amino-cyclohex-2-enone (3.5 g, 31.5 mmol) and methyl propiolate (2.8 ml, 31.5 mmol) are dissolved in N,N-dimethylformamide (20 ml), the mixture is stirred under reflux for 3 hours. The mixture is cooled with an ice bath and the precipitate is collected. methyl propiolate (2.8 ml, 31.5 mmol) is added to the filtrate and the mixture is heated again under reflux for 8 hours, then is cooled with an ice bath and the solid is collected. The combined precipitates are recrystallized from methanol and washed with diethyl ether to give the title compound. (Yield 720 mg)

LC (Method 2): $t_R$=0.32-0.63 min; Mass spectrum (ES+): m/z=164 [M+H]$^+$.

Step 2: 2-Chloro-7,8-dihydro-6H-quinolin-5-one 7,8-Dihydro-1H,6H-quinoline-2,5-dione (1.1 g, 6.74 mmol) is dissolved in acetonitrile (25 ml), phosphorus oxychloride (1.26 ml, 13.5 mmol) is added dropwise and the mixture is stirred at 100° C. for 3 hours. The mixture is cooled to 0° C. and poured into cold water, NaOH 2M aq. solution is added until pH>7 is reached, then the mixture is extracted with dichloromethane (3×30 ml), the combined organic layers are dried over sodium sulphate, filtered and concentrated. The residue is purified by flash chromatography (0-20% ethyl acetate in cyclohexane) to give the title compound (Yield 630 mg).

LC (Method 1): $t_R$=2.61 min; Mass spectrum (ES+): m/z=182 [M+H]$^+$.

Step 3: 2-Chloro-5,6,7,8-tetrahydro-quinolin-5-ylamine

2-Chloro-7,8-dihydro-6H-quinolin-5-one (630 mg, 3.40 mmol) and ammonium acetate (2.62 g, 34.0 mmol) are dissolved in methanol (20 ml), then sodium cyanoborohydride (149 mg, 2.38 mmol) is added and the mixture is stirred at room temperature for 48 hours.

HCl (8 ml 37% aq. solution) is added and methanol is evaporated, the residue is dissolved in water and washed with diethyl ether. Solid KOH is added to the aqueous solution until pH 9 is reached, then the mixture is extracted with diethyl ether. The organic phase is collected, dried over sodium sulphate and concentrated. The residue is purified by flash chromatography (0-50% methanol in ethyl acetate) to give the title compound (Yield 360 mg).

LC (Method 2): $t_R$=1.18 min; Mass spectrum (ES+): m/z=183 [M+H]$^+$.

Intermediate 28

1-(2-Methyl-quinolin-6-ylmethyl)-1H-[1,2,3]triazole-4-carboxylic acid (2-chloro-5,6,7,8-tetrahydro-quinolin-5-yl)-amide

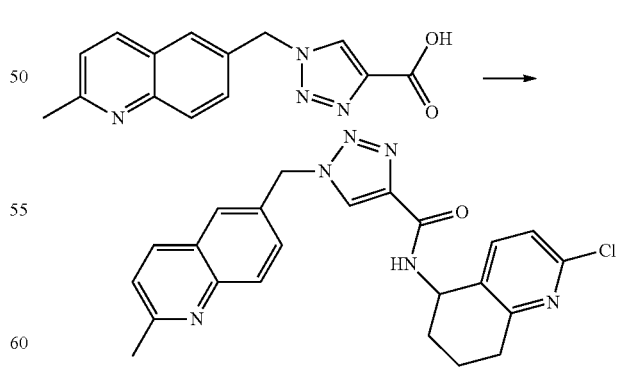

1-(2-Methyl-quinolin-6-ylmethyl)-1H-[1,2,3]triazole-4-carboxylic acid (Intermediate 12, 400 mg, 1.46 mmol), HATU (611 mg, 1.61 mmol) and N,N-diisopropylethylamine (0.37 ml, 2.2 mmol) are dissolved in dichloromethane (10 ml) and the mixture is stirred at room temperature. After 30 minutes a solution of 2-chloro-5,6,7,8-tetrahydro-quinolin-5-ylamine (Intermediate 27, 354 mg, 1.90 mmol) and N,N-diisopropylethylamine (0.37 ml, 2.2 mmol) in anhydrous N,N-dimethylformamide (10 ml) is added. The mixture is stirred at room temperature overnight. The solution is concentrated, the residue is dissolved in dichloromethane (100 ml) and washed with water (2×40 ml). The organic layer is collected, dried over sodium sulfate and concentrated. The residue is triturated with methanol to give the title compound (Yield 320 mg)

LC (Method 6): $t_R$=3.30 min; Mass spectrum (ES+): m/z=433 [M+H]$^+$.

Intermediate 29

(6,7-Dihydro-5H-[2]pyrindin-7-yl)-carbamic acid tert-butyl ester

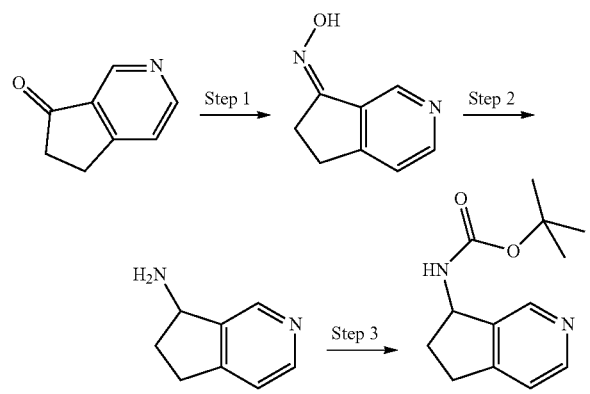

Step 1: 5,6-Dihydro-[2]pyrindin-7-one oxime 5,6-Dihydro-[2]pyrindin-7-one (synthesis described in EP2098513A1, 5 g, 37.5 mmol), hydroxylamine hydrochloride (3.13 g, 45.1 mmol) and sodium acetate (3.70 g, 45.0 mmol) are dissolved in water (8 ml), the mixture is stirred and ethanol (8 ml) is added to the solution. The mixture is stirred under reflux for 2 hours. The mixture is concentrated and ethyl acetate is added, salts are filtered off and the solution is concentrated to give the title compound (Yield 5.5 g)

LC (Method 1): $t_R$=0.61 min; Mass spectrum (ES+): m/z=149 [M+H]$^+$.

Step 2: 6,7-Dihydro-5H-[2]pyrindin-7-ylamine 5,6-Dihydro-[2]pyrindin-7-one oxime (5 g, 33.7 mmol) and zinc (4.41 g, 67.5 mmol) are dissolved in ethanol, the mixture is cooled to 0° C. then HCl aq. solution 37% (5.54 ml, 67.5 mmol) is added. After gas evolution is finished the mixture is heated to 70° C. and stirred for 20 minutes. The mixture is filtered and used in the next step without purification. (Yield 8.0 g)

LC (Method 1): $t_R$=0.32 min; Mass spectrum (ES+): m/z=135 [M+H]$^+$.

Step 3: (6,7-Dihydro-5H-[2]pyrindin-7-yl)-carbamic acid tert-butyl ester 6,7-Dihydro-5H-[2]pyrindin-7-ylamine (8 g, 29.8 mmol) and di-tert-butyldicarbonate (13.0 g, 59.6 mmol) are dissolved in tetrahydrofuran (30 ml). The mixture is stirred at room temperature for 24 hours. The solution is concentrated and the residue is purified by flash chromatography (0-100% ethyl acetate in cyclohexane) to give the title compound (Yield 6 g).

LC (Method 1): $t_R$=0.91 min; Mass spectrum (ES+): m/z=235 [M+H]$^+$

The compounds in the following table are synthesized in analogy to the method described for Intermediate 29.

| Intermediate | Structure | Starting intermediates | Yield | Analysis |
|---|---|---|---|---|
| 30 | ![structure] | 6,7-Dihydro-[1]pyrindin-5-one (commercially available from Santailabs ADH-7693, 2.7 g) | 1.2 g | LC (Method 7): $t_R$ = 3.02 min; Mass spectrum (ES+): m/z = 235 [M + H]$^+$. |
| 31 | ![structure] | 4-Methyl-6,7-dihydro-[1]pyrindin-5-one, (synthesis described in *Pharmazie*, 1995, vol. 50, 9 p. 589-592, 2.0 g). | 2.0 g | LC (Method 1): $t_R$ = 0.91 min; Mass spectrum (ES+): m/z = 249 [M + H]$^+$. |

| Intermediate | Structure | Starting intermediates | Yield | Analysis |
|---|---|---|---|---|
| 32 | 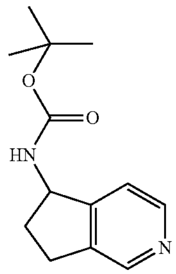 [SMILES: CC(C)(C)OC(=O)NC1CCc2cnccc21] | 6,7-Dihydro-[2]pyrindin-5-one (commercially available from ABCR AB 401490, 1.0 g) | 1.7 g | LC (Method 1): $t_R$ = 0.86 min; Mass spectrum (ES+): m/z = 235 [M + H]$^+$. |

Intermediate 33

2-((R)-2-Oxy-6,7-dihydro-5H-[2]pyrindin-5-yl)-isoindole-1,3-dione

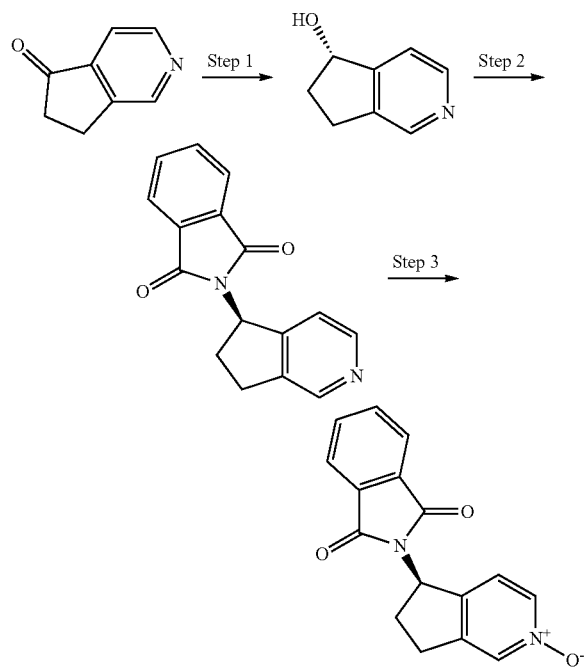

Step 1: (S)-6,7-Dihydro-5H-[2]pyrindin-5-ol

Triethylamine (16.18 ml, 116.1 mmol) is dissolved in dichloromethane (100 ml), the mixture is cooled to 0° C. and formic acid (4.95 ml, 131.4 mmol) is added dropwise, then 6,7-Dihydro-[2]pyrindin-5-one (commercially available from ABCR AB 401490, 5 g, 37.5 mmol) and Chloro[(1S,2S)-(−)-2-amino-1,2-diphenylethyl](4-toluensulfonyl) amido) (mesitylene) ruthenium(II) (467 mg, 0.75 mmol) is added. The mixture is stirred at room temperature overnight. Dichloromethane (100 ml) is added and the solution is washed with Na$_2$CO$_3$ aq. sat. solution (15 ml), the organic layer is collected, dried over sodium sulphate filtered and concentrated to give the title compound (Yield 5.0 g).

LC (Method 1): $t_R$=0.33 min; Mass spectrum (ES+): m/z=136 [M+H]$^+$

Chiral HPLC (Daicel chiralpak AS-H, Hexane:EtOH 85:15 1 ml/min, 25° C.) T$_R$=5.46 min, 98.0%.

Absolute stereochemistry assigned by analogy with Noyori et. al., J. Am. Chem. Soc., 1995, 117 (28), pp 7562-7563.

Step 2: (R)-2-(6,7-Dihydro-5H-[2]pyrindin-5-yl)-isoindole-1,3-dione (S)-6,7-Dihydro-5H-[2]pyrindin-5-ol (2 g, 13.3 mmol), phthalimide (1.96 g, 13.31 mmol) and triphenylphosphine (3.49 g, 13.3 mmol) are dissolved in tetrahydrofuran (40 ml). The solution is cooled to 0° C. then diisopropylazodicarboxylate (2.64 ml, 13.3 mmol) is added. The mixture is stirred at room temperature for 3 hours. The solvent is removed under vacuum and the residue is purified by flash chromatography (0-80% ethyl acetate in cyclohexane) to give the title compound (Yield 3.5 g).

LC (Method 1): $t_R$=0.92 min; Mass spectrum (ES+): m/z=265 [M+H]$^+$

Step 3: 2-((R)-2-Oxy-6,7-dihydro-5H-[2]pyrindin-5-yl)-isoindole-1,3-dione (R)-2-(6,7-Dihydro-5H-[2]pyrindin-5-yl)-isoindole-1,3-dione (3.5 g, 13.2 mmol) is dissolved in dichloromethane (20 ml), the solution is cooled to 0° C. and 3-chloroperoxybenzoic acid (3.85 g, 17.2 mmol) is added. The mixture is warmed to room temperature and stirred overnight. Dichloromethane (100 ml) is added and the solution is washed twice with Na$_2$CO$_3$ aq. sat. solution (20 ml), the organic layer is collected, dried over sodium sulphate filtered and concentrated to give the title compound. (Yield 3.5 g).

LC (Method 1): $t_R$=0.70 min; Mass spectrum (ES+): m/z=281 [M+H]$^+$

Intermediate 34

(R)-6,7-Dihydro-5H-[2]pyrindine-1,5-diamine dihydrochloride

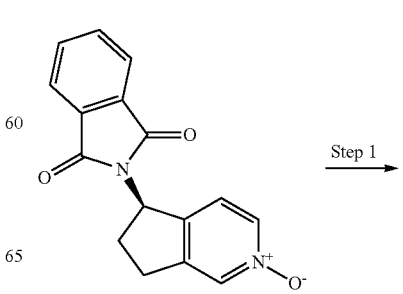

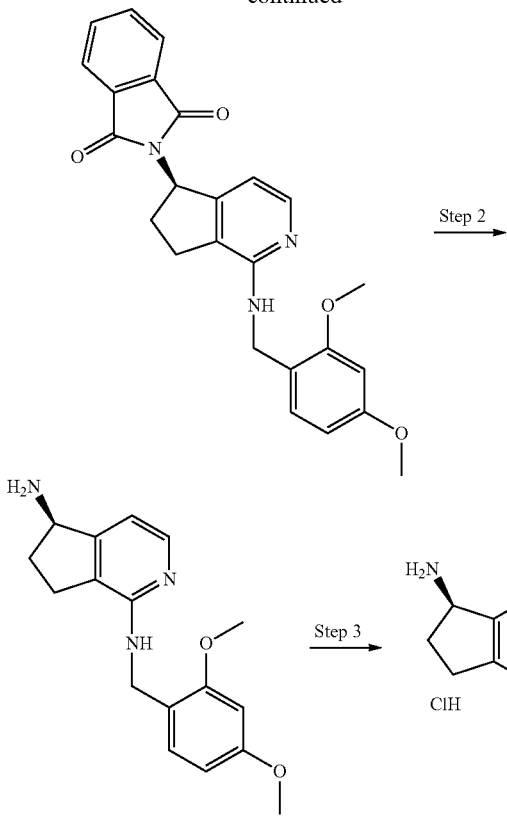

Step 1: 2-[(R)-1-(2,4-Dimethoxy-benzylamino)-6,7-dihydro-5H-[2]pyrindin-5-yl]-isoindole-1,3-dione 2-((R)-2-Oxy-6,7-dihydro-5H-[2]pyrindin-5-yl)-isoindole-1,3-dione (Intermediate 33, 3.5 g, 11.2 mmol) is dissolved in anhydrous dichloromethane (50 ml), then bromotripyrrolidinophosphonium hexafluorophosphate (9.43 g, 20.2 mmol), 2,4-dimethoxybenzylamine (2.19 ml, 14.6 mmol) and N,N-diisopropylethylamine (6.80 ml, 39.3 mmol) are added at 0° C. and the mixture is stirred at room temperature overnight. Dichloromethane (50 ml) is added and the mixture is washed with NaHCO$_3$ aq. sat. solution (50 ml) and brine (50 ml). the organic layer is collected, dried over sodium sulphate filtered and concentrated. The residue is purified by flash chromatography (20-100% ethyl acetate in cyclohexane) to give the title compound (Yield 3.5 g).

LC (Method 1): $t_R$=1.23 min; Mass spectrum (ES+): m/z=430 [M+H]$^+$

Step 2: (R)—N*1*-(2,4-Dimethoxy-benzyl)-6,7-dihydro-5H-[2]pyrindine-1,5-diamine

2-[(R)-1-(2,4-Dimethoxy-benzylamino)-6,7-dihydro-5H-[2]pyrindin-5-yl]-isoindole-1,3-dione (7 g, 15.5 mmol) and hydrazine (50% aq. solution, 2.91 ml, 46.4 mmol) are dissolved in ethanol (20 ml) and tetrahydrofuran (20 ml). The mixture is heated at 70° C. for 3 hours. The solution is concentrated and the residue is purified by flash chromatography (0-30% isopropanol in dichloromethane) to give the title compound (Yield 3.2 g).

LC (Method 2): $t_R$=3.52 min; Mass spectrum (ES+): m/z=300 [M+H]$^+$

Step 3: (R)-6,7-Dihydro-5H-[2]pyrindine-1,5-diamine dihydrochloride (R)—N*1*-(2,4-Dimethoxy-benzyl)-6,7-dihydro-5H-[2]pyrindine-1,5-diamine (3.2 g, 10.6 mmol) is dissolved in HCl 37% aq. solution (10 ml). The mixture is stirred at 70° C. for 10 minutes. The mixture is concentrated under vacuum and the residue is triturated with diethyl ether to give the title compound (Yield 3 g).

LC (Method 7): $t_R$=0.50 min; Mass spectrum (ES+): m/z=150 [M+H]$^+$

Intermediate 35

2-((R)-1-Oxy-6,7-dihydro-5H-[1]pyrindin-5-yl)-isoindole-1,3-dione

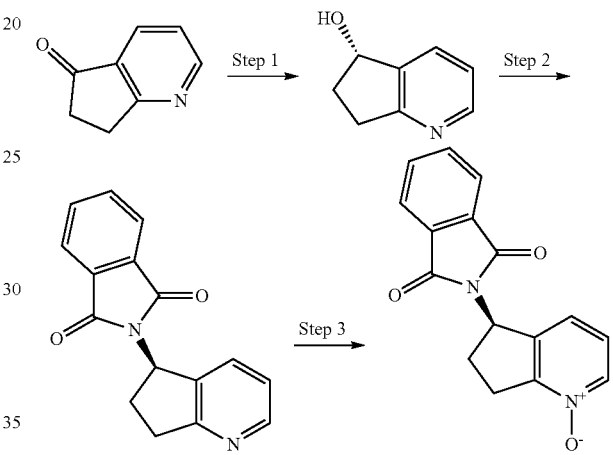

Step 1: (S)-6,7-Dihydro-5H-[1]pyrindin-5-ol

Triethylamine (32.6 ml, 232.8 mmol) is dissolved in dichloromethane (200 ml), the mixture is cooled to 0° C. and formic acid (9.82 ml, 262.8 mmol) is added dropwise, then 6,7-dihydro-[1]pyridin-5-one (commercially available from SANTAILABS ADH-7693, 10 g, 75.1 mmol) and chloro [(1S,2S)-(+2-amino-1,2-diphenylethyl)(4-toluensulfonyl) amido] (mesitylene) ruthenium(II) (200 mg, 0.75 mmol) are added. The mixture is stirred at room temperature overnight. Dichloromethane (100 ml) is added and the solution is washed with Na$_2$CO$_3$ aq. sat. solution, the organic layer is collected, dried over sodium sulphate filtered and concentrated to give the title compound. (9.0 g)

LC (Method 1): $t_R$=0.38 min; Mass spectrum (ES+): m/z=136 [M+H]$^+$

Chiral HPLC (Daicel chiralpak AD-H, Hexane:IPA 80:20 1 ml/min, 25° C.) T$_R$=4.78 min, 97.7%.

Absolute stereochemistry assigned by analogy with Noyori et. al., J. Am. Chem. Soc., 1995, 117 (28), pp 7562-7563.

Step 2: (R)-2-(6,7-Dihydro-5H-[1]pyrindin-5-yl)-isoindole-1,3-dione (S)-6,7-Dihydro-5H-[1]pyrindin-5-ol (1 g, 7.39 mmol), phthalimide (1.08 g, 7.39 mmol) and triphenylphosphine (1.94 g, 7.39 mmol) are dissolved in tetrahydrofuran (20 ml). The solution is cooled to 0° C. then diisopropylazodicarboxylate (1.46 ml, 7.39 mmol) is added. The mixture is stirred at room temperature for 3 hours. The solvent is removed under vacuum and the residue is purified by flash chromatography (0-80% ethyl acetate in cyclohexane) to give the title compound. (Yield 1.49 g)

LC (Method 1): $t_R$=0.89 min; Mass spectrum (ES+): m/z=265 [M+H]$^+$

Step 3: 2-((R)-1-Oxy-6,7-dihydro-5H-[1]pyrindin-5-yl)-isoindole-1,3-dione (R)-2-(6,7-Dihydro-5H-[1]pyrindin-5-yl)-isoindole-1,3-dione (1.49 g, 4.51 mmol) is dissolved in dichloromethane (20 ml), the solution is cooled to 0° C. and 3-chloroperoxybenzoic acid (1.31 g, 5.86 mmol) is added. The mixture is warmed to room temperature and stirred overnight. Dichloromethane (100 ml) is added and the solution is washed twice with Na$_2$CO$_3$ aq. sat. solution (20 ml), the organic layer is collected, dried over sodium sulphate filtered and concentrated to give the title compound. (Yield 1.6 g).

LC (Method 1): $t_R$=0.68 min; Mass spectrum (ES+): m/z=281 [M+H]$^+$

Intermediate 36

(R)-6,7-Dihydro-5H-[2]pyrindine-1,5-diamine dihydrochloride

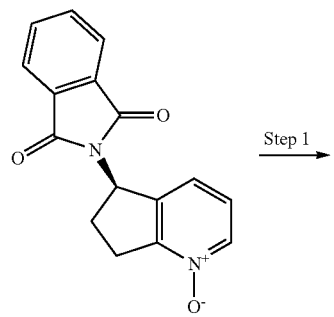

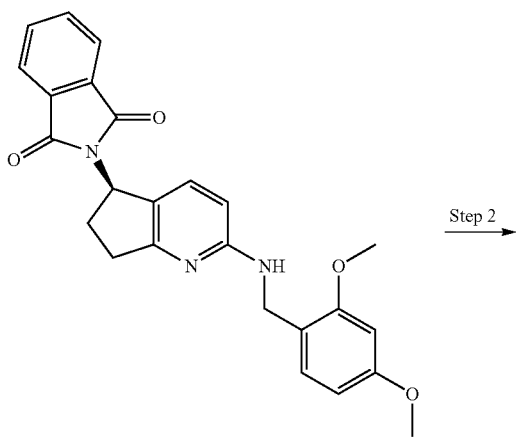

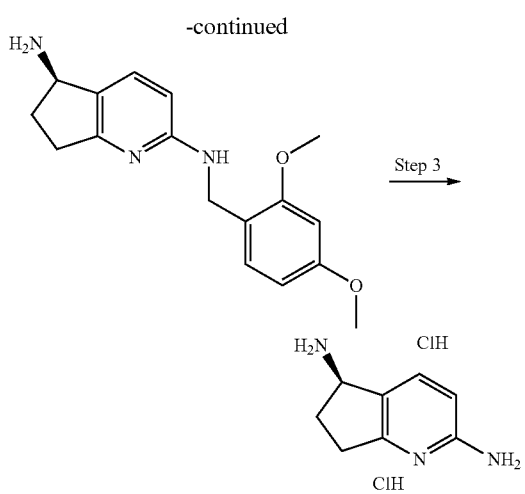

Step 1: 2-[(R)-2-(2,4-Dimethoxy-benzylamino)-6,7-dihydro-5H-[1]pyrindin-5-yl]-isoindole-1,3-dione 2-((R)-1-Oxy-6,7-dihydro-5H-[1]pyrindin-5-yl)-isoindole-1,3-dione (Intermediate 35, 1.6 g, 5.14 mmol) is dissolved in anhydrous dichloromethane (50 ml), then bromotripyrrolidinophosphonium hexafluorophosphate (4.31 g, 9.25 mmol), 2,4-dimethoxybenzylamine (1.03 ml, 6.68 mmol) and N,N-diisopropylethylamine (3.11 ml, 17.9 mmol) are added, the mixture is stirred at room temperature overnight. Dichloromethane (50 ml) is added and the mixture is washed with NaHCO$_3$ aq. sat. solution (50 ml) and brine (50 ml). The organic layer is collected, dried over sodium sulphate filtered and concentrated. The residue is purified by flash chromatography (20-100% ethyl acetate in cyclohexane) to give the title compound (Yield 0.67 g).

LC (Method 1): $t_R$=1.23 min; Mass spectrum (ES+): m/z=430 [M+H]$^+$

Step 2: (R)—N*2*-(2,4-Dimethoxy-benzyl)-6,7-dihydro-5H-[1]pyrindine-2,5-diamine

2-[(R)-2-(2,4-Dimethoxy-benzylamino)-6,7-dihydro-5H-[1]pyrindin-5-yl]-isoindole-1,3-dione (0.67 g, 1.48 mmol) and ethanolamine (0.54 ml, 8.9 mmol) are dissolved in toluene (20 ml). The mixture is heated at 70° C. for 3 hours. The organic layer is washed with water, collected and concentrated. The residue is purified by flash chromatography (20-100% ethyl acetate in cyclohexane) to give the title compound (Yield 220 mg).

LC (Method 1): $t_R$=0.73 min; Mass spectrum (ES+): m/z=300 [M+H]$^+$

Step 3: (R)-6,7-Dihydro-5H-[2]pyrindine-1,5-diamine dihydrochloride (R)—N*2*-(2,4-Dimethoxy-benzyl)-6,7-dihydro-5H-[1]pyrindine-2,5-diamine (220 mg, 0.69 mmol) is dissolved in HCl 37% aq. solution (2 ml) and tetrahydrofuran (2 ml). The mixture is stirred at 70° C. for 1 hour. The mixture is concentrated and the residue is triturated with diethyl ether to give the title compound (Yield 214 mg).

LC (Method 1): $t_R$=0.27 min; Mass spectrum (ES+): m/z=150 [M+H]$^+$

Intermediate 37

6,7-Dihydro-5H-[2]pyrindine-3,7-diamine dihydrochloride

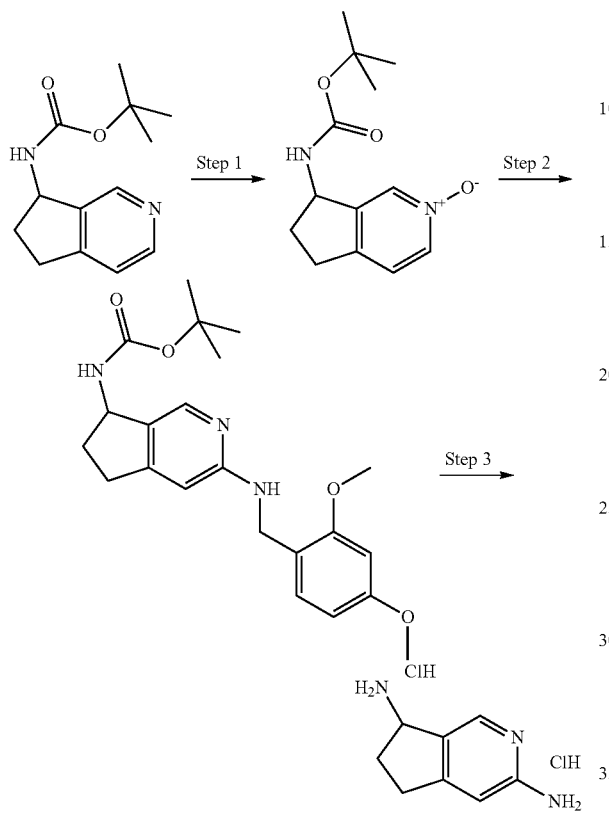

Step 1: (2-Oxy-6,7-dihydro-5H-[2]pyrindin-7-yl)-carbamic acid tert-butyl ester (6,7-Dihydro-5H-[2]pyrindin-7-yl)-carbamic acid tert-butyl ester (intermediate 29, 6 g, 25.6 mmol) is dissolved in dichloromethane (40 ml), the solution is cooled to 0° C. and 3-chloroperoxybenzoic acid (7.46 g, 33.29 mmol) is added. The mixture is warmed to room temperature and stirred overnight. Dichloromethane (20 ml) is added and the solution is washed twice with Na$_2$CO$_3$ aq. Sat. solution (20 ml) and brine (20 ml), the organic layer is collected, dried over sodium sulphate filtered and concentrated to give the title compound. (Yield 6 g).

LC (Method 1): t$_R$=0.69 min; Mass spectrum (ES+): m/z=251 [M+H]$^+$

Step 2: [3-(2,4-Dimethoxy-benzylamino)-6,7-dihydro-5H-[2]pyrindin-7-yl]-carbamic acid tert-butyl ester (2-Oxy-6,7-dihydro-5H-[2]pyrindin-7-yl)-carbamic acid tert-butyl ester (6 g, 23.97 mmol) is dissolved in anhydrous dichloromethane (40 ml), then bromotripyrrolidinophosphonium hexafluorophosphate (14.53 g, 31.1 mmol), 2,4-dimethoxybenzylamine (3.6 ml, 23.97 mmol) and N,N-diisopropylethylamine (15.6 ml, 91.1 mmol) are added, the mixture is stirred at room temperature overnight. Dichloromethane (40 ml) is added and the mixture is washed with NaHCO$_3$ aq. sat. solution (10 ml) and brine (10 ml). The organic layer is collected, dried over sodium sulphate, filtered and concentrated. The residue is purified by flash chromatography (20-100% ethyl acetate in cyclohexane) to give the title compound (Yield 2 g).

LC (Method 1): t$_R$=1.21 min; Mass spectrum (ES+): m/z=400 [M+H]$^+$

Step 3: 6,7-Dihydro-5H-[2]pyrindine-3,7-diamine dihydrochloride

[3-(2,4-Dimethoxy-benzylamino)-6,7-dihydro-5H-[2]pyrindin-7-yl]-carbamic acid tert-butyl ester (2 g, 5.0 mmol) is dissolved in HCl 37% aq. solution (10 ml). The mixture is stirred at room temperature for 1 h. The mixture is concentrated and the residue is triturated with diethyl ether to give the title compound (Yield 1 g).

LC (Method 1): t$_R$=0.30 min; Mass spectrum (ES+): m/z=150 [M+H]$^+$

Intermediate 38

6,7-Dihydro-5H-[2]pyrindine-1,7-diamine

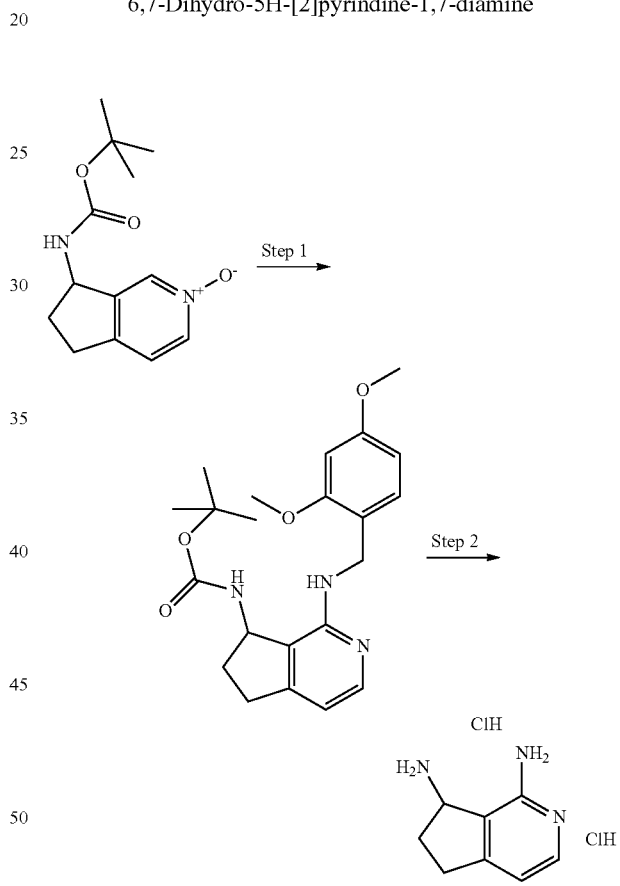

Step 1: [1-(2,4-Dimethoxy-benzylamino)-6,7-dihydro-5H-[2]pyrindin-7-yl]-carbamic acid tert-butyl ester The title compound was isolated as a second product during step 2 of the preparation of Example 37 (Yield 5 g).

LC (Method 1): t$_R$=1.29 min; Mass spectrum (ES+): m/z=400 [M+H]$^+$

Step 2: 6,7-Dihydro-5H-[2]pyrindine-1,7-diamine

[1-(2,4-Dimethoxy-benzylamino)-6,7-dihydro-5H-[2]pyrindin-7-yl]-carbamic acid tert-butyl ester (5 g, 12.5 mmol)

is dissolved in HCl 37% aq. solution. The mixture is stirred at room temperature for 1 hour. The mixture is concentrated and the residue is triturated with diethyl ether. (Yield 2.5 g)

LC (Method 1): $t_R$=0.30 min; Mass spectrum (ES+): m/z=150 [M+H]+

The compounds in the following table are synthesized in analogy to the method described for Intermediate 37.

1-(2-Methyl-quinolin-6-ylmethyl)-1H-[1,2,3]triazole-4-carboxylic acid (2-chloro-5,6,7,8-tetrahydroquinolin-5-yl)-amide (intermediate 28, 250 mg, 0.57 mmol) is dissolved in anhydrous toluene (8 ml), under inert atmosphere and diphenylmethanimine hydrochloride (616 mg, 2.83 mmol), palladium (II) acetate (51 mg, 0.23 mmol), 2,2'-bis(diphenyl-

| Intermediate | Structure | Starting intermediates | Yield | Analysis |
|---|---|---|---|---|
| 39 | (structure) | (6,7-Dihydro-5H-[1]pyrindin-5-yl)-carbamic acid tert-butyl ester, Intermediate 30 (1.0 g) | 1.2 g | LC (Method 8): $t_R$ = 0.37 min; Mass spectrum (ES+): m/z = 150 [M + H]+. |
| 40 | (structure) | (4-Methyl-6,7-dihydro-5H-[1]pyrindin-5-yl)-carbamic acid tert-butyl ester Intermediate 31 (2 g) | 700 mg | LC (Method 1): $t_R$ = 0.26 min; Mass spectrum (ES+): m/z = 164 [M + H]+. |
| 41 | (structure) | Intermediate 32 (1.7 g) | 250 mg | LC (Method 1): $t_R$ = 0.25 min; Mass spectrum (ES+): m/z = 150 [M + H]+. |

Synthesis of Examples

Example 1

1-(2-Methyl-quinolin-6-ylmethyl)-1H-[1,2,3]triazole-4-carboxylic acid (2-amino-5,6,7,8-tetrahydroquinolin-5-yl)-amide

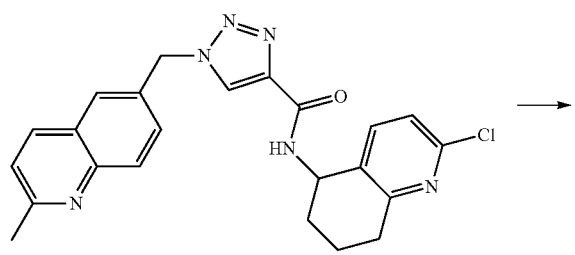

phosphino)-1,1'-binaphthyl (141 mg, 0.23 mmol), and cesium carbonate (1.84 g, 5.65 mmol) are added to the solution. The mixture is stirred at 110° C. for 30 hours. The mixture is filtered and concentrated. HCl 4M aq. solution (20 ml) is added to the filtrate and the mixture is stirred at room temperature for 40 minutes, H₂O (20 ml) is added and the aqueous solution is washed with toluene and dichloromethane. Ammonia (30 ml, 7N methanol solution) is added to the aqueous phase and the mixture is concentrated to dryness. The residue is purified by reverse phase flash chromatography (eluent 100% NH4COOH aq. solution (0.15 M) to 50:50 NH₄COOH aq. solution (0.15 M)/acetonitrile) and freeze dried to give the title compound (Yield 85 mg).

LC (Method 2): $t_R$=3.17 min; Mass spectrum (ES+): m/z=414 [M+H]+.

Example 2

1-(4-Pyrazol-1-ylmethyl-benzyl)-1H-[1,2,3]triazole-4-carboxylic acid (1-amino-6,7-dihydro-5H-[2]pyrindin-7-yl)-amide

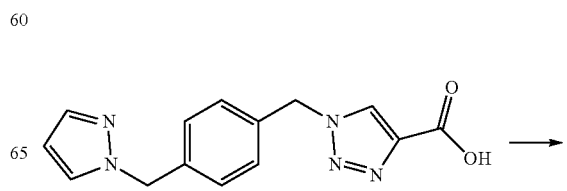

-continued

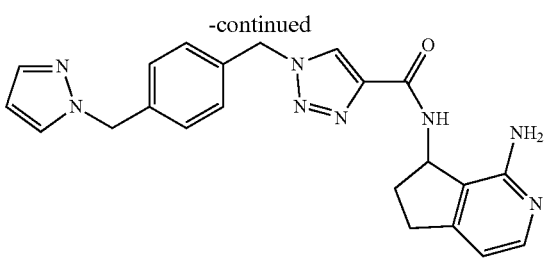

1-(4-Pyrazol-1-ylmethyl-benzyl)-1H-[1,2,3]triazole-4-carboxylic acid (intermediate 18, 100 mg, 0.33 mmol) and N,N-diisopropylethylamine (0.145 ml, 0.84 mmol) are dissolved in N,N-dimethylformamide (1 ml), then HATU (153 mg, 0.40 mmol) is added. The mixture is stirred for 5 minutes, then 6,7-Dihydro-5H-[2]pyrindine-1,7-diamine (Intermediate 38, 82 mg, 0.37 mmol) is added. the mixture is stirred at room temperature overnight. The solution is purified by reverse phase flash chromatography (eluent 0-50% acetonitrile in water) to give the title compound (Yield 104 mg).

LC (Method 2): $t_R$=3.48 min; Mass spectrum (ES+): m/z=415 [M+H]+

The examples in the following table are synthesized in analogy to the method described for Example 2.

| Ex. | Structure | Starting intermediates | Yield | Analysis |
|---|---|---|---|---|
| 3 | 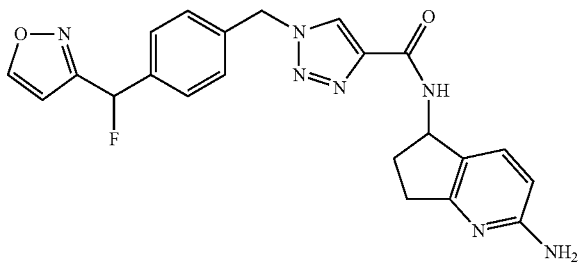 [SMILES: Nc1ccc2c(n1)CCC2NC(=O)c1cn(Cc2ccc(C(F)c3ccon3)cc2)nn1] | Acid: Intermediate 13 (50 mg) Amine: Intermediate 39 (38 mg) | 36 mg | LC (Method 2): $t_R$ = 3.45 min; Mass spectrum (ES+): m/z = 434 [M + H]+. |
| 4 | 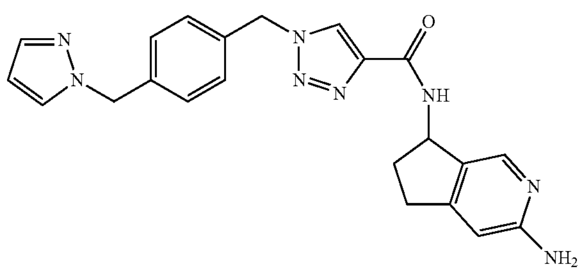 [SMILES: Nc1cc2c(cn1)C(NC(=O)c1cn(Cc3ccc(Cn4cccn4)cc3)nn1)CC2] | Acid: Intermediate 18 (50 mg) Amine: Intermediate 37 (41 mg) | 41 mg | LC (Method 2): $t_R$ = 3.22 min; Mass spectrum (ES+): m/z = 415 [M + H]+. |
| 5 | 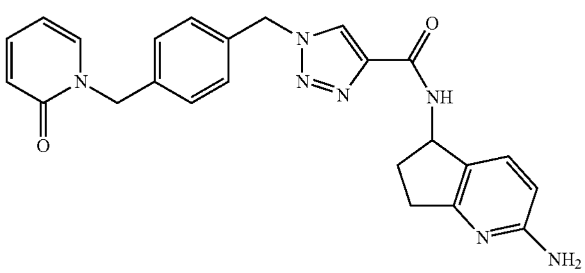 [SMILES: Nc1ccc2c(n1)CCC2NC(=O)c1cn(Cc2ccc(Cn3ccccc3=O)cc2)nn1] | Acid: Intermediate 14 (100 mg) Amine: Intermediate 39 (50 mg) | 12 mg | LC (Method 2): $t_R$ = 2.82 min; Mass spectrum (ES+): m/z = 441 [M + H]+. |
| 6 | 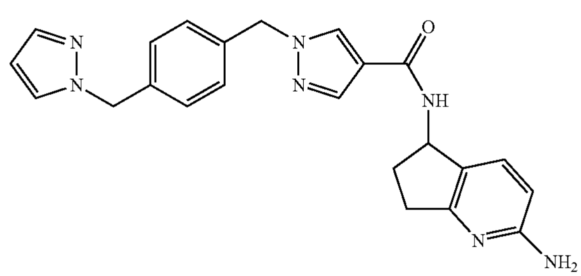 [SMILES: Nc1ccc2c(n1)CCC2NC(=O)c1cnn(Cc2ccc(Cn3cccn3)cc2)c1] | Acid: Intermediate 15 (100 mg) Amine: Intermediate 39 (55 mg) | 12 mg | LC (Method 2): $t_R$ = 3.02 min; Mass spectrum (ES+): m/z = 414 [M + H]+. |

| Ex. | Structure | Starting intermediates | Yield | Analysis |
|---|---|---|---|---|
| 7 | 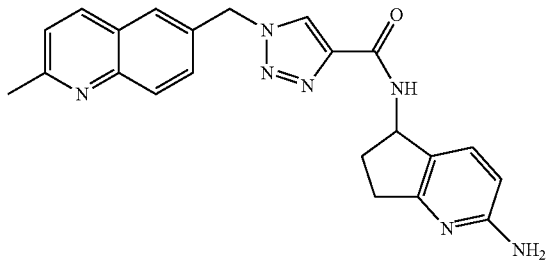 [SMILES: Cc1ccc2cc(Cn3cc(C(=O)NC4CCc5nc(N)ccc54)nn3)ccc2n1] | Acid: Intermediate 12 (50 mg) Amine: Intermediate 39 (29 mg) | 22 mg | LC (Method 8): $t_R$ = 1.94 min; Mass spectrum (ES+): m/z = 400 [M + H]$^+$. |
| 8 | 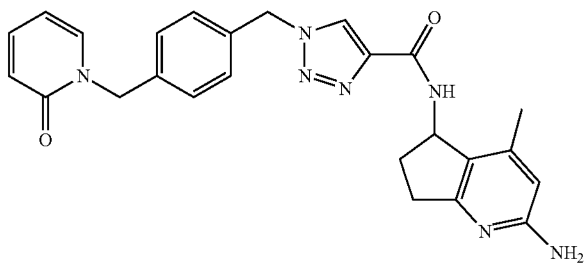 | Acid: Intermediate 14 (35 mg) Amine: Intermediate 40 (28 mg) | 25 mg | LC (Method 2): $t_R$ = 2.95 min; Mass spectrum (ES+): m/z = 455 [M + H]$^+$. |
| 9 | 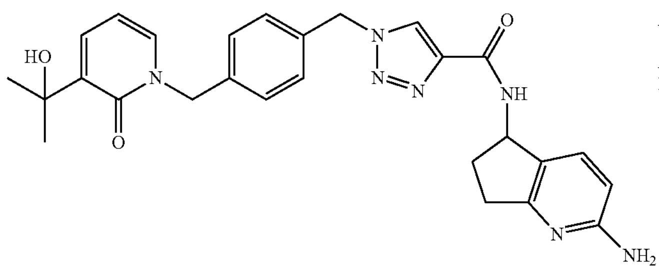 [SMILES: CC(C)(O)c1cccn(Cc2ccc(Cn3cc(C(=O)NC4CCc5nc(N)ccc54)nn3)cc2)c1=O] | Acid: Intermediate 19 (35 mg) Amine: Intermediate 39 (22 mg) | 25 mg | LC (Method 2): $t_R$ = 3.25 min; Mass spectrum (ES+): m/z = 500 [M + H]$^+$. |
| 10 | 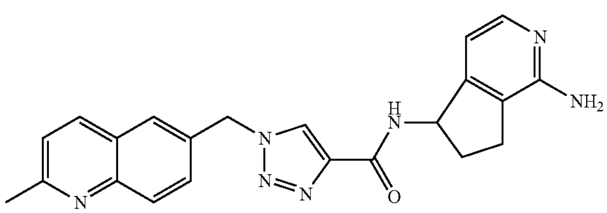 [SMILES: Cc1ccc2cc(Cn3cc(C(=O)NC4CCc5c4ccnc5N)nn3)ccc2n1] | Acid: Intermediate 12 (30 mg) Amine: Intermediate 41 (44 mg) | 25 mg | LC (Method 1): $t_R$ = 0.95 min; Mass spectrum (ES+): m/z = 400 [M + H]$^+$. |

The stereoisomers of Example 10 (25 mg) are separated by HPLC using a chiral stationary phase to give Example 11 (6 mg) and Example 12 (6 mg).

Method for Separation:

HPLC apparatus type: Waters 600 Pump, 2767 Autosampler, UV Detector 2489; column: Daicel Chiralpak AD-H, 5.0 µm, 250 mm×20 mm; method: eluent hexane/IPA 65:35; flow rate: 15 mL/min, temperature: 25° C.; UV Detection: 230 nm Example 11

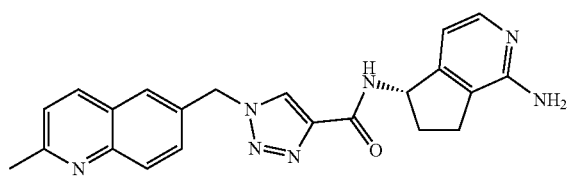

stereoisomer 1, known absolute stereochemistry

Example 12

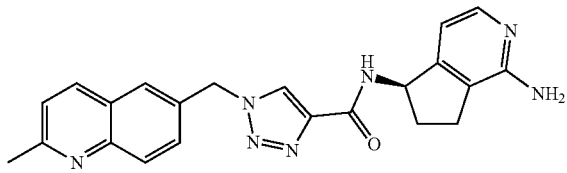

stereoisomer 2 known absolute stereochemistry

| Example | Chiral HPLC (Method C1) $R_t$ [min] | HPLC-MS (Method 7): $R_t$ [min] | MS (ESI pos): m/z |
|---|---|---|---|
| 11 | 19.33 | 2.36-2.47 | 400 |
| 12 | 29.25 | 2.37-2.46 | 400 |

Method C1:

Column Daicel Chiralpak AD-H, eluent Hexane-Ethanol 70:30, 1 ml/min, 25° C.

Example 13

1-[6-((S)-3-Methyl-pyrrolidin-1-yl)-pyridin-3-ylm-ethyl]-1H-pyrazole-4-carboxylic acid ((R)-2-amino-6,7-dihydro-5H-[1]pyrindin-5-yl)amide

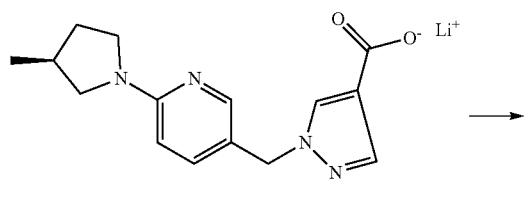

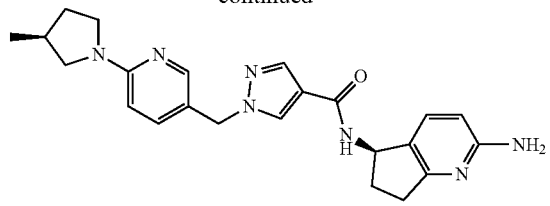

1-[6-((S)-3-Methyl-pyrrolidin-1-yl)-pyridin-3-ylmethyl]-1H-pyrazole-4-carboxylic acid, lithium salt (Intermediate 22, 40 mg, 0.14 mmol), (R)-6,7-Dihydro-5H-[1]pyrindine-2,5-diamine dihydrochloride (Intermediate 36, 47 mg), PyBop (85 mg, 0.16 mmol) and triethylamine (95 uL, 0.68 mmol) are combined in N,N-dimethylformamide (5 mL) and stirred overnight. The solvent is removed, the residue suspended in dichloromethane and washed with 0.2 M aqueous NaOH solution, dried and the solvent removed. The residue is purified by flash chromatography (0-10% methanol in dichloromethane) to give the title compound (Yield: 23 mg).

LC (Method 2): $t_R$=3.58 min; Mass spectrum (ES+): m/z=418 [M+H]$^+$.

The examples in the following table are synthesized in analogy to the method described for Example 13.

| Ex. | Structure | Starting intermediates, Conditions | Yield | Analysis |
|---|---|---|---|---|
| 14 | 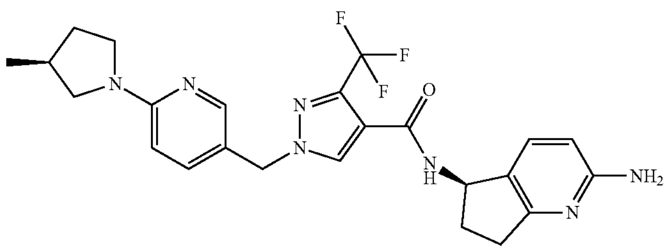 [SMILES: C[C@H]1CCN(c2ccc(Cn3cc(C(=O)N[C@@H]4CCc5nc(N)ccc54)c(C(F)(F)F)n3)cn2)C1] | Acid: Intermediate 23 (60 mg) Amine: Intermediate 36 (59 mg) | 17 mg | LC (Method 6): $t_R$ = 2.97 min; Mass spectrum (ES+): m/z = 486 [M + H]$^+$. |
| 15 | 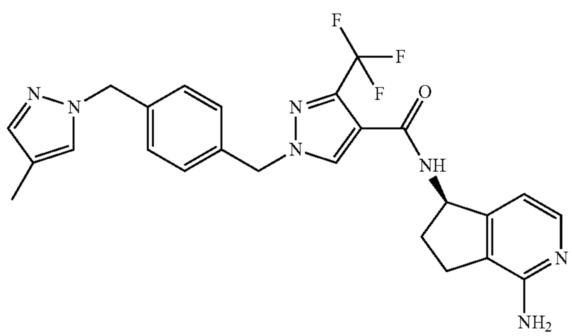 [SMILES: Cc1cnn(Cc2ccc(Cn3cc(C(=O)N[C@@H]4CCc5c4ccnc5N)c(C(F)(F)F)n3)cc2)c1] | Acid: Intermediate 26 (60 mg) Amine: Intermediate 34 (44 mg) 2 h reaction, Purification by preparative RP-HPLC-MS | 45 mg | LC (Method 2): $t_R$ = 3.86 min; Mass spectrum (ES+): m/z = 496 [M + H]$^+$. |
| 16 | 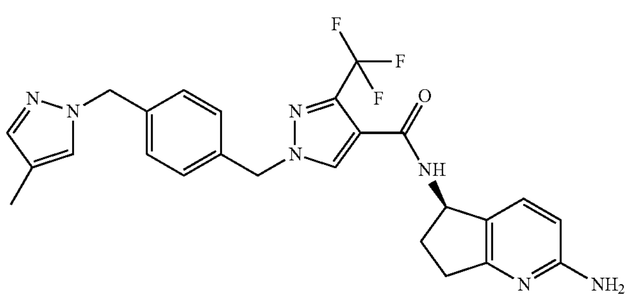 [SMILES: Cc1cnn(Cc2ccc(Cn3cc(C(=O)N[C@@H]4CCc5nc(N)ccc54)c(C(F)(F)F)n3)cc2)c1] | Acid: Intermediate 26 (60 mg) Amine: Intermediate 36 (59 mg) 2 h reaction, Purification by preparative RP-HPLC-MS | 32 mg | LC (Method 2): $t_R$ = 3.97 min; Mass spectrum (ES+): m/z = 496 [M + H]$^+$. |

The invention claimed is:
1. A compound of formula (I)

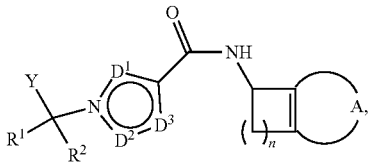

wherein
of $D^1$ to $D^3$
(i) each denote N, or
(ii) 2 denote N and 1 denotes CH, or
(iii) 1 denotes N, 2 denote CH, or
(iv) each denote CH
and one or two H-atoms attached to C optionally are replaced by a substituent selected from the group consisting of $C_{1-4}$-alkyl, —$CF_3$, —$CHF_2$, —CN and —$OCH_3$;
n is 1, 2 or 3;

denotes a 4-membered bridge composed of a —C($NH_2$)=N— unit and a second unit of —CH=CH— including both orientations for unsymmetric units, wherein a H-atom attached to a C-atom optionally is replaced by a substituent selected from the group consisting of F, Cl, $CH_3$, $CF_3$ and $CHF_2$;
$R^1$ denotes H, F, CN, $C_{1-3}$-alkyl, $CF_3$, OH, or —$OCH_3$,
$R^2$ denotes H, F, CN, $CF_3$, $CHF_2$, —$OCH_3$ or a $C_{1-3}$-alkyl group optionally substituted by —OH,
or $R^1$ and $R^2$ together denote =O or together with the carbon atom they are attached to form a 3-7 membered saturated ring system wherein 1 —$CH_2$— group optionally is replaced by O, S or NH,
Y denotes the group $Y^1$ or $Y^2$-L-$Y^1$—, wherein
$Y^1$ is selected from the group consisting of a phenyl ring, a tetrazolyl ring,
a 5-membered heteroaromatic ring containing 1 —NH—, —O— or —S— ring member,
a 5-membered heteroaromatic ring containing 1 —NH—, —O— or —S— ring member and additionally 1 or 2 =N— ring members,
a 6-membered heteroaromatic ring containing 1, 2 or 3 =N— ring members,
wherein optionally a second ring is annulated to said phenyl ring or to said 5- or 6-membered heteroaromatic rings and said second ring is 5- or 6-membered carbocyclic or heterocyclic, partially unsaturated, aromatic or heteroaromatic and optionally 1 or 2 ring members are independently selected from =N— and —NH—, or 1 ring member is 1 =N— and 1 ring member is O, S or —NH—,
and wherein in said second ring 1 —$CH_2$— group linked to a N-atom optionally is replaced by —C(O)—, and
wherein said phenyl ring, tetrazolyl ring, 5- or 6-membered heteroaromatic ring, annulated phenyl ring and annulated 5- or 6-membered heteroaromatic ring are optionally substituted at one or two carbon atoms by a halogen atom, $C_{1-3}$-alkyl, —$CF_3$, —CN, —OH, HO—$C_{1-3}$-alkyl- or $C_{1-3}$-alkyloxy-, and
wherein the H-atom in one or more NH groups present in Y optionally is replaced by $C_{1-3}$-alkyl-;
L denotes a bond or a linker selected from —C($R_3R_4$)— and —O—, wherein
$R^3$ denotes H, F, CN, $C_{1-3}$-alkyl, $CF_3$, $CHF_2$, —OH or —$OCH_3$,
$R^4$ denotes H, F, CN, $CF_3$, $CHF_2$, —$OCH_3$ or a $C_{1-3}$-alkyl group optionally substituted by —OH,
or $R^3$ and $R^4$ together denote =O or together with the carbon atom they are attached to form a 3-7 membered saturated ring system wherein 1 —$CH_2$— group optionally is replaced by O, S or NH,
$Y^2$ is attached to L via a C-atom or, where applicable, via a N-atom and is selected from the group consisting of a phenyl ring, a tetrazolyl ring,
a 5-membered heteroaromatic ring containing 1 >N—, —NH—, —O— or —S— ring member,
a 5-membered heteroaromatic ring containing 1 >N—, —NH—, —O— or —S— ring member and additionally 1 or 2 =N— ring members,
a 6-membered heteroaromatic ring containing 1, 2 or 3 =N— ring members,
a 5- or 6-membered carbocyclic or heterocyclic, saturated or partially unsaturated ring wherein optionally 1 or 2 ring members are independently selected from a N-atom and —NH—, or 1 ring member is a N-atom and 1 ring member is O, S or —NH—,
and wherein 1 —$CH_2$— group linked to a N-atom optionally is replaced by —C(O)—, and
wherein said phenyl ring, tetrazolyl ring, 5- or 6-membered heteroaromatic ring, 5- or 6-membered carbocyclic or heterocyclic, saturated or partially unsaturated rings are optionally substituted at one or two carbon atoms by one or, in case of saturated carbon atoms, also by two groups independently selected from halogen atoms, $C_{1-3}$-alkyl, —$CF_3$, —CN, —OH, HO—$C_{1-3}$-alkyl- and $C_{1-3}$-alkyloxy-, with the proviso that two substituents containing an O-atom cannot be attached to the same carbon atom, and wherein the H-atom in one or more NH groups present in $Y^2$ optionally is replaced by $C_{1-3}$-alkyl-;
wherein in any definition mentioned hereinbefore and if not specified otherwise, any alkyl group or sub-group may be straight-chained or branched,
or a salt thereof.

2. The compound according to claim 1, wherein
of $D^1$ to $D^3$
(i) 2 denote N and 1 denotes CH, or
(ii) 1 denotes N, and 2 denote CH,
and one or two H-atoms attached to C optionally are replaced by a substituent selected from the group consisting of $C_{1-3}$-alkyl, —$CF_3$, —CN and —$OCH_3$, and
Y denotes the group $Y^1$ or $Y^2$-L-$Y^1$—, wherein
$Y^1$ is selected from the group consisting of a phenyl ring and a pyridyl ring,
wherein optionally a second ring is annulated to said phenyl or pyridyl ring and said second ring is 5- or 6-membered, aromatic or heteroaromatic and optionally 1 or 2 ring members are independently selected from =N— and —NH—, or 1 ring member is =N— and 1 ring member is 0, S or —NH—, wherein each of said phenyl ring, pyridyl ring, annulated phenyl ring and annulated pyridyl ring are optionally substituted at one or two carbon atoms by a halogen atom, $C_{1-3}$-alkyl, or —$CF_3$, and wherein the H-atom in one or more NH groups present in Y optionally is replaced by $C_{1-3}$-alkyl;

L denotes a bond or —$CH_2$—, and $Y^2$ is attached to L via a N-atom and is selected from the group consisting of a 5-membered heteroaromatic ring containing 1 >N— ring member as the attachment point and optionally additional 1 or 2 =N— ring members, a 5- or 6-membered heterocyclic, saturated or partially unsaturated ring containing 1 >N— ring member as the attachment point and optionally additional 1 or 2 O or NH ring members, wherein 1 —$CH_2$— group linked to a N-atom optionally is replaced by —C(O)—, and wherein said 5-membered heteroaromatic ring and 5- or 6-membered heterocyclic, saturated or partially unsaturated rings are optionally substituted at a carbon atom by a group selected from $C_{1-3}$-alkyl, —$CF_3$, —OH, HO—$C_{1-3}$-alkyl- and $C_{1-3}$-alkyloxy-, or a salt thereof.

3. The compound according to claim 1, wherein
A is selected from the group consisting of —C($NH_2$)=N—CH=CH—, —N=C($NH_2$)—CH=CH—, and —CH=C($NH_2$)—N=CH—, including both orientations regarding the attachment points, wherein a H-atom attached to a C-atom optionally is replaced by a substituent selected from the group consisting of F, $CH_3$ and $CF_3$, or a salt thereof.

4. The compound according to claim 2, wherein
$R^1$ denotes H, F, CN, $CH_3$ or $CF_3$, and
$R^2$ denotes H, F, CN, $CF_3$ or a $C_{1-3}$-alkyl group optionally substituted by —OH, or a salt thereof.

5. The compound according to claim 2, wherein
of $D^1$ to $D^4$
(i) 2 denote N and 1 denotes CH, or
(ii) 1 denotes N, and 2 denote CH,
and one or two H-atoms attached to C optionally are replaced by a substituent selected from the group consisting of $C_{1-3}$-alkyl, —$CF_3$, —CN and —$OCH_3$, A is selected from the group consisting of —C($NH_2$)=N—CH=CH—, —N=C($NH_2$)—CH=CH— and —CH=C($NH_2$)—N=CH—, including both orientations regarding the attachment points, wherein a H-atom attached to a C-atom optionally is replaced by a substituent selected from the group consisting of F, $CH_3$ and $CF_3$, Y denotes the group $Y^1$, wherein
$Y^1$ is a quinolinyl or isoquinolinyl ring optionally substituted at one or two carbon atoms by a halogen atom, $C_{1-3}$-alkyl, or —$CF_3$, Or Y denotes the group or $Y^2$-L-$Y^1$—, wherein
$Y^1$ is a phenyl ring, optionally substituted at one or two carbon atoms by a halogen atom, $C_{1-3}$-alkyl, or —$CF_3$, L denotes —$CH_2$—, and $Y^2$ is attached to L via a N-atom and is selected from the group consisting of a 5-membered heteroaromatic ring containing 1 >N— ring member as the attachment point and optionally additional 1 or 2 =N— ring members, a 5- or 6-membered heterocyclic, saturated or partially unsaturated ring containing 1 >N— ring member as the attachment point and optionally additional 1 O or NH ring members, wherein 1 —$CH_2$— group linked to a N-atom optionally is replaced by —C(O)—, and wherein said 5-membered heteroaromatic ring and 5- or 6-membered heterocyclic, saturated or partially unsaturated rings are optionally substituted at a carbon atom by a group selected from $C_{1-3}$-alkyl and —$CF_3$, or Y denotes the group $Y^2$-L-$Y^1$—, wherein
$Y^1$ is a pyridyl ring, optionally substituted at one or two carbon atoms by a halogen atom, $C_{1-3}$-alkyl, or —$CF_3$, L denotes a bond, and $Y^2$ is attached to L via a N-atom and is selected from the group consisting of a 5- or 6-membered heterocyclic, saturated or partially unsaturated ring containing 1 >N— ring member as the attachment point and optionally additional 1 =N— ring member, wherein said 5- or 6-membered heterocyclic, saturated or partially unsaturated ring is optionally substituted at a carbon atom by a group selected from $C_{1-3}$-alkyl, —$CF_3$, $R^1$ denotes H, F or $CH_3$,
$R^2$ denotes H, F, $CF_3$ or $CH_3$, and
n denotes 2 or 3, or a salt thereof.

6. The compound according to claim 1, with the stereochemistry shown in formula I.1

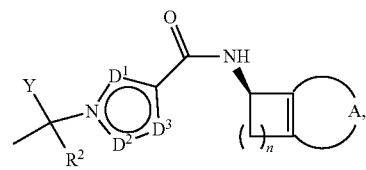

or a salt thereof.

7. The compound according to claim 1, with the stereochemistry shown in formula I.2

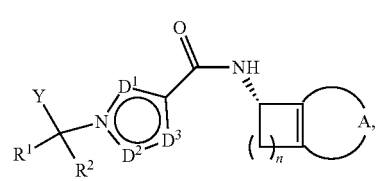

or a salt thereof.

8. A pharmaceutically acceptable salt of a compound according to claim 1.

9. A pharmaceutical composition comprising one or more compounds according to claim 1 or one or more pharmaceutically acceptable salts thereof, optionally together with one or more inert carriers and/or diluents.

10. A method for the therapeutic treatment of diseases or conditions which are influenced by inhibition of plasma kallikrein activity in a patient in need thereof, characterized in that a compound according to claim 1 or a pharmaceutically acceptable salt thereof is administered to the patient.

11. A pharmaceutical composition comprising one or more compounds according to claim 1 or one or more pharmaceutically acceptable salts thereof and one or more additional therapeutic agents, optionally together with one or more inert carriers and/or diluents.

12. The pharmaceutical composition according to claim 11 wherein the additional therapeutic agents are selected from the group consisting of antidiabetic agents, agents for the treatment of overweight and/or obesity, agents for the treatment of high blood pressure, heart failure and/or atherosclerosis and agents for the treatment of ocular diseases.

* * * * *